(12) United States Patent
Colvin, Jr. et al.

(10) Patent No.: US 7,851,225 B2
(45) Date of Patent: Dec. 14, 2010

(54) OXIDATION RESISTANT INDICATOR MOLECULES

(75) Inventors: Arthur E. Colvin, Jr., Mt. Airy, MD (US); Mark Alan Mortellaro, Frederick, MD (US); Aneta Modzelewska, Germantown, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 397 days.

(21) Appl. No.: 11/948,419

(22) Filed: Nov. 30, 2007

(65) Prior Publication Data

US 2008/0145944 A1 Jun. 19, 2008

Related U.S. Application Data

(60) Provisional application No. 60/903,291, filed on Feb. 26, 2007, provisional application No. 60/861,707, filed on Nov. 30, 2006.

(51) Int. Cl.
*G01N 33/66* (2006.01)
*G01N 33/50* (2006.01)
*G01N 33/00* (2006.01)
*C07F 5/02* (2006.01)
*C07F 5/00* (2006.01)

(52) U.S. Cl. .................. 436/95; 436/164; 436/94; 436/93; 436/91; 562/7; 562/1

(58) Field of Classification Search .................. 436/164, 436/95, 94, 93, 91; 562/7, 1
See application file for complete search history.

(56) References Cited

U.S. PATENT DOCUMENTS 5,503,770 A 4/1996 James et al.
6,319,540 B1 * 11/2001 Van Antwerp et al. ..... 427/2.13

FOREIGN PATENT DOCUMENTS

WO 02057788 A2 7/2002
WO 03078424 A1 9/2003
WO 2004096817 A1 11/2004

OTHER PUBLICATIONS

Jin et al., "Synthesis, Evaluation, and Computational Studies of Naphthalimide-Based Long-Wavelength Fluorescent Boronic Acid Reporters," Chem. Eur. J. 2008, 14:2795-2804.
Kaur et al., "Substituent Effect on Anthracene-Based Bisboronic Acid Glucose Sensors," Tetrahedron, 62 (2006), pp. 2583-2589.
Stones, D. et al., "Modular Solid-Phase Synthetic Approach to Optimize Structural and Electronic Properties of Oligoboronic Acid Receptors and Sensors for the Aqueous Recognition of Oligosaccharides," Chem. Eur. J., 10 (2004), pp. 92-100.
International Search Report PCT/US2007/024704, May 9, 2008, 15 pages.

* cited by examiner

*Primary Examiner*—Vickie Kim
*Assistant Examiner*—Christine T Mui
(74) *Attorney, Agent, or Firm*—Rothwell, Figg, Ernst & Manbeck PC

(57) ABSTRACT

Compounds having enhanced oxidation stability are disclosed. The compounds have an aryl boronic acid residue having one or more electron withdrawing groups on the aromatic moiety which contains the boronic acid residue, such that the molecule has enhanced oxidation resistance as compared to a corresponding molecule without the one or more electron withdrawing groups.

28 Claims, 9 Drawing Sheets

2-Methyl (8)     4-Cyano (14a)     4-Nitro (14b)
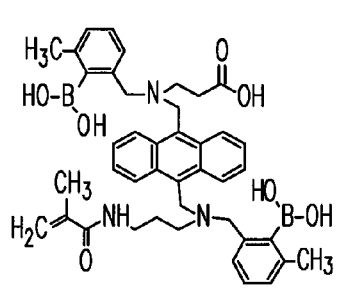 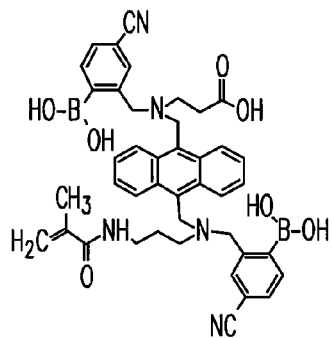 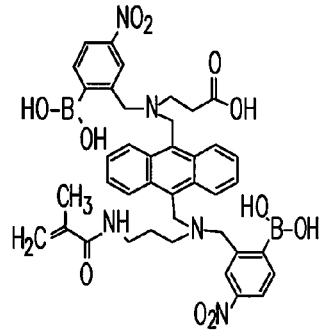
4-Trifluoromethylsulfone (21)     3,5-bis(trifluoromethyl)(27a)
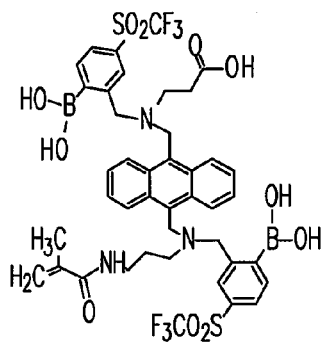 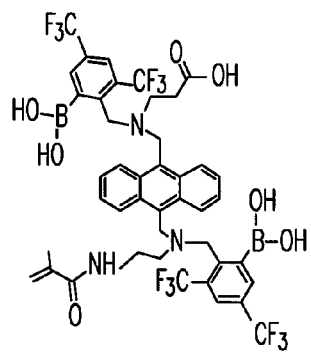
5-Trifluoromethyl (27b)     5-Fluoro (32a)     4-Chloro (32b)
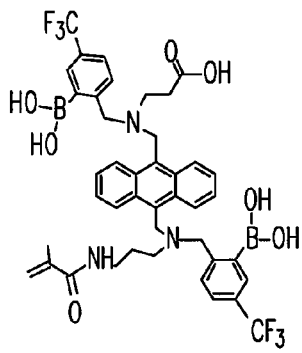 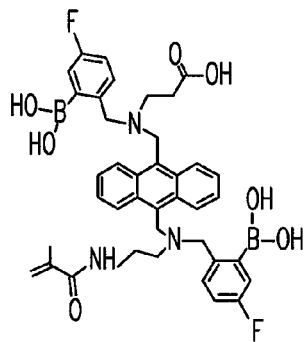 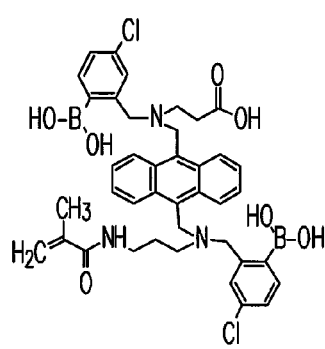
FIG.5B

OXIDATION RESISTANT INDICATOR MOLECULES

CROSS-REFERENCE TO RELATED APPLICATIONS

This application claims the benefit of U.S. Provisional Application No. 60/861,707 filed Nov. 30, 2006, and U.S. Provisional Application No. 60/903,291 filed Feb. 26, 2007.

STATEMENT REGARDING FEDERALLY SPONSORED RESEARCH OR DEVELOPMENT

Not applicable.

BACKGROUND OF THE INVENTION

1. Field of the Invention

The present invention relates to detectable indicators, including fluorescent indicators, having increased resistance to oxidation.

2. Description of the Related Art

Fluorescent molecules are used for a range of applications including fabric and color brighteners, signs, various inks for printing, diagnostics as tags and probes when linked to antibodies or other molecules, and can be configured at a molecular level to be used as chemical and biochemical active indicators specifically designed to detect certain analytes, for example glucose.

The complexation of carbohydrates, including glucose, with phenylboronic acid has been known for a long time and the reversibility of that interaction has served as a basis for the chromatographic separation of sugars.

Specifically, in 1959, Lorand and Edwards reported association constants for aqueous associations of phenylboronic acid with many saturated polyols; binding interactions ranged from very weak (e.g., ethylene glycol, $K_d$=360 mM) to moderately strong (e.g., glucose, $K_d$=9.1 mM). See J. Yoon, et al., *Bioorganic and Medicinal Chemistry* 1(4):267-71 (1993). The binding mechanism is believed to occur through displacement of the hydroxyl groups on a boronate moiety with adjacent hydroxyl groups on glucose.

U.S. Pat. No. 5,503,770 (James, et al.) describes a fluorescent boronic acid-containing compound that emits fluorescence of a high intensity upon binding to saccharides, including glucose. The fluorescent compound has a molecular structure comprising a fluorophore, at least one phenylboronic acid moiety and at least one amine-providing nitrogen atom where the nitrogen atom is disposed in the vicinity of the phenylboronic acid moiety so as to interact intramolecularly with the boronic acid. Such interaction thereby causes the compound to emit fluorescence upon saccharide binding. See also T. James, et al., *J. Am. Chem. Soc.* 117(35):8982-87 (1995).

Additionally, fluorescent sensors using an anthrylboronic acid-containing compound for detecting blood glucose are known in the art. For example, J. Yoon, et al., *J. Am. Chem. Soc.* 114:5874-5875 (1992) describe that anthrylboronic acid can be used as a fluorescent chemosensor for signaling carbohydrate binding, including binding of glucose and fructose.

Fluorescent molecules are susceptible to degradation, where they lose fluorescence intensity (or brightness) over time by often variable rates of oxidation. The oxidation may be commonly associated with photobleaching, which is technically "photo-oxidation", or may be oxidized by various reactive oxygen species within the local environment of the fluorescent molecule. Any number of potential oxidants exist in the environment and atmosphere such as ozone, or may exist inside a living body ranging from humans to bacteria. Inside a living body, normal reactive oxygen species (ROS) can include those involved in typical healthy healing reactions such as peroxide, hydroxyl radicals, peroxynitrite, superoxide, and others. Inside a living system there are also specific enzymes called oxygenases for the specific purpose of oxidation in the breakdown of molecules. An adverse result of reactive oxygen species or oxygenase activity on a fluorescent molecule is typically loss of fluorescence. In the case of an indicator molecule, or a passive tag, probe, or label, the useful life and sensitivity of the device, or diagnostic, is limited, or may be rendered completely ineffective by oxidative degradation of fluorescent signal. Therefore, there remains a need for fluorescent molecules that have increased resistance to oxidation.

BRIEF SUMMARY OF THE INVENTION

In one aspect, the present invention is directed to a method for using a molecule in oxidative conditions, which comprises:

a) obtaining a molecule having an aryl boronic acid residue having one or more electron withdrawing groups on the aromatic moiety which contains the boronic acid residue, such that the molecule has enhanced oxidation resistance as compared to a corresponding molecule without the one or more electron withdrawing groups; and b) subjecting the molecule having the one or more electron withdrawing groups to oxidative conditions.

In another aspect, the present invention is directed to a method for detecting the presence or concentration of an analyte in a sample in an oxidative environment, said method comprising:

a) exposing the sample to an indicator molecule having a detectable quality that changes when the indicator molecule is exposed to the analyte, said molecule comprising an aryl boronic acid residue having one or more electron withdrawing groups on the aromatic moiety which contains the boronic acid residue, such that the indicator molecule has enhanced oxidation resistance as compared to the corresponding molecule without the one or more electron withdrawing groups; and b) measuring any change in said detectable quality to thereby determine the presence or concentration of said analyte in said sample.

In another aspect, the present invention is directed to a compound having the following structure:

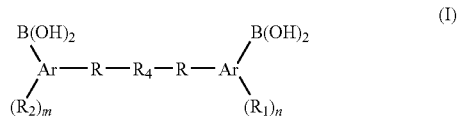

(I)

wherein:
- each Ar is an aryl group;
- each $R_1$ and $R_2$ are the same or different and are an electron withdrawing group;
- m and n are each independently integers from 1 to 10;
- $R_4$ is a detectable moiety; and
- each R is independently a linking group having from zero to ten contiguous or branched carbon and/or heteroatoms, with at least one R further containing a polymerizable monomeric unit;

and wherein the compound has enhanced oxidation resistance as compared to the corresponding compound without the one or more electron withdrawing groups.

In another aspect, the present invention is directed to a compound having the following structure:

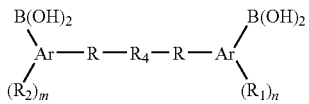

wherein:
- each Ar is an aryl group other than phenyl;
- each $R_1$ and $R_2$ are the same or different and are an electron withdrawing group;
- m and n are each independently integers from 1 to 10;
- $R_4$ is a detectable moiety; and
- each R is independently a linking group having from zero to ten contiguous or branched carbon and/or heteroatoms, with at least one R further containing a linking group capable of attachment to a solid support or a polymeric matrix;

and wherein the compound has enhanced oxidation resistance as compared to the corresponding compound without the one or more electron withdrawing groups.

In another aspect, the present invention is directed to a method for the production of an indicator macromolecule for detecting the presence or concentration of an analyte in an oxidative environment, said method comprising copolymerizing:

a) one or more indicator component monomers which individually are not sufficiently water soluble to permit their use in an aqueous environment for detecting the presence or concentration of said analyte, wherein the indicator component monomer comprises compound having the following structure:

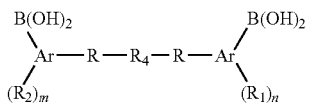

wherein:
- each Ar is an aryl group;
- each $R_1$ and $R_2$ are the same or different and are an electron withdrawing group;
- m and n are each independently integers from 1 to 10;
- $R_4$ is a detectable moiety; and
- each R is independently a linking group having from zero to ten contiguous or branched carbon and/or heteroatoms, with at least one R further containing a polymerizable monomeric unit; and b) one or more hydrophilic monomers; such that the resulting macromolecule is capable of detecting the presence or concentration of said analyte in an aqueous environment and wherein the compound has enhanced oxidation resistance as compared to the corresponding compound without the one or more electron withdrawing groups.

In another aspect, the present invention is directed to a compound having the following structure:

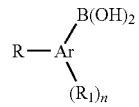

wherein:
- Ar is an aryl group;
- each $R_1$ is the same or different and is an electron withdrawing group;
- n is an integer from 1 to 10; and
- R is a linking group having from zero to ten contiguous or branched carbon and/or heteroatoms, which linking group further contains a polymerizable monomeric unit and a detectable moiety;

and wherein the compound has enhanced oxidation resistance as compared to the corresponding compound without electron withdrawing group(s).

In another aspect, the present invention is directed to a compound having the following structure:

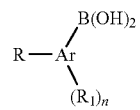

wherein:
- Ar is an aryl group;
- each $R_1$ is the same or different and is an electron withdrawing group;
- n is an integer from 1 to 10; and
- R is a linking group to a chromatographic support, said linking group having from zero to ten contiguous or branched carbon and/or heteroatoms;

and wherein the compound has enhanced oxidation resistance as compared to the corresponding compound without electron withdrawing group(s).

DETAILED DESCRIPTION OF THE INVENTION

Figure 1:
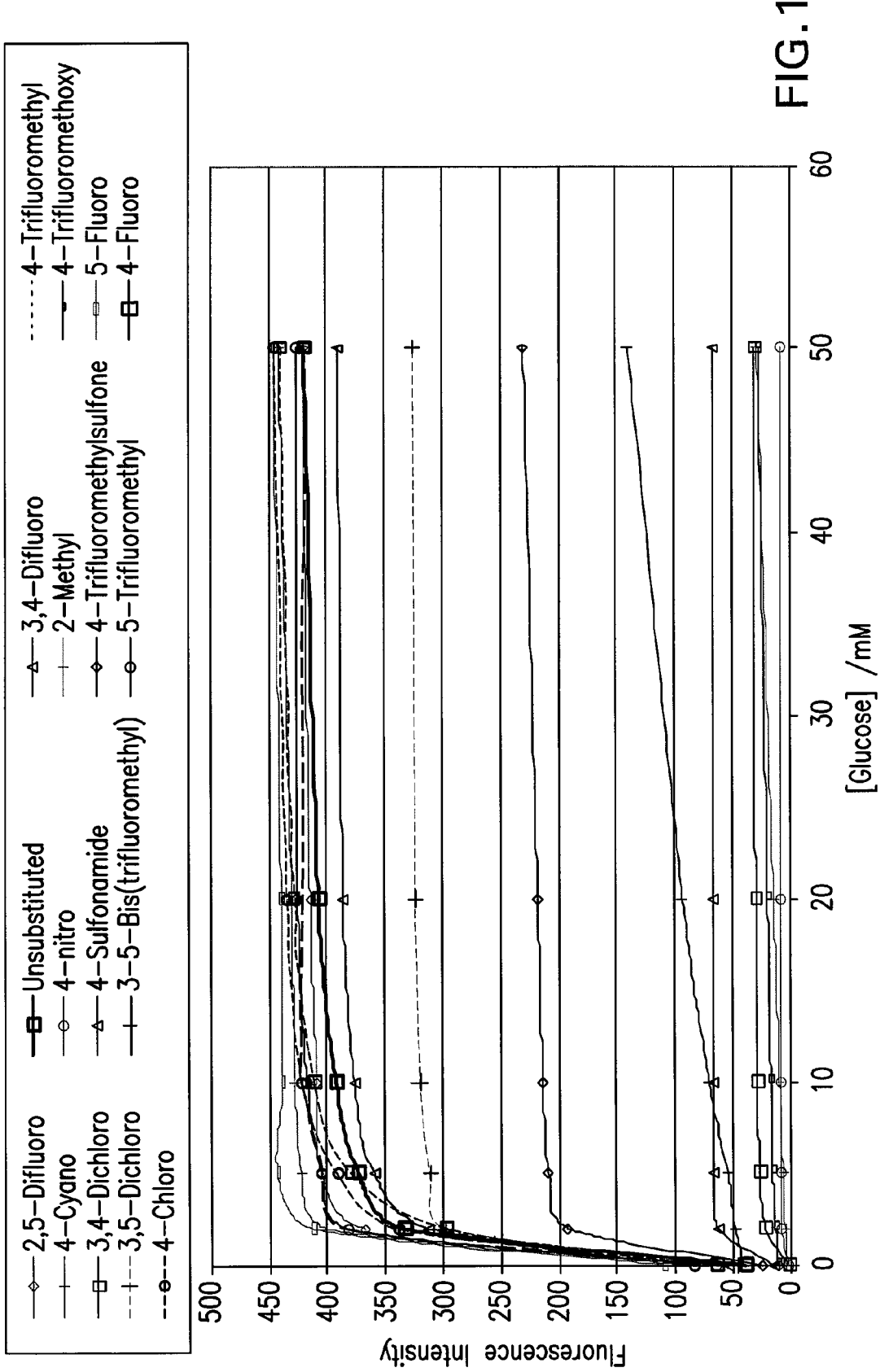
FIG. 1 illustrates the results of the experiment described in Example 1.

During the inventors' ongoing work to develop an implantable glucose sensor based on a fluorescent indicator molecule, an observation was made that in addition to photo-oxidation, which is a direct and predictable function of quantitative light cumulative exposure, that for a series of fluorescent indicator molecules tested in vivo, there is an additional, severe, and rapid fluorescent signal loss that occurs in vivo, but does not occur significantly in vitro.

Samples of a fluorescent indicator were implanted, and subsequently explanted some period of weeks later. The samples were then chemically analyzed following severe loss of signal. The analysis showed a specific reaction whereby the boronate recognition element of the indicator system had been specifically oxidized to a hydroxyl group, thereby causing total loss of activity (specifically, fluorescence modulation) in the molecule. This in vivo oxidation reaction is shown below:

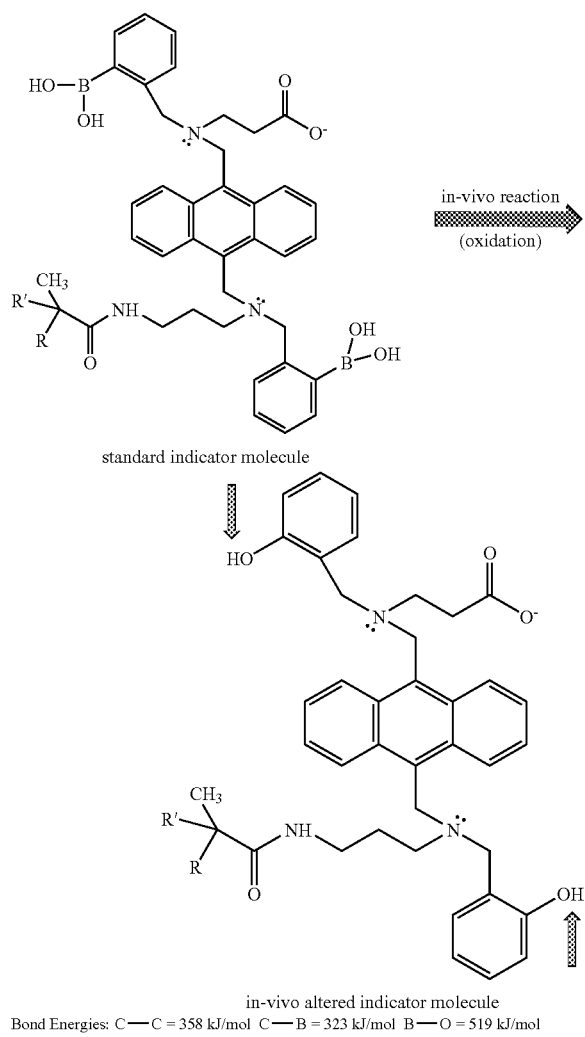

Bond Energies: C—C = 358 kJ/mol  C—B = 323 kJ/mol  B—O = 519 kJ/mol

The destructive in vivo oxidation reaction was shown to be very specific, oxidizing only the boronate group, and leaving a hydroxyl group in its place. The oxidation was duplicated in-vitro by treatment with 1, 5, and 10 uM hydrogen peroxide. Both in vitro and in vivo, only the boronate moiety was found to be oxidized to hydroxyl. This was unexpected since ROS were thought (by us) to be more generalized and indiscriminate in where they may oxidize and damage the molecule.

According to the present invention, indicator molecules containing an aryl boronic acid residue may be made more resistant to oxidation by adding one or more electron-withdrawing groups to the aromatic moiety which contains the boronic acid residue, thus stabilizing the boronate moiety. It will be understood that the term "aryl" encompasses a wide range of aromatic groups, such as phenyl, polynuclear aromatics, heteroaromatics, polynuclear heteroaromatics, etc. Non-limiting examples include phenyl, naphthyl, anthryl, pyridyl, etc.

A wide range of electron-withdrawing groups is within the scope of the invention, and includes, but is not limited to, halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, etc., or combinations thereof.

With respect to structures I and II above, $R_1$ and $R_2$ preferably are electron-withdrawing groups as described in the preceding paragraph. Most preferably, each of $R_1$ and $R_2$ is trifluoromethyl. Further, as noted above, in certain embodiments at least one of the R groups will contain a polymerizable monomer unit which will allow incorporation of structure (I) into a polymer. Such polymerizable units are well known, and include, but are not limited to vinyl, acrylate, methacrylate, acrylamide, methacrylamide, etc.

The indicator compounds of the present invention have a detectable quality (shown as constituent $R_4$ in structure I) that changes in a concentration-dependent manner when the compound is exposed to a sample containing glucose. Many such qualities are known and may be used in the present invention. For example, the indicator compound may include a luminescent (fluorescent or phosphorescent) or chemiluminescent moiety, an absorbance based moiety, etc. The indicator compound may include an energy donor moiety and an energy acceptor moiety, each spaced such that there is a detectable change when the indicator compound interacts with glucose. The indicator compound may include a fluorophore and a quencher, configured such that the fluorophore is quenched by the quencher when glucose is absent. In that situation, when glucose is present, the indicator undergoes a configurational change which causes the quencher to move sufficiently distant from the fluorophore so that fluorescence is emitted. Conversely, the fluorophore and quencher may be configured such that in the absence of glucose, they are sufficiently separated and the fluorophore emits fluorescence; upon interaction with glucose, the fluorophore and quencher are moved in sufficient proximity to cause quenching. The configurational change concept is described in more detail in U.S. published application 2002/0119581, incorporated herein by reference. In another embodiment, the quencher contains an aromatic boronic acid, and binding of the boronic acid to the target molecule (e.g., glucose) changes the quencher efficiency resulting in a detectable change. Such is described in U.S. Patent Application Publication 2006/0083688, the content of which is incorporated herein by reference.

Alternatively, the indicator may include a moiety such as a fluorophore capable of interacting with the recognition element or another moiety spatially disposed with respect to the recognition element such that in the absence of glucose, the fluorophore emits fluorescence. Upon addition of glucose, the glucose competes with the interaction between the fluorophore and the recognition element, or the interaction between the fluorophore and the other moiety spatially disposed with respect to the recognition element, causing a reduction in fluorescence. It will also be recognized that the indicator may be chosen such that the fluorophore emits no fluorescence, or a relatively low level of fluorescence, when the fluorophore interacts with the recognition element or another moiety spatially disposed with respect to the recognition element in the absence of glucose. Upon addition of glucose, the glucose competes with the interaction between the fluorophore and the recognition element, or the interaction between the fluorophore and the other moiety spatially disposed with respect to the recognition element, causing an increase in fluorescence.

Other detectable moieties include those whose fluorescence is affected by glucose interaction via photoinduced electron transfer or inductive effects. These include the lanthanide chelates disclosed in U.S. Pat. No. 6,344,360, incorporated herein by reference; polyaromatic hydrocarbons and their derivatives; coumarins; BoDiPy; dansyl; catechols; etc. Another class of moieties include those whose absorbance spectrum changes upon interaction of the indicator compound with glucose, including Alizarin Red, etc. Another class of moieties include those whose fluorescence is modulated by proximity effects, e.g., energy donor/acceptor pairs such as dansyl/dabsyl, etc.

Preferably, the detectable quality is a detectable spectral change, such as changes in absorptive characteristics (e.g., absorbtivity and/or spectral shift), in fluorescent decay time (determined by time domain or frequency domain measurement), fluorescent intensity, fluorescent anisotropy or polarization; a spectral shift of the emission spectrum; a change in time-resolved anisotropy decay (determined by time domain or frequency domain measurement), etc.

It will be understood that until use, the boronic acid recognition elements may be capped with a protecting group. Such groups are well known, and include neopentyl glycol, pinacol, etc. In certain embodiments, the capped recognition element is decapped in the medium in which the compound is to be used.

The present invention also encompasses compounds with improved resistance to oxidation that do not necessarily contain a detectable group. Such compounds can be used in, for example, chromatography resins used to separate sugars. In that instance, the present compounds would be linked to a resin or other solid support via a linker that is capable of withstanding the conditions to which the resin or support is subjected.

The indicator compounds of the present invention, if soluble, may be used directly in solution if so desired. On the other hand, if the desired application so requires, the indicator compounds may be immobilized (such as by mechanical entrapment or covalent or ionic attachment) onto or within an insoluble surface or matrix such as glass, plastic, polymeric materials, etc. When the indicator compound is entrapped within, for example, another polymer, the entrapping material preferably should be sufficiently permeable to glucose to allow suitable interaction between glucose and the indicator compound.

If the indicator compounds are sparingly soluble or insoluble in water, yet detection in an aqueous medium is desired, the indicator compound may be co-polymerized with a hydrophilic monomer to form a hydrophilic macromolecule as described in, for example, U.S. Pat. No. 6,794,195, the contents of which are incorporated herein by reference.

Suitable linking groups to a polymer or support may include groups from about 1 to about 20 contiguous atoms, which may be branched or substituted and which may include one or more heteroatoms, which terminate in a functional group capable of further reaction or attachment to a polymer or support. Examples of suitable linking groups include alkyl; aryl; acyl; polyamide; polyether; all optionally substituted, and combinations thereof.

It will also be understood from the above definition that the present compounds and detection systems may be in polymeric form. Thus, an integral compound (containing recognition elements and detectable moiety) could be linked to an existing polymer, or the integral compound in monomeric form could be polymerized or co-polymerized with another suitable monomer to form a polymer. Alternatively, two separate monomeric components (e.g., one containing the recognition elements, and one containing a detectable moiety) could be copolymerized so that the resulting polymer contains all necessary elements of the system.

Many uses exist for the indicator compounds of the present invention, including uses as indicators in the fields of energy, medicine and agriculture. For example, the indicator compounds can be used to detect sub-levels or supra-levels of glucose in physiological buffers or fluids, such as blood, plasma, serum, interstitial fluid, cerebrospinal fluid, urine, saliva, intraocular fluid, lymph, tears, or sweat, thus providing valuable information for diagnosing or monitoring such diseases as diabetes and adrenal insufficiency.

Medical/pharmaceutical production of glucose for human therapeutic application requires monitoring and control.

Uses for the present invention in agriculture include detecting levels of glucose in soybeans and other agricultural products. Glucose must be carefully monitored in critical harvest decisions for such high value products as wine grapes. As glucose is the most expensive carbon source and feedstock in fermentation processes, glucose monitoring for optimum reactor feed rate control is important in power alcohol production. Reactor mixing and control of glucose concentration also is critical to quality control during production of soft drinks and fermented beverages, which consumes the largest amounts of glucose and fermentable (vicinal diol) sugars internationally.

When the indicator compounds incorporate fluorescent indicator substituents, various detection techniques also are known in the art. For example, the compounds of the invention can be used in fluorescent sensing devices (e.g., U.S. Pat. No. 5,517,313) or can be bound to polymeric material such as test paper for visual inspection. This latter technique would permit, for example, glucose measurement in a manner analogous to determining pH with a strip of litmus paper. The compounds described herein may also be utilized as simple reagents with standard benchtop analytical instrumentation such as spectrofluorometers or clinical analyzers as made by Shimadzu, Hitachi, Jasco, Beckman and others. These molecules would also provide analyte specific chemical/optical signal transduction for fiber optic-based sensors and analytical fluorometers as made by Ocean Optics (Dunedin, Fla.), or Oriel Optics.

U.S. Pat. No. 5,517,313, the disclosure of which is incorporated herein by reference, describes a fluorescence sensing device in which the compounds of the present invention can be used to determine the presence or concentration of glucose in a liquid medium. The sensing device comprises a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, or in a waveguide upon which the indicator matrix is disposed, such that incident light from the light source causes the indicator molecules to fluoresce. The high-pass filter allows emitted light to reach the photodetector, while filtering out scattered incident light from the light source. The fluorescence of the indicator molecules employed in the device described in U.S. Pat. No. 5,517,313 is modulated, e.g., attenuated or enhanced, by the local presence of glucose.

In the sensor described in U.S. Pat. No. 5,517,313, the material which contains the indicator molecule is permeable to the analyte. Thus, the analyte can diffuse into the material from the surrounding test medium, thereby affecting the fluorescence emitted by the indicator compounds. The light source, indicator compound-containing material, high-pass filter and photodetector are configured such that at least a portion of the fluorescence emitted by the indicator compounds impacts the photodetector, generating an electrical signal which is indicative of the concentration of glucose in the surrounding medium.

In accordance with other possible embodiments for using the indicator compounds of the present invention, sensing devices also are described in U.S. Pat. Nos. 5,910,661, 5,917,605 and 5,894,351, all incorporated herein by reference.

The compounds of the present invention can also be used in an implantable device, for example to continuously monitor blood glucose levels in vivo. Suitable devices are described in, for example, co-pending U.S. Pat. Nos. 6,330,464, 5,833,603, 6,002,954 and 6,011,984, all incorporated herein by reference.

Figure 5A:
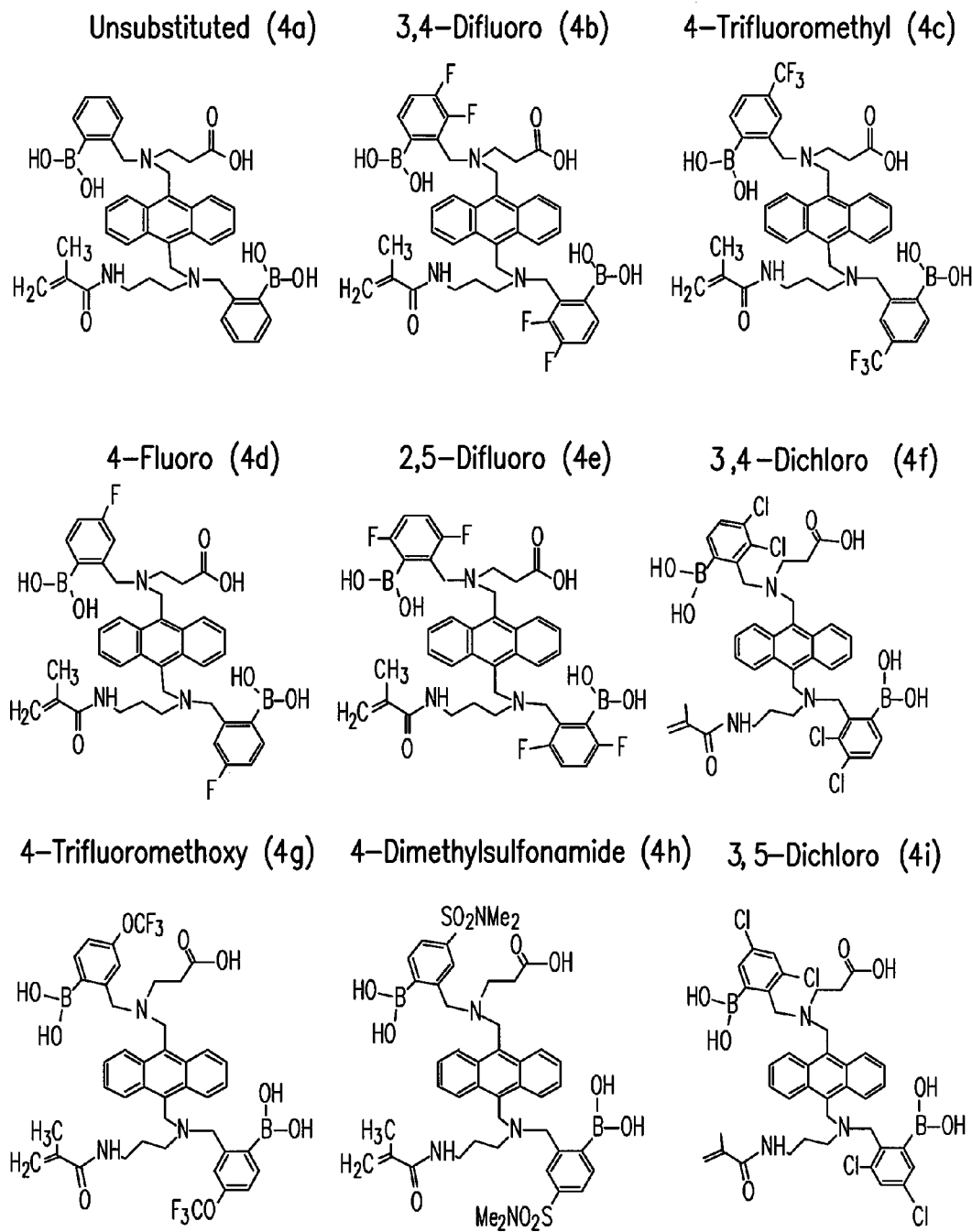
FIGS. 5A and B depict several preferred compounds of the present invention.

Particularly preferred compounds include the compounds depicted in FIGS. 5A and B (the compounds designated "Unsubstituted" and "2-Methyl" do not contain an electron withdrawing group, but are presented for illustrative purposes). The compounds are depicted in the carboxylic acid form and with the boronic acid group being unprotected. However, it will be understood that, for example, compounds having the carboxylic acid salt form and/or capped boronic acid groups are within the scope of the present invention.

The compounds of the present invention can be prepared by persons skilled in the art without an undue amount of experimentation using readily known reaction mechanisms and reagents, for example including reaction mechanisms which are consistent with the general procedures described below:

Scheme 1
Synthesis of glucose indicators from commercially available phenylboronic esters

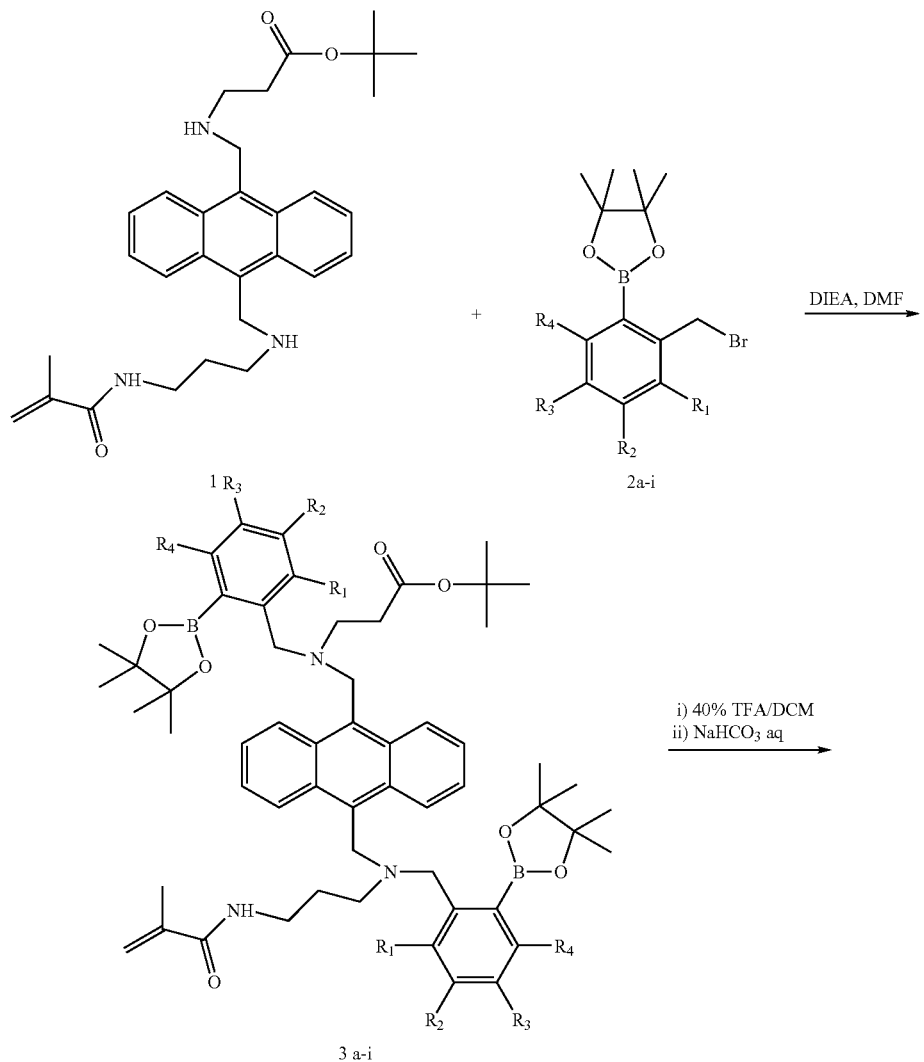

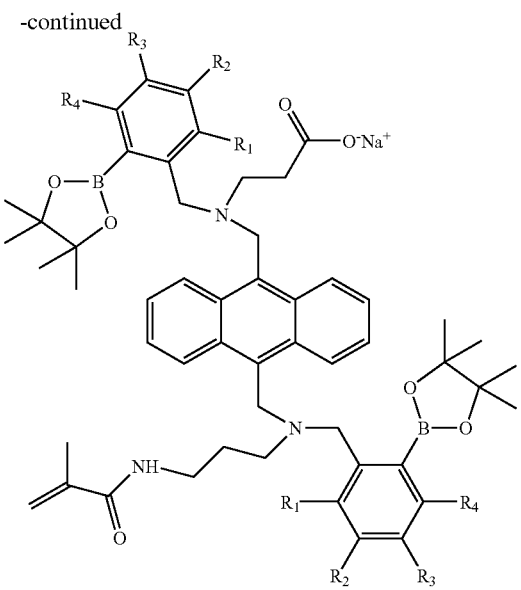
a) $R_1 = R_2 = R_3 = R_4 = H$
b) $R_1 = R_2 = F, R_3 = R_4 = H$
c) $R_1 = R_3 = R_4 = H, R_2 = CF_3$
d) $R_1 = R_3 = R_4 = H, R_2 = F$
e) $R_1 = R_4 = F, R_2 = R_3 = H$
f) $R_1 = R_2 = Cl, R_3 = R_4 = H$
g) $R_1 = R_3 = R_4 = H, R_2 = OCF_3$
h) $R_1 = R_3 = R_4 = H, R_2 = SO_2NMe_2$
i) $R_1 = R_3 = Cl, R_2 = R_4 = H$
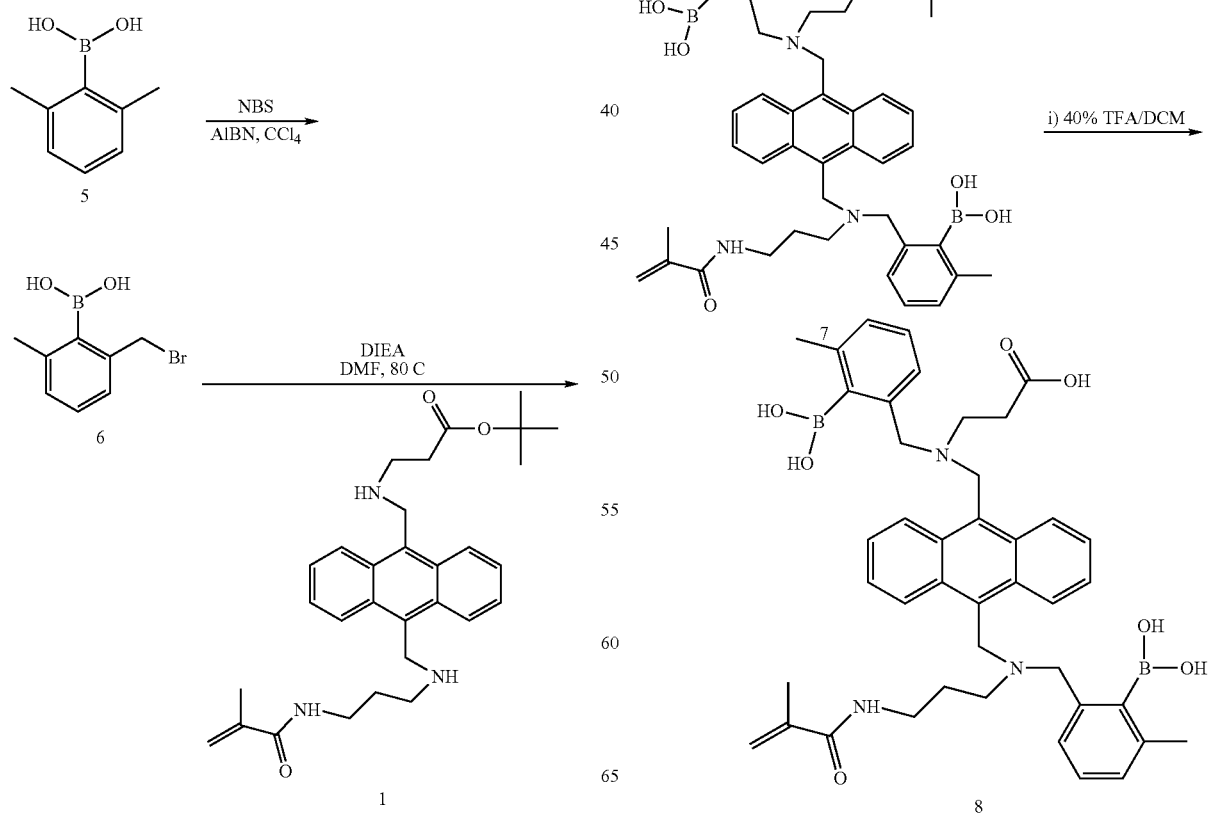

Scheme 3
Syntheses of glucose indicators from commercially available disubstituted bromobenzenes
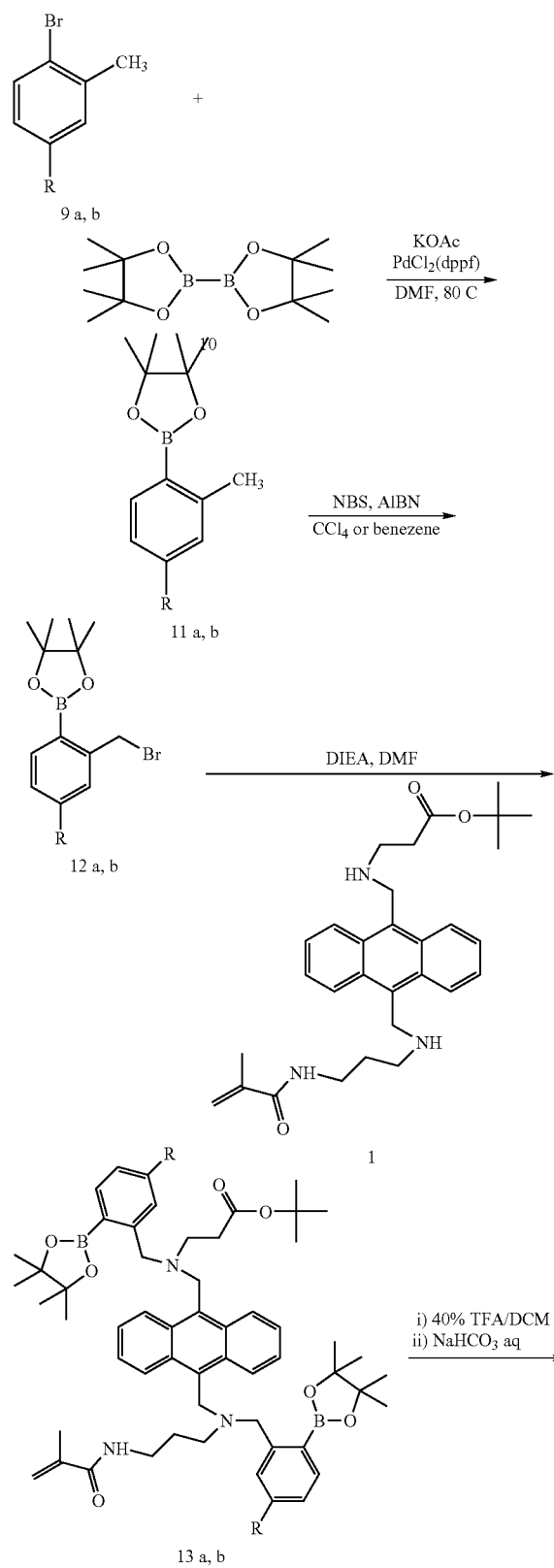
a) R = CN, b) R = NO$_2$
Scheme 4
Synthesis of glucose indicator from commercially available sulfonyl chloride
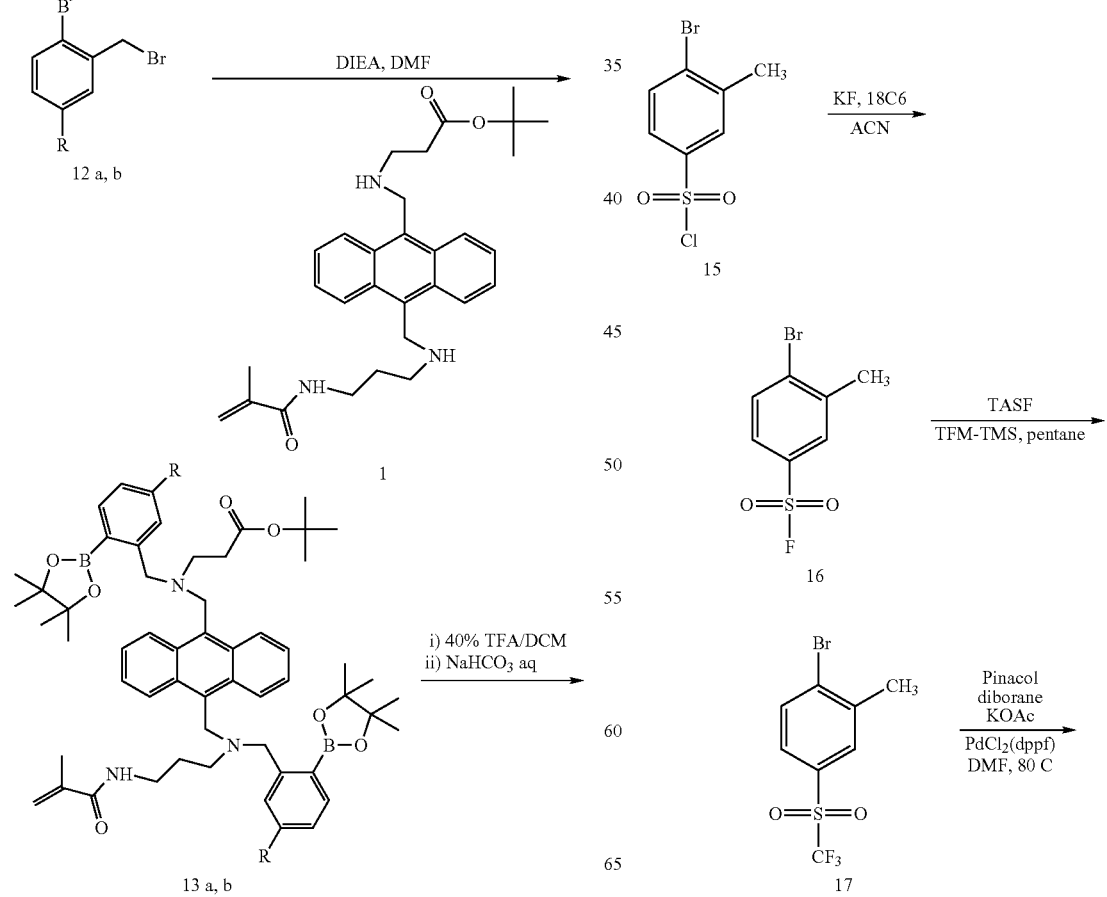

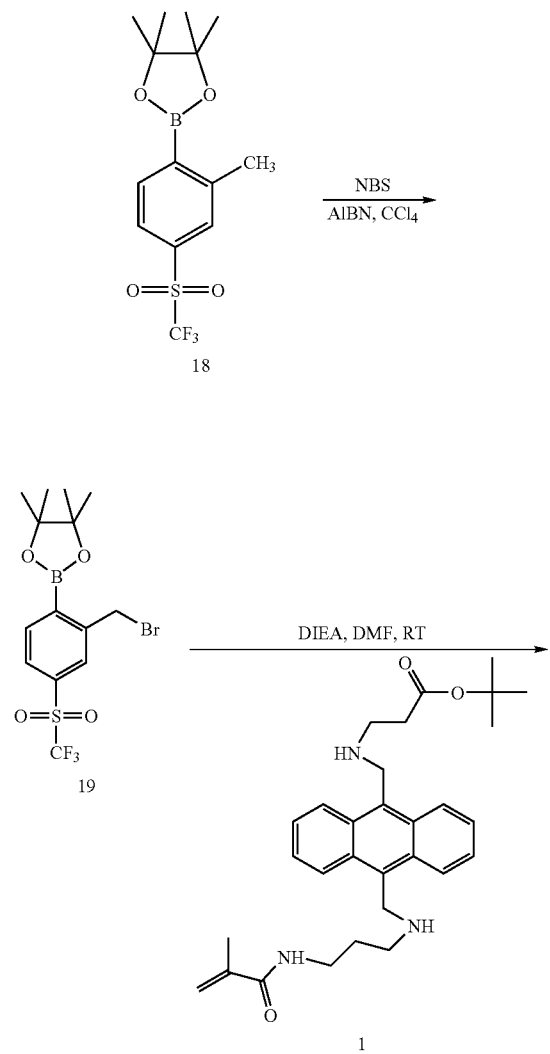
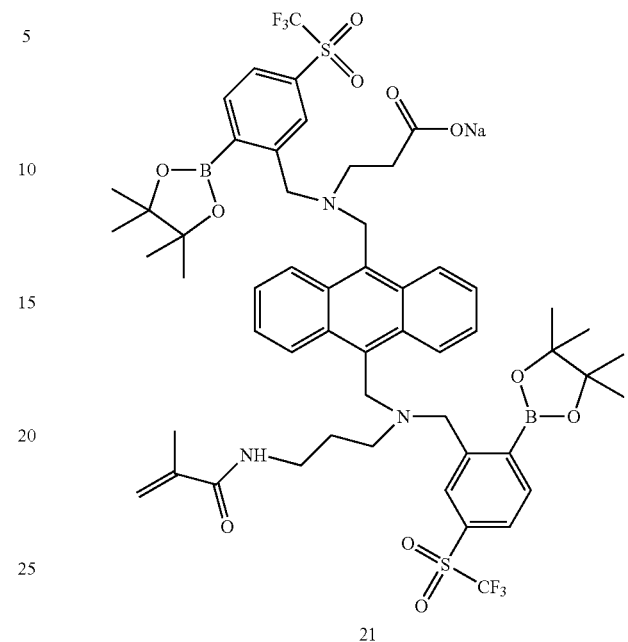
Scheme 5
Synthesis of glucose indicators from commercially available substituted toleuenes
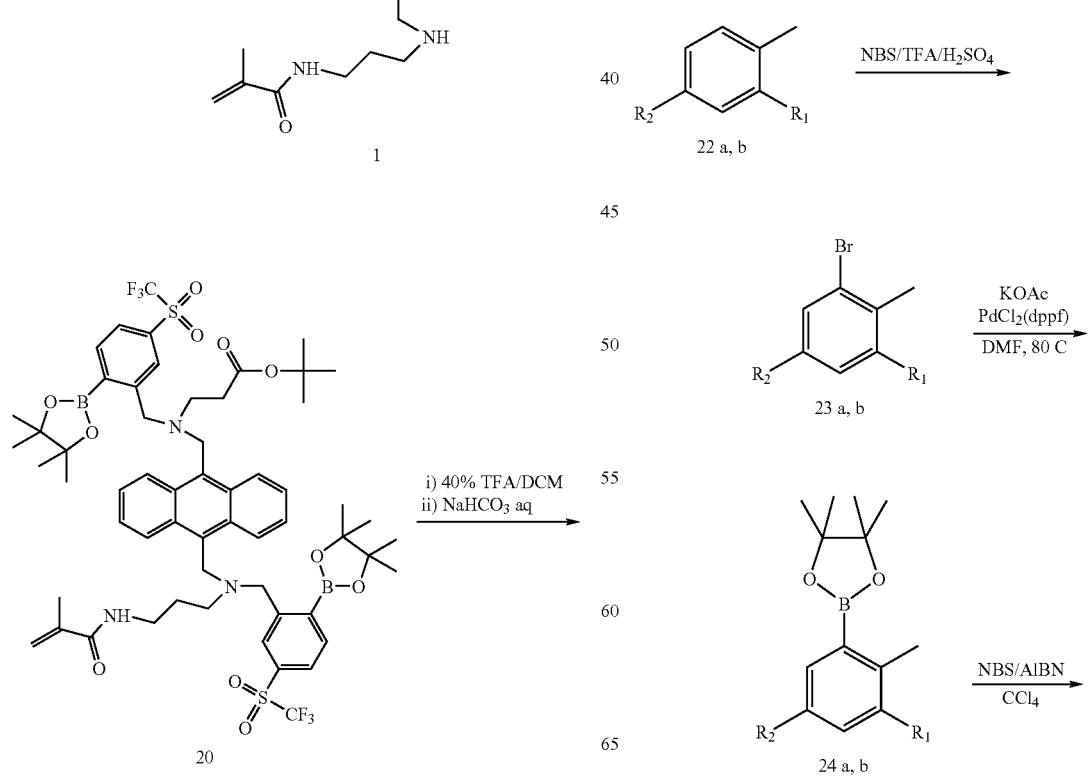

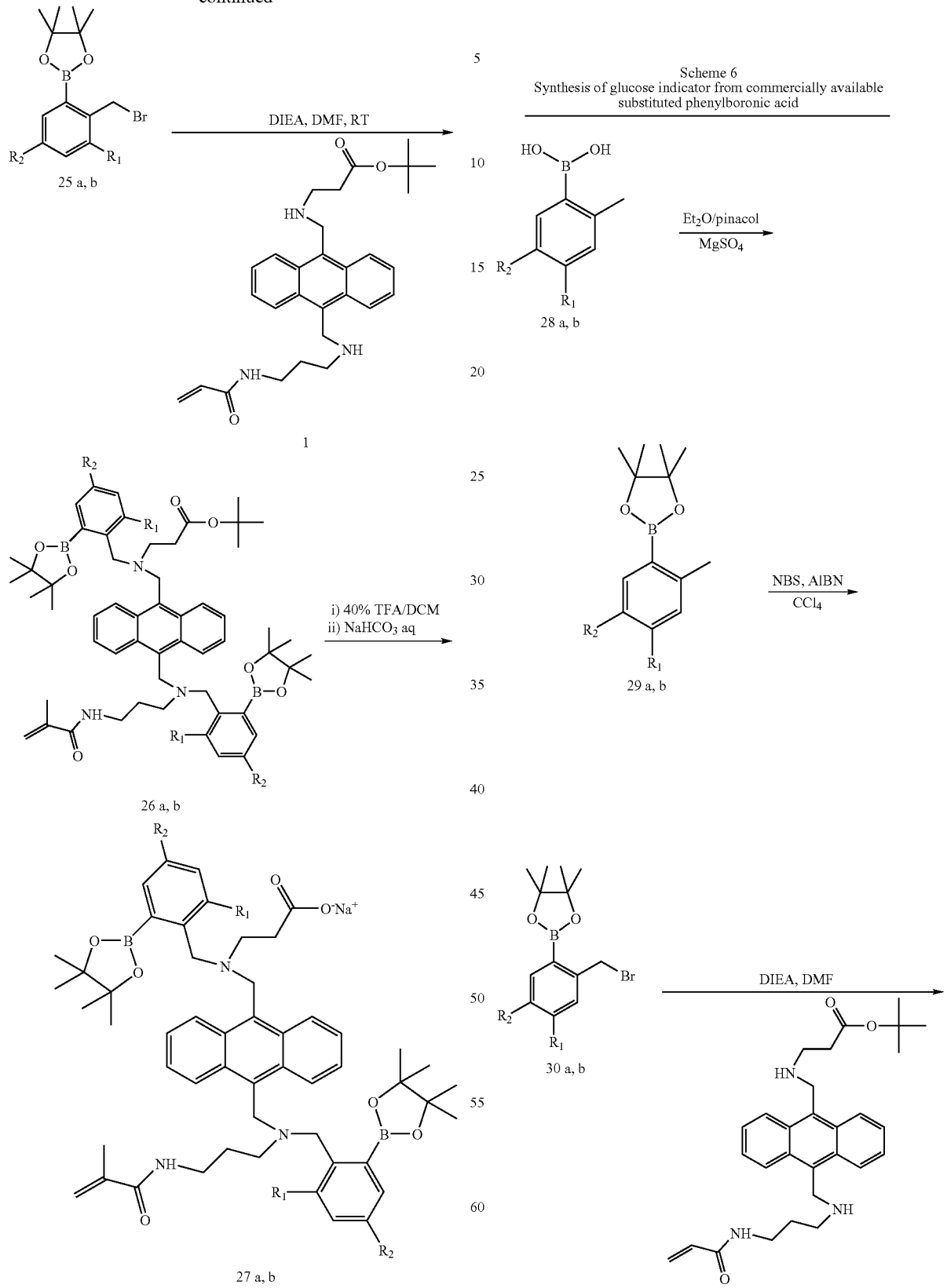

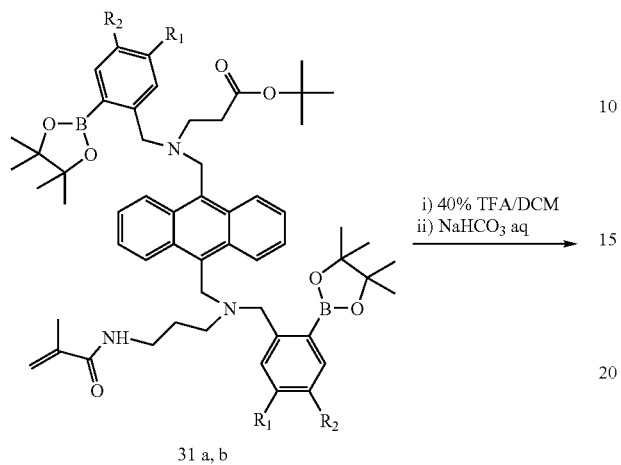
31 a, b
i) 40% TFA/DCM
ii) NaHCO₃ aq
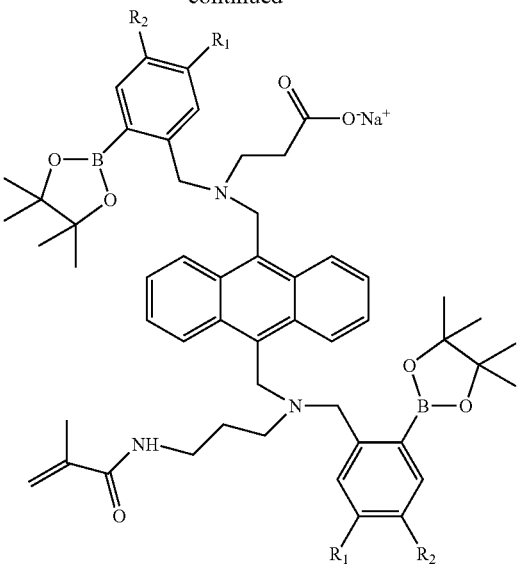
32 a, b
a) $R_1 = H, R_2 = F$
b) $R_1 = Cl, R_2 = H$
The starting compound 2 c in Scheme 1 may be prepared according to the following general synthetic routes:
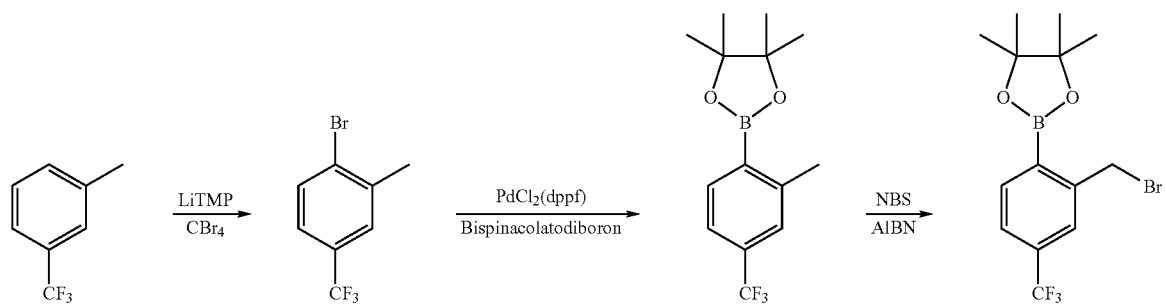
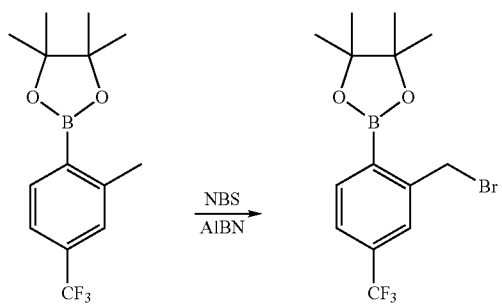

-continued

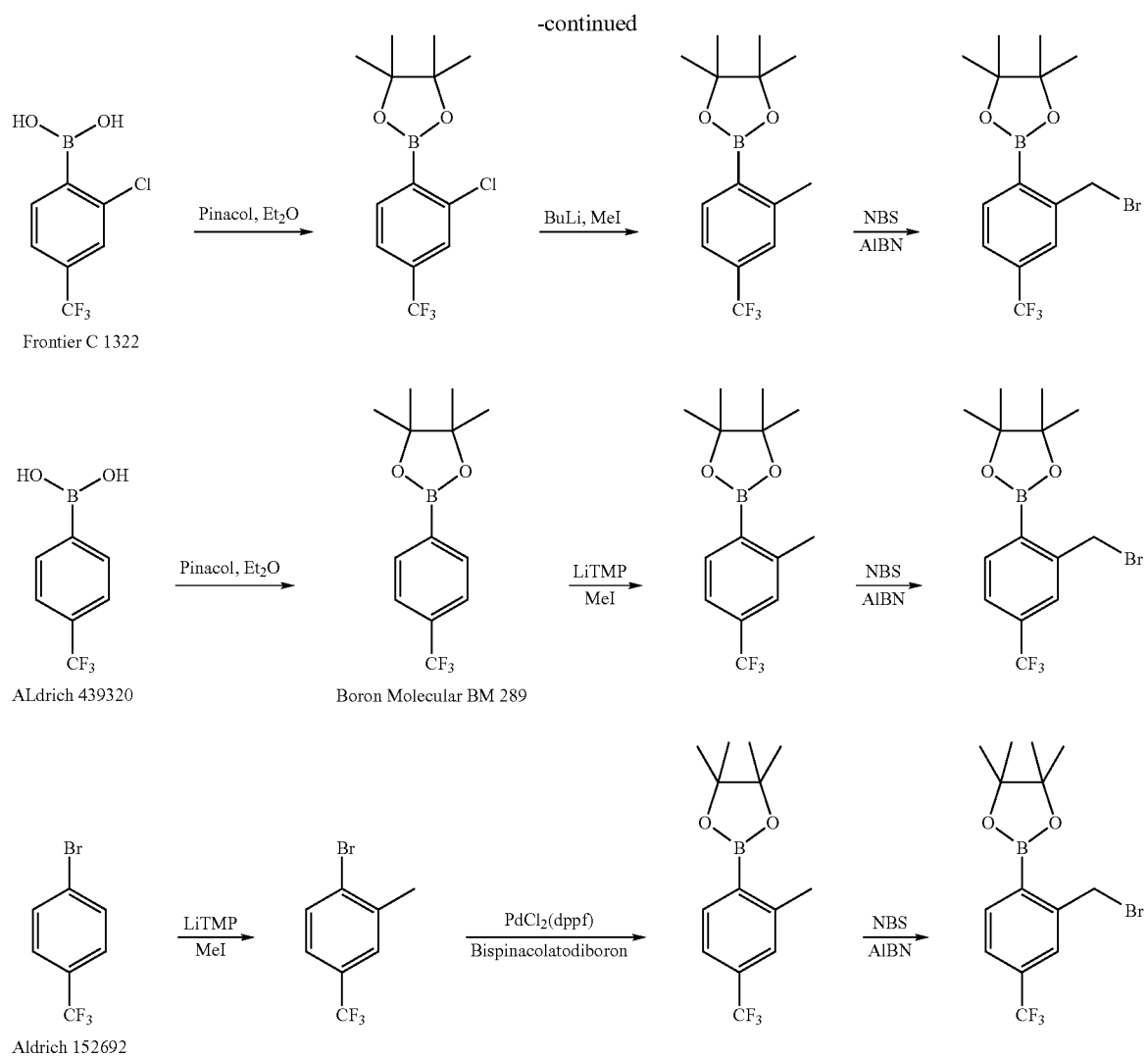

It will be understood that while the syntheses shown just above may be used to synthesize compound 2c of Scheme 1, one of ordinary skill would readily understand how to make compounds 2a-2b and 2d-2i as well, all of which are within the scope of the present invention.

EXAMPLE 1

Figure 3:
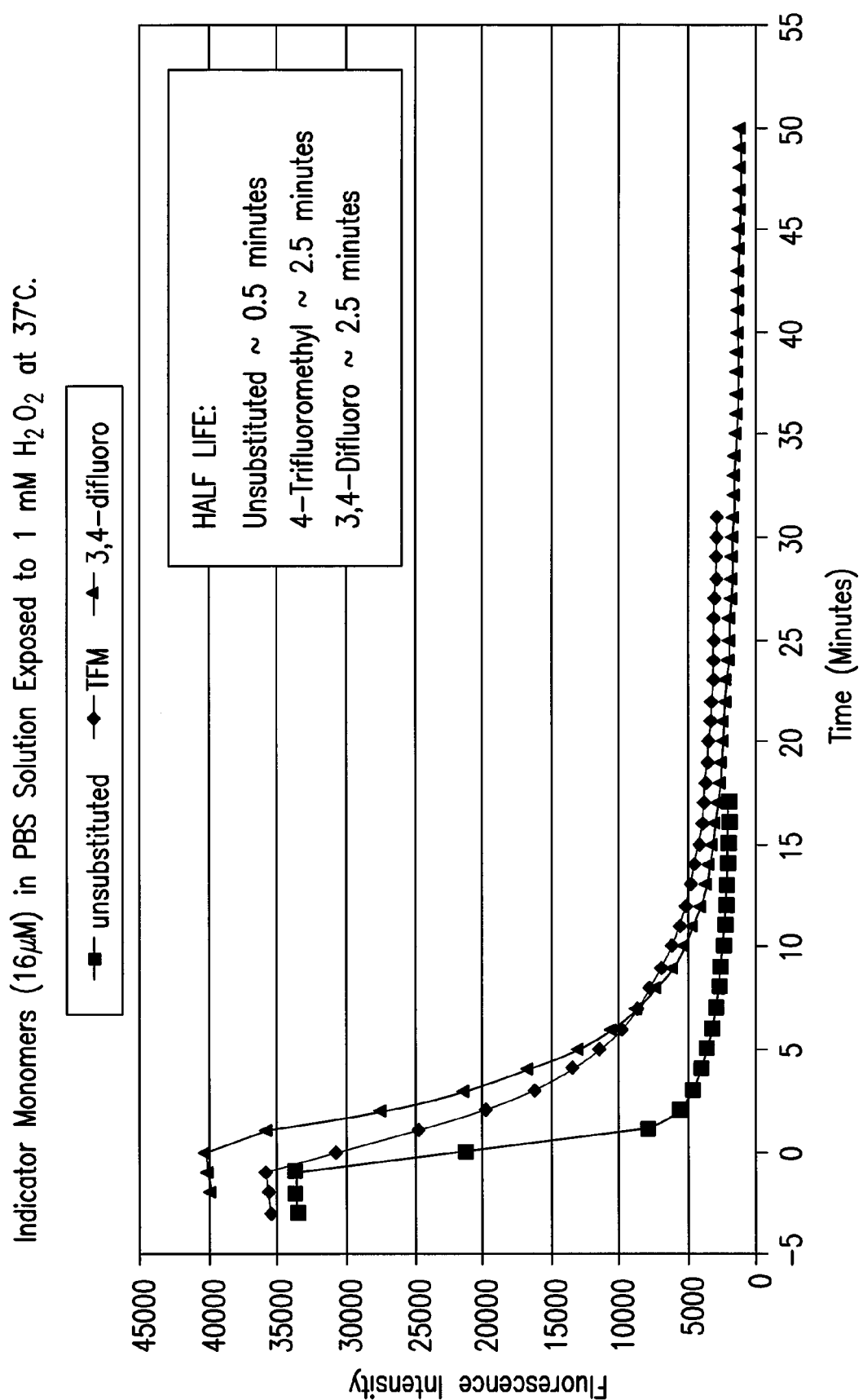
FIG. 3 illustrates the results of one of the experiments described in Example 1.

The modulation of the fluorescence of various molecules (depicted in FIG. 5) by varying concentrations of glucose was determined. The results are set forth in FIG. 1, and show that most of the molecules tested modulated well. Two of the molecules (the 4-nitro and 2-methyl substituted compounds) did not modulate well, but still are useful as oxidation-resistant tags. In a further experiment, the unsubstituted control and two compounds of the present invention (4-trifluoromethyl and 3,4-difluoro) were subjected to oxidation treatment with 1 mM hydrogen peroxide, and the loss of fluorescence intensity was measured. Those data are shown in FIG. 3.

EXAMPLE 2

Figure 2:
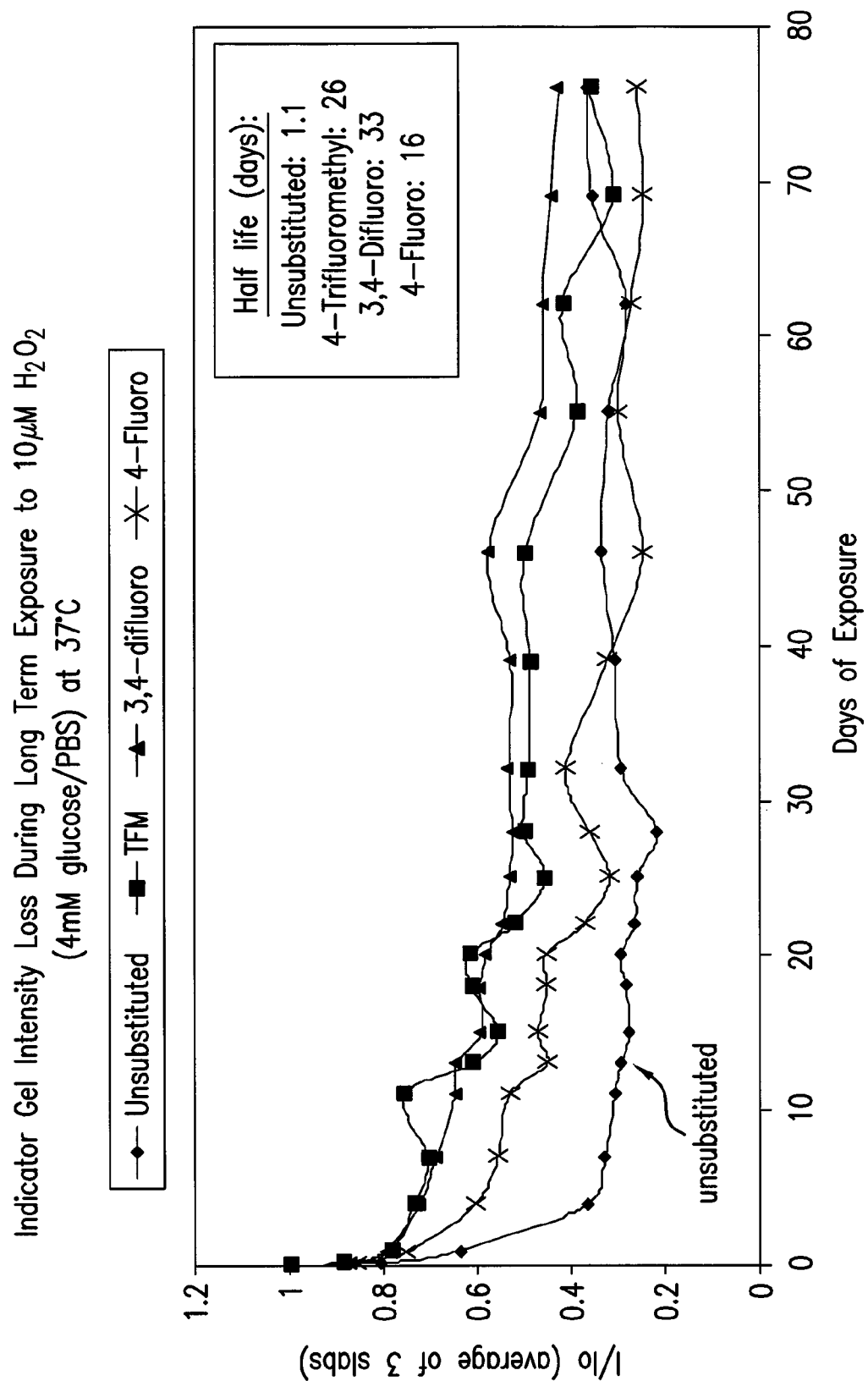
FIG. 2 illustrates the results of one of the experiments described in Example 2.

Several gels (produced as in Example 3) containing compounds of the present invention (4-trifluoromethyl, 3,4-difluoro and 4-fluoro) and a control (unsubstituted) were subjected to long term exposure to 10 μM hydrogen peroxide and 4 mM glucose/PBS at 37° C., and the loss of fluorescence intensity was measured. Those data are shown in FIG. 2. In addition, the measured in vitro half life data for three of the compounds are set forth in Table 1 below.

The data in the table show that, as compared with the standard unsubstituted monomer, the 3,4-difluoro and the 4-trifluoromethyl analogs have approximately 33 and 26 times longer half life, respectively, in the presence of 10 μM hydrogen peroxide. For comparison, literature reports that typical physiological hydrogen peroxide levels are approximately 0.5 μM maximum. Also notable from the table are the differences in average fluorescence intensity. Both analogs show lower overall modulation, but substantially greater fluorescence (are brighter) and thus provide a stronger signal, raising the signal to noise ratio and therefore greater resolution in a sensor product as a side benefit. The lower Kd measured for the 4-trifluoromethyl indicator is superior to the standard control for the purpose of human glucose sensing, because it has greater sensitivity to glucose in the physiological range.

TABLE 1

| INDICATOR | AVERAGE FLUORESCENCE INTENSITY | AVERAGE % MODULATION (0 to 20 mM glucose) | Average t90 | Kd for Glucose (37° C.) | HALF LIFE (days) at 37° C. in 4 mM glucose and 10 μM $H_2O_2$ |
|---|---|---|---|---|---|
| Unsubstituted | 9198 | 248 | 4-5 | 19.1 | 1.1 |
| 3,4-Difluoro | 12690 | 137 | 3-4 | 30.9 | 33 |
| 4-Trifluoromethyl | 14921 | 191 | 4-5 | 12.2 | 26 |

EXAMPLE 3

Figure 4:
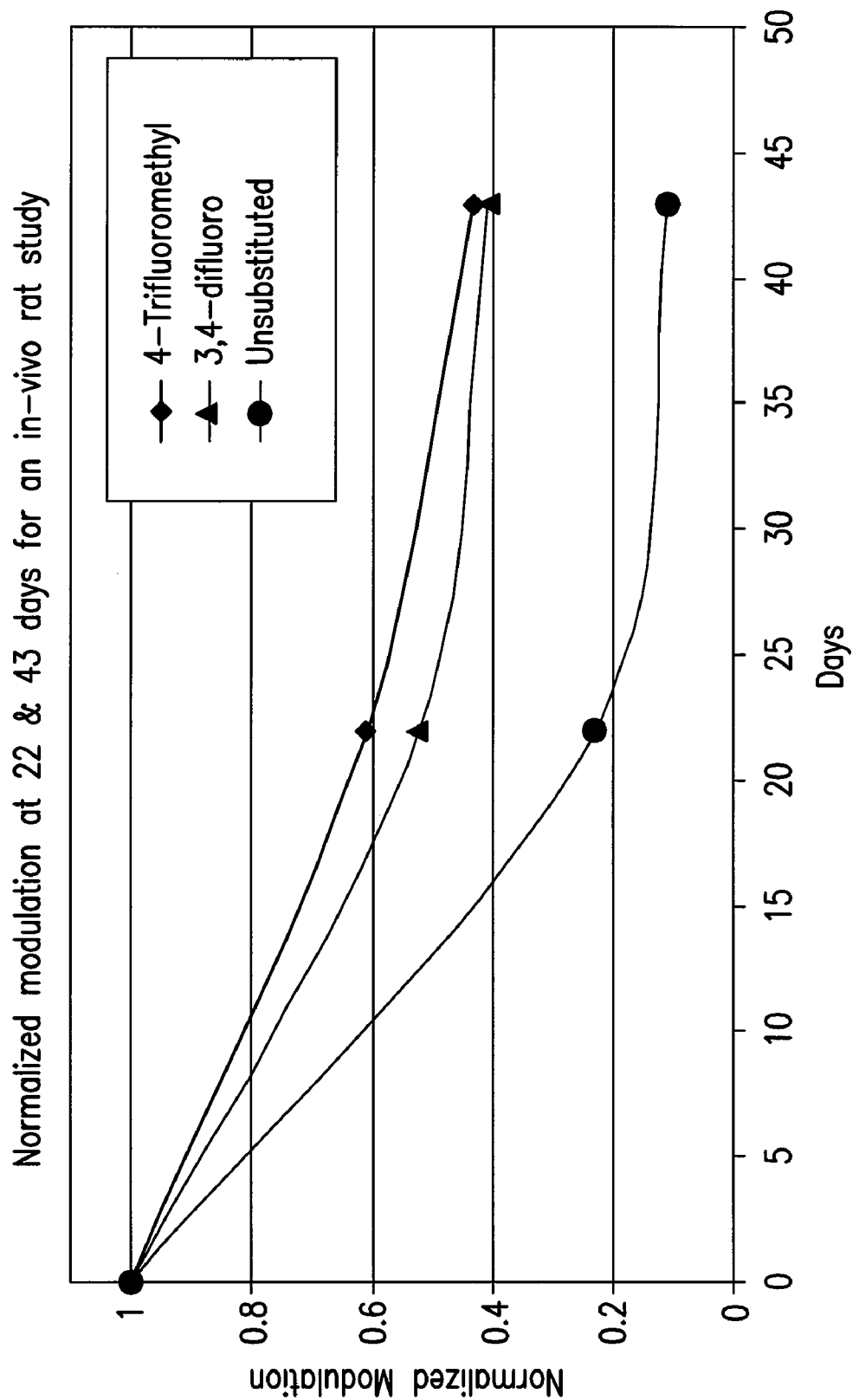
FIG. 4 illustrates the results of the experiment described in Example 3.

Two compounds according to the present invention (4-trifluoromethyl and 3,4-difluoro) and the unsubstituted control were each copolymerized with hydroxyethyl methacrylate (HEMA) and acrylic acid, and crosslinked with ethylene glycol dimethacrylate (EGDMA) to form a water insoluble polymer graft, which was then implanted into a rat to be subjected to in vivo oxidation for 22 or 43 days. Upon explant, the fluorescence of each compound was measured, and the data are shown in FIG. 4. The compounds of the present invention retained greater fluorescence compared to the control.

EXAMPLE 4

Figure 6:
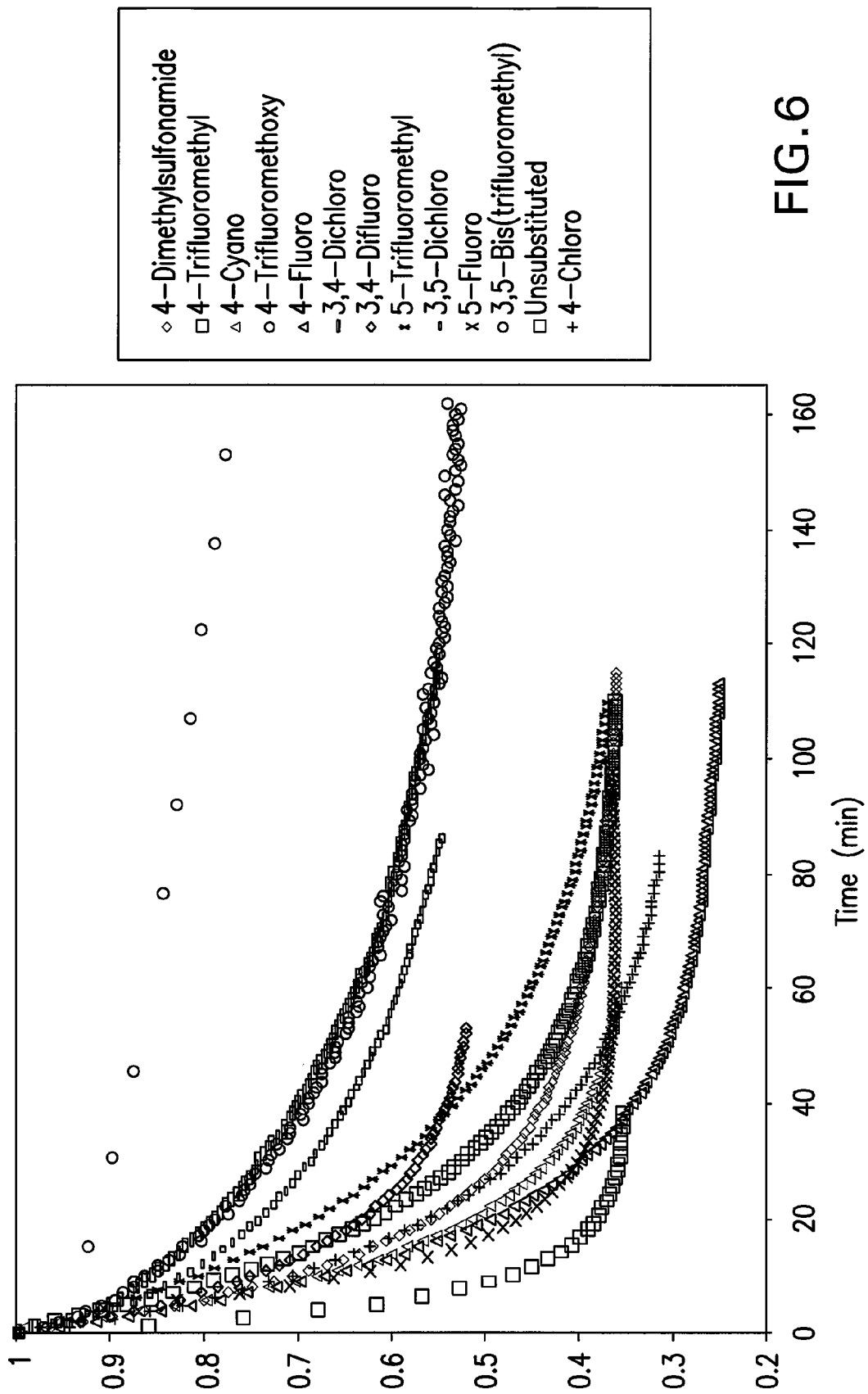
FIG. 6 illustrates the results of one of the experiments described in Example 4.
Figure 7:
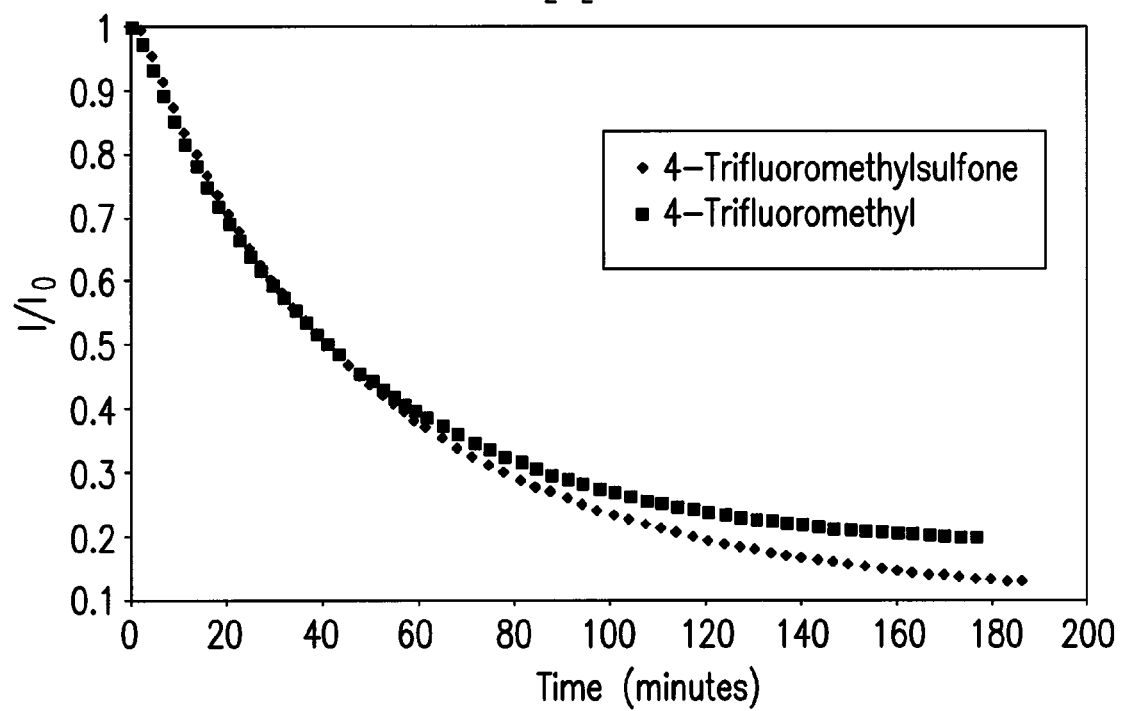
FIG. 7 illustrates the results of another experiment described in Example 4.
Figure 8:
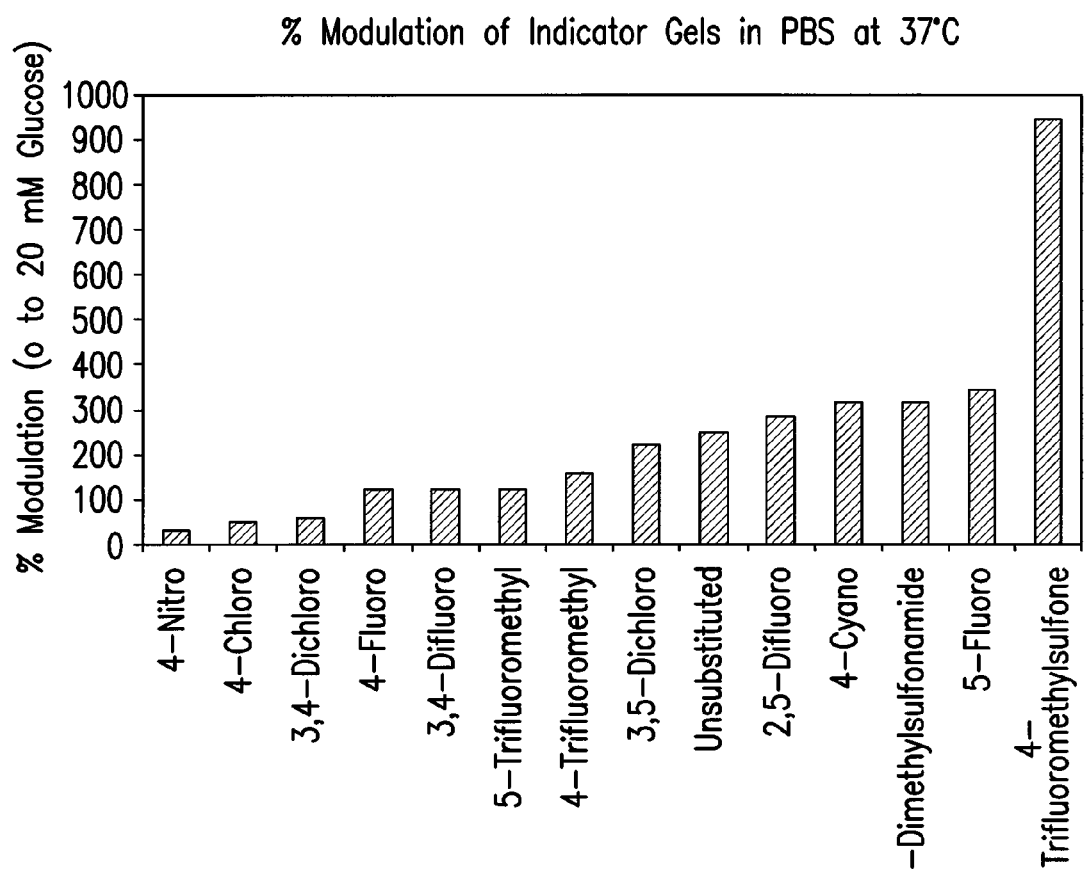
FIG. 8 illustrates the results of another experiment described in Example 4.

Several compounds of the present invention were each copolymerized with hydroxyethyl methacrylate (HEMA), acrylic acid and ethylene glycol dimethacrylate (EGDMA) to form water insoluble polymer gels, as in Example 3. Their stability towards oxidant was assessed by subjecting the gels to 1 mM hydrogen peroxide in PBS at 37° C. Those data are shown in FIG. 6. In a further experiment, two of the indicator gels (the 4-trifluoromethyl and 4-trifluoromethylsulfone gels) were subjected to 1 mM hydrogen peroxide in the presence of 4 mM glucose in PBS at 37° C. Those data are shown in FIG. 7. Half-lives calculated from the two aforementioned stability experiments are set forth in Table 2. In a further experiment, the fluorescent change (% modulation) from 0 to 20 mM glucose of various indicator gels was measured and the results are shown in FIG. 8.

TABLE 2

| Indicator Gel | $t_{1/2}$ (minutes) | $t_{1/2}$ Normalized to Unsubstituted |
|---|---|---|
| Unsubstituted | 4 | 1 |
| 5-Fluoro | 6 | 1.5 |
| 4-Dimethylsulfonamide | 9 | 2.2 |
| 3,4-difluoro | 13 | 3.2 |
| 4-Fluoro | 13 | 3.2 |
| 4-Chloro | 15 | 3.8 |
| 4-Trifluoromethyl | 17 (30*) | 4.2 |
| 4-Cyano | 18 | 4.5 |
| 4-Trifluoromethylsulfone | (35*) | |
| 3,5-Dichloro | 22 | 5.5 |
| 5-Trifluoromethyl | 24 | 6.0 |
| 4-Trifluoromethoxy | 24 | 6.0 |
| 3,4-Dichloro | 32 | 8.0 |
| 3,5-Bis(trifluoromethyl) | 495 | 124.0 |

*In 4 mM Glucose Solution

EXAMPLE 5

Synthesis of 3,4-difluoro Indicator

9-[N-[6-(4,4,5,5,-tetramethyl-1,3,2-dioxaborolano)-2,3-difluorobenzyl]-N-[3-(methacrylamido)propylamino]methyl]-10-[N-[6-(4,4,5,5,-tetramethyl-1,3,2-dioxaborolano)-2,3-difluorobenzyl]-N-[2-(carboxyethyl)amino]methyl]anthracene sodium salt (4b).

Step 1

9-[N-[6-(4,4,5,5,-tetramethyl-1,3,2-dioxaborolano)-2,3-difluorobenzyl]-N-[3-(metha-crylamido)propylamino]methyl]-10-[N-[6-(4,4,5,5,-tetramethyl-1,3,2-dioxaborolano)-2,3-difluorobenzyl]-N-[2-(tert-butoxycarbonyl)ethylamino]methyl]anthracene (3b):

9-[N-[3-(methacrylamido)propylamino]methyl]-10-[N-[2-(tert-butoxycarbonyl)ethylamino]methyl]-anthracene (1, 2.40 g, 4.91 mmol) was placed into 150 mL round-bottom flask and stirred in 19 mL dimethylformamide until dissolved. 2-(Bromomethyl)-3,4-difluorophenylboronic acid pinacol ester (2b, 4.90, 14.7 mmol, 3 equiv.) and DIEA (6.8 mL, 39 mmol, 8.0 eq) were added and stirred under Argon stream until everything dissolved then heated to 80° C. in an oil bath and under a stream of Argon for 3 hours. The DMF was removed under vacuum, ether (200 mL) added and washed with phosphate buffer (100 mL of 0.1 M, pH 7.0). The aqueous solution was backwashed with ether (2×100 mL) and the combined ether solutions were dried over $Na_2SO_4$. The ether was removed under vacuum and the resulting yellow powder triturated with hexanes (100 mL) for 15 minutes. Trituration of the crude product (2.60 g) with boiling 80/20 ethyl acetate/IPA yielded an off-white powder of ~98% purity by HPLC. Crude samples were combined and recrystallized by suspending in boiling 80/20 ethyl acetate/IPA and adding ethyl acetate until all solid dissolved. Upon cooling, pure product crystallized as an off-white powder (1.54 g, 32% yield).

RP-HPLC Conditions: HP 1100 HPLC chromatography Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 16.4 min.

Step 2

9-[N-[6-(4,4,5,5,-tetramethyl-1,3,2-dioxaborolano)-2,3-difluorobenzyl]-N-[3-(methacrylamido)propylamino]methyl]-10-[N-[6-(4,4,5,5,-tetramethyl-1,3,2-dioxaborolano)-2,3-difluorobenzyl]-N-[2-(carboxyethyl)amino]methyl]anthracene sodium salt (4b)

9-[N-[6-(4,4,5,5,-tetramethyl-1,3,2-dioxaborolano)-2,3-difluorobenzyl]-N-[3-(metha-crylamido)propylamino]methyl]-10-[N-[6-(4,4,5,5,-tetramethyl-1,3,2-dioxaborolano)-2,3-difluorobenzyl]-N-[2-(tert-butoxycarbonyl)ethylamino]methyl]anthracene (3b, 1.50 g, 1.51 mmol) was placed into a 100 mL round bottom flask and dissolved in 10 mL of a 60:40 $CH_2Cl_2$:TFA solution. The reaction mixture was allowed to stir at ambient temperature for up to 2 days or until HPLC analysis showed less than 1% of starting material remained. The solvents were removed under vacuum. The residual product was dissolved in 30 mL of $CH_2Cl_2$ followed by removal of the solvent under vacuum. The dichloromethane dissolution/evaporation treatments were repeated until the product became a yellow powder. The powder was dissolved in 60 mL of dichloromethane and added dropwise into 250 mL cold saturated aqueous $NaHCO_3$ at a rate such that the temperature stayed below 5° C. The solution was stirred for an additional 5 min at <5° C. followed by partitioning of the layers. The organic layer was dried over anhydrous $Na_2SO_4$, filtered and concentrated yielding 1.21 g yellow powder. The crude product was dissolved in 30 mL of anhydrous $CH_2Cl_2$ and transfered to a 100 mL round bottom flask. PS-DEAM beads (0.38 g) were added to the flask and the reaction mixture was shaken at ambient temperature for 16 h. The beads were filtered and washed with 5 mL dichloromethane. The combined organic solutions were concentrated under vacuum. Pure product (0.979 g, 68%) was obtained as a yellow powder.

Structure Determination:

RP-HPLC conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 14.1 min.

$^1$H NMR (400 MHz, $CDCl_3$): δ 1.32 (s, 12H), 1.33 (s, 12H) 1.50 (m, 5H, O=C—C($CH_2$)$CH_3$), N—$CH_2CH_2CH_2$—N), 2.33 (t, 2H), 2.38 (t, 2H), 2.78 (m, 2H), 2.83 (m, 2H), 4.21 (s, 2H), 4.41 (s, 4H), 4.60 (s, 2H), 4.90 (t, 1H, C=$CH_2$), 4.95 (s, 1H, C=$CH_2$), 5.25 (br, 1H, NH), 7.15-7.25 (m, 1H, ArH), 7.28-7.32 (m, 1H), 7.35 (m, 4H, ArH), 7.68 (dd, 1H, ArH), 7.82 (dd, 1H, ArH), 7.8 (d, 2H, ArH), 8.20 (d, 2H, ArH).

ESI-MS (TFA/acetonitrile/water): 720.3 (M−3$H_2$O+H)$^+$, 738.3 (M−2$H_2$O+H)$^+$, 756.4 (M−$H_2$O+H)$^+$, 794.2 (M+Na)$^+$ for the bis-boronic acid. Boronic esters are not observed under the acidic conditions of this analysis.

EXAMPLE 6

Synthesis of 4-Trifluoromethyl Indicator

9-[N-[6-(4,4,5,5,-tetramethyl-1,3,2-dioxaborolano)-3-(trifluoromethyl)benzyl]-N-[3-(methacrylamido)propylamino]methyl]-10-[N-[6-(4,4,5,5,-tetramethyl-1,3,2-dioxaborolano)-3-(trifluoromethyl)benzyl]-N-[2-(carboxyethyl)amino]methyl]anthracene sodium salt (4c).

Step 1

9-[N-[6-(4,4,5,5,-tetramethyl-1,3,2-dioxaborolano)-3-(trifluoromethyl)benzyl]-N-[3-(methacrylamido)propylamino]methyl]-10-[N-[6-(4,4,5,5,-tetramethyl-1,3,2-dioxaborolano)-3-(trifluoromethyl)benzyl]-N-[2-(tert-butoxycarbonyl)ethylamino]methyl] anthracene (3c)

9-[N-[3-(methacrylamido)propylamino]methyl]-10-[N-[2-(tert-butoxycarbonyl)ethylamino]methyl]-anthracene (1, 2.10 g, 4.29 mmol) was placed into 250 mL round-bottom flask. It was dissolved in 5 mL of degassed dimethylformamide. 2-(Bromomethyl)-4-(trifluoromethyl)phenylboronic acid pinacol ester (2c, 3.80, 10.4 mmol, 2.4 equiv.) was dissolved in 4 mL of $N_2$ sparged DMF and added to reaction flask. The solution was stirred and flushed with $N_2$ for 5 minutes. DIEA (6.0 mL, 34 mmol, 8.0 equiv.) was added to the reaction mixture and the solution was allowed to stir under a gentle stream of nitrogen and in the dark at ambient temperature over 2 nights. After 48 h the solvent was evaporated in vacuo. The residual product was dissolved in 100 mL of dichloromethane and extracted with 2×50 mL portions of phosphate buffer (0.1 M, pH 7.0). The dichloromethane solution was dried and evaporated in vacuo resulting in a golden oily residue. The crude product was stirred for 15-30 minutes with 10 mL of hexane until yellow precipitate occurred. It was filtered and the weight of the product was determined (~3.5 g of yellow powder). The crude product was purified by multiple crystallizations from hot 2-propanol (<2 mL of IPA per gram of compound). Pure product (3c) was collected (~1.5 g).

Structure Determination:

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 17.8 min.

$^1$H NMR (400 MHz, $CDCl_3$): δ 1.25 (s, 9H, C($CH_3$)$_3$), 1.32 (s, 12H, O—C($CH_3$)$_2$C($CH_3$)$_2$,C—O), 1.35 (s, 12H, O—C($CH_3$)$_2$C($CH_3$)$_2$,C—O), 1.46 (s, 3H, O=C—C($CH_2$)$CH_3$), 1.65 (m, 2H, N—$CH_2CH_2CH_2$—N), 2.43 (t, 2H), 2.52 (t, 2H), 2.88 (t, 2H), 3.04 (m, 2H), 3.98 (s, 2H), 4.05 (s, 2H), 4.42 (s, 2H), 4.45 (s, 2H), 4.82 (s, 1H), 4.88-4.90 (br, 2H, NH overlap with CH), 7.38-7.42 (m, 5H, ArH), 7.50 (d, 1H, ArH), 7.63 (s, 1H, ArH), 7.80 (m, 2H, ArH), 7.89 (d, 1H, ArH), 8.32 (m, 4H, ArH).

ESI-MS (TFA/acetonitrile/water): 858.4 (M−2$H_2$O+H)$^+$, 876.3 (M−$H_2$O+H)$^+$ for the bis-boronic acid. Boronic esters are not observed under the acidic conditions of this analysis.

Step 2

9-[N-[6-(4,4,5,5,-tetramethyl-1,3,2-dioxaborolano)-3-(trifluoromethyl)benzyl]-N-[3-(methacrylamido)propyl amino]methyl]-10-[N-[6-(4,4,5,5,-tetramethyl-1,3,2-dioxaborolano)-3-(trifluoromethyl)benzyl]-N-[2-(carboxyethyl)amino]methyl]anthracene sodium salt (4c)

9-[N-[6-(4,4,5,5,-tetramethyl-1,3,2-dioxaborolano)-3-(trifluoromethyl)benzyl]-N-[3-(methacryl-amido)propylamino]methyl]-10-[N-[6-(4,4,5,5,-tetramethyl-1,3,2-dioxaborolano)-3-(trifluoro-methyl)benzyl]-N-[2-(tert-butoxycarbonyl)ethylamino]methyl]anthracene (3c, 1.037 g, 0.980 mmol) was placed into a 250 mL round bottom flask and dissolved in 10 mL of a 60:40 degassed $CH_2Cl_2$:TFA solution. The reaction mixture was allowed to stir at ambient temperature for 24-48 h or until HPLC analysis showed less than 1% of starting material remained. The residual product was washed with 30 mL of $CH_2Cl_2$ followed by removal of the solvent under vacuum. The dichloromethane washes were repeated until the product became a yellow powder. The powder was dissolved in 60 mL of dichloromethane and added dropwise into 240 mL cold saturated aqueous $NaHCO_3$ at a rate such that the temperature stayed below 5° C. The solution was stirred for an additional 5 min at <5° C. followed by partitioning of the layers. The organic extracts were dried over anhydrous $Na_2SO_4$, filtered and concentrated yielding 1 g yellow powder. The crude product was dissolved in 10 mL of anhydrous $CH_2Cl_2$ and transfered to a 100 mL round bottom flask. PS-DEAM beads (0.55 g, 1 mmol, 1 eq) were added to the flask and the reaction mixture was flushed with nitrogen for 2 minutes. The solution was shaken at ambient temperature for 16 h. The beads were filtered and washed with 2×10 mL dichloromethane. The combined organic solutions were concentrated under vacuum. Pure product (4c) was obtained (0.603 g, 60% of indicator).

Structure Determination:

mp: 91-95° C. (uncorrected)

RP-HPLC conditions: HP 1100 HPLC chromatograph, Waters 4.6×100 mm Symmetry 3.5μ C18 column (with Sentry C18 guard column), 0.010 mL injection (sample dissolved in 70/30 water/MeCN with 1% v/v TFA), 0.100 mL injection loop, 0.75 mL/min, 254 nm detection, A=water (0.1% TFA) and B=MeCN (0.1% v/v TFA), gradient 10% B 2 min, 10-80% B over 18 min, 80-100% B over 2 min, 100% B 2 min, retention time 14.9 min.

$^1$H NMR (400 MHz, $CDCl_3$): δ 1.34 (s, 12H), 1.38 (s, 12H) 1.58-1.60 (m, 5H, O=C—C(CH$_2$)CH$_3$), N—CH$_2$CH$_2$CH$_2$—N), 2.31 (t, 2H), 2.44 (t, 2H), 2.87 (m, 2H), 2.92 (m, 2H), 4.05 (s, 2H), 4.35 (s, 2H), 4.44 (s, 2H), 4.55 (s, 2H), 4.95 (t, 1H, C=CH$_2$), 5.05 (s, 1H, C=CH$_2$), 5.3-5.4 (br, 1H, NH), 7.38-7.42 (m, 4H, ArH), 7.52 (d, 1H, ArH), 7.68 (d, 1H, ArH), 7.80 (br s, 1H, ArH), 7.85-7.90 (m, 3H, ArH), 7.91 (d, 1H, ArH), 8.12 (d, 1H, ArH), 8.28 (d, 2H, ArH).

ESI-MS (TFA/acetonitrile/water): 802.4 $(M-2H_2O+H)^+$, 820.3 $(M-H_2O+H)^+$, 838.4 $(M+H)^+$ for the bis-boronic acid. Boronic esters are not observed under the acidic conditions of this analysis.

EXAMPLE 7

Synthesis of 4-Fluoro Indicator

9-[N-[6-(4,4,5,5,-tetramethyl-1,3,2-dioxaborolano)-3-fluorobenzyl]-N-[3-(methacrylamido)propylamino]methyl]-10-[N-[6-(4,4,5,5,-tetramethyl-1,3,2-dioxaborolano)-3-fluorobenzyl]-N-[2-(carboxyethyl)amino]methyl]anthracene sodium salt (4d).

Step 1

9-[N-[6-(4,4,5,5,-tetramethyl-1,3,2-dioxaborolano)-3-fluorobenzyl]-N-[3-(metha-crylamido)propylamino]methyl]-10-[N-[6-(4,4,5,5,-tetramethyl-1,3,2-dioxaborolano)-3-fluorobenzyl]-N-[2-(tert-butoxycarbonyl)ethylamino]methyl]anthracene (3d):

9-[N-[3-(methacrylamido)propylamino]methyl]-10-[N-[2-(tert-butoxycarbonyl)ethylamino]methyl]-anthracene (1, 718 g, 1.47 mmol) was stirred in 5 mL dimethylformamide until dissolved. 2-(Bromomethyl)-4-fluorophenylboronic acid pinacol ester (2d, 1.85 g, 5.87 mmol, 4 eq) and DIEA (1.52 g, 12 mmol, 8.0 eq) were added and heated to 80° C. for 18 hours. Ether (100 mL) was then added and the solution washed with phosphate buffer (3×100 mL of 0.1 M, pH 7.0). The organic solution was dried over $Na_2SO_4$ then removed under vacuum. The crude product was triturated with hexanes (2×50 mL) then recrystallized from 25 mL of boiling 80/20 ethyl acetate/IPA which yielded an off-white powder (0.52 g, 37%).

Structure Determination:

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 15.7 min.

$^1$H NMR (400 MHz, $CDCl_3$): δ 1.3 (two overlapping singlets, 24H, O—C(CH$_3$)$_2$C(CH$_3$)$_2$,C—O), 1.33 (s, 9H, C(CH$_3$)$_3$), 1.52 (s, 3H), 1.55 (s, 1H), 1.70 (t, 1H), 2.48 (t, 2H), 2.55 (m, 2H), 2.82 (t, 2H), 3.08 (m, 2H), 3.85 (s, 2H), 4.05 (s, 2H), 4.45 (s, 2H), 4.55 (s, 2H), 4.82 (d, 2H), 5.05 (br, 1H), 6.83 (t, 1H). 6.84 (t, 1H), 7.08 (dd, 1H), 7.20 (dd, 1H), 7.44 (m, 4H), 7.68 (dd, 1H), 7.78 (dd, 1H), 8.36 (m, 2H), 8.45 (m, 2H).

ESI-MS: 957 $(M+H)^+$, 874.4 $(M+H)^+$ for mono boronic ester mono-acid, 792.3 $(M+H)^+$ and 774.2 $(M-H_2O+H)^+$ for bis-boronic acid. Boronic esters and acids were observed under the acidic conditions of this analysis.

Step 2

9-[N-[6-(4,4,5,5,-tetramethyl-1,3,2-dioxaborolano)-3-fluorobenzyl]-N-[3-(methacrylamido)propylamino]methyl]-10-[N-[6-(4,4,5,5,-tetramethyl-1,3,2-dioxaborolano)-3-fluorobenzyl]-N-[2-(carboxyethyl)amino]methyl]anthracene sodium salt (4d)

9-[N-[6-(4,4,5,5,-tetramethyl-1,3,2-dioxaborolano)-3-fluorobenzyl]-N-[3-(metha-crylamido)propylamino]methyl]-10-[N-[6-(4,4,5,5,-tetramethyl-1,3,2-dioxaborolano)-3-fluorobenzyl]-N-[2-(tert-butoxycarbonyl)ethylamino]methyl]anthracene (3d, 0.450 g, 0.47 mmol) was dissolved in 10 mL of a 60:40 $CH_2Cl_2$:TFA solution and stirred at ambient temperature for 16 hours. The reaction solution was diluted with dichloromethane (30 mL) then added in 3 portions into rapidly stirred ice cold saturated aqueous NaHCO$_3$. The organic layer was separated, dried over anhydrous Na$_2$SO$_4$, filtered and concentrated under vacuum yielding 0.32 g yellow powder. The crude product was dissolved in anhydrous CH$_2$Cl$_2$ and shaken over PS-DEAM beads overnight. The beads were filtered and the organic solvent removed under vacuum. Pure product (0.235 g, 55%) was obtained as a yellow powder.

Structure Determination:

RP-HPLC conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 13.7 min.

$^1$H NMR (400 MHz, CDCl$_3$): δ 1.33 (s, 12H), 1.35 (s, 12H), 1.62 (m, 5H, O=C—C(CH$_2$)CH$_3$), N—CH$_2$CH$_2$CH$_2$—N), 2.33 (t, 2H), 2.48 (t, 2H), 2.88 (m, 2H), 2.95 (m, 2H), 4.04 (s, 2H), 4.32 (s, 2H), 4.48 (s, 2H), 4.62 (s, 2H), 5.00 (t, 1H, C=CH$_2$), 5.12 (s, 1H, C=CH$_2$), 5.48 (br, 1H, NH), 6.95 (dt, 1H), 7.15 (dt, 1H), 7.22 (br, 1H), 7.30 (dd, 1H), 7.48 (m, 4H), 7.80 (dd, 1H), 7.90 (m, 2H), 8.05 (dd, 1H), 8.37 (m, 2H)

EXAMPLE 8

Synthesis of 2,5-difluoro Indicator

9-[N-[6-(4,4,5,5,-tetramethyl-1,3,2-dioxaborolano)-2,5-difluorobenzyl]-N-[3-(methacrylamido)propylamino]methyl]-10-[N-[6-(4,4,5,5,-tetramethyl-1,3,2-dioxaborolano)-2,5-(difluoro)benzyl]-N-[2-(carboxyethyl)amino]methyl]anthracene sodium salt (4e).

Step 1

9-[N-[6-(4,4,5,5,-tetramethyl-1,3,2-dioxaborolano)-2,5-difluorobenzyl]-N-[3-(metha-crylamido)propylamino]methyl]-10-[N-[6-(4,4,5,5,-tetramethyl-1,3,2-dioxaborolano)-2,5-difluorobenzyl]-N-[2-(tert-butoxycarbonyl)ethylamino]methyl]anthracene (3e):

9-[N-[3-(methacrylamido)propylamino]methyl]-10-[N-[2-(tert-butoxycarbonyl)ethylamino]methyl]-anthracene (1, 0.872 g, 1.78 mmol) was placed into 100 mL round-bottom flask and stirred in 7 mL dimethylformamide until dissolved. 6-(Bromomethyl)-2,5-difluorophenylboronic acid pinacol ester (2e, 1.49, 4.47 mmol, 2.5 equiv.) and DIEA (1.86 g, 14.4 mmol, 8.0 equiv) were added and stirred under Argon stream until everything dissolved then heated to 80° C. in an oil bath and under a stream of Argon overnight. More 6-(Bromomethyl)-2,5-difluorophenylboronic acid pinacol ester (0.300 g, 0.5 equiv.) was added and heating continued a second night. Ether (100 mL) was added to the reaction solution and washed with pH 7.0, 0.1 M phosphate buffer. The organic solution was dried over Na$_2$SO$_4$, the solvent removed under vacuum and the residue triturated with hexanes (2×50 mL). The resulting reddish-brown solid was treated with boiling hexanes (50 mL), decanted and the desired product (0.49 g) collected as white crystals from the cooled hexane.

Structure Determination:

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 15.0 min.

Step 2

9-[N-[6-(4,4,5,5,-tetramethyl-1,3,2-dioxaborolano)-2,5-difluorobenzyl]-N-[3-(methacrylamido)propylamino]methyl]-10-[N-[6-(4,4,5,5,-tetramethyl-1,3,2-dioxaborolano)-2,5-difluorobenzyl]-N-[2-(carboxyethyl)amino]methyl]anthracene sodium salt (4e)

9-[N-[6-(4,4,5,5,-tetramethyl-1,3,2-dioxaborolano)-2,5-difluorobenzyl]-N-[3-(metha-crylamido)propylamino]methyl]-10-[N-[6-(4,4,5,5,-tetramethyl-1,3,2-dioxaborolano)-2,5-difluorobenzyl]-N-[2-(tert-butoxycarbonyl)ethylamino]methyl]anthracene (3e, 0.49) was stirred in 10 mL of a 60:40 overnight by which time HPLC showed no starting material remained. The solvents were removed under vacuum, the residue dissolved in dichloromethane (3 mL) and added dropwise into rapidly stirring pentane (100 mL). The product trifluoroacetic acid salt was isolated as a yellow powder by filtration (0.40 g) and characterized by mass spectroscopy The freebased indicator was obtained as follows. The powder (0.20 g) was dissolved in 10 mL of dichloromethane and added dropwise into 100 mL cold saturated aqueous NaHCO$_3$ at a rate such that the temperature stayed below 5° C. The organic layer was separated then dried over anhydrous Na$_2$SO$_4$. PS-DEAM beads (0.5 g) were added to the flask and the suspension was shaken at ambient temperature overnight. Filtration and removal of the solvent under vacuum yielded product (95 mg) as a yellow powder.

Structure Determination:

RP-HPLC conditions: RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 12.9 min.

ESI-MS (TFA/acetonitrile/water): 720.3 (M–3H$_2$O+H)$^+$, 738.3 (M–2H$_2$O+H)$^+$, 756.4 (M–H$_2$O+H)$^+$, 778.3 (M–H$_2$O+Na)$^+$ for the bis-boronic acid. Boronic esters are not observed under the acidic conditions of this analysis.

EXAMPLE 9

Synthesis of 3,4-dichloro Indicator

9-[N-[6-(4,4,5,5,-tetramethyl-1,3,2-dioxaborolano)-2,3-dichlorobenzyl]-N-[3-(methacrylamido)propylamino]methyl]-10-[N-[6-(4,4,5,5,-tetramethyl-1,3,2-dioxaborolano)-2,3-dichlorobenzyl]-N-[2-(carboxyethyl)amino]methyl]anthracene sodium salt (4f)

Step 1

9-[N-[6-(4,4,5,5,-tetramethyl-1,3,2-dioxaborolano)-2,3-dichlorobenzyl]-N-[3-(metha-crylamido)propylamino]methyl]-10-[N-[6-(4,4,5,5,-tetramethyl-1,3,2-dioxaborolano)-2,3-dichlorobenzyl]-N-[2-(tert-butoxycarbonyl)ethylamino]methyl]anthracene (3f):

9-[N-[3-(methacrylamido)propylamino]methyl]-10-[N-[2-(tert-butoxycarbonyl)ethylamino]methyl]-anthracene (1, 0.25 g, 0.51 mmol) was placed into 100 mL round-bottom flask and stirred in 5 mL dimethylformamide until dissolved. 2-(Bromomethyl)-3,4-dichlorophenylboronic acid pinacol ester (2f, 0.56, 1.5 mmol, 3.0 equiv.) and DIEA (0.7 mL, 4.1 mmol, 8.0 eq) were added and stirred under $N_2$, in the dark, at room temperature for 48 h. The DMF was removed under vacuum; dichloromethane (20 mL) added and washed with phosphate buffer (40 mL of 0.1 M, pH 7.0). Collected dichloromethane solution was dried over $Na_2SO_4$. The dichloromethane was removed under vacuum and the resulting yellow residue triturated with hexanes (10 mL) for 15 minutes under slow flow of $N_2$. Trituration of the crude product (0.41 g) with cold IPA yielded an yellow powder of ~89% purity by HPLC (0.29 g, 54% yield).

Structure Determination:

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 16.4 min.

$^1$H NMR (400 MHz, $CDCl_3$): δ 1.22 (s, 9H), 1.32 (s, 12H) 1.38 (s, 12H), 1.56 (bs, 5H), 2.35 (t, 2H), 2.50 (t, 2H), 2.78 (t, 2H), 2.91 (q, 2H), 4.20 (s, 2H), 4.28 (s, 2H), 4.38 (s, 2H), 4.91 (s, 2H), 4.50 (bs, 1H), 4.65 (s, 1H), 4.79 (s, 1H), 7.36 (m, 4H), 7.45 (m, 2H), 7.69 (d, 2H), 8.16 (m, 4H).

Step 2

9-[N-[6-(4,4,5,5,-tetramethyl-1,3,2-dioxaborolano)-2,3-dichlorobenzyl]-N-[3-(methacrylamido)propylamino]methyl]-10-[N-[6-(4,4,5,5,-tetramethyl-1,3,2-dioxaborolano)-2,3-dichlorobenzyl]-N-[2-(carboxyethyl)amino]methyl]anthracene sodium salt (4f)

9-[N-[6-(4,4,5,5,-tetramethyl-1,3,2-dioxaborolano)-2,3-dichlorobenzyl]-N-[3-(metha-crylamido)propylamino]methyl]-10-[N-[6-(4,4,5,5,-tetramethyl-1,3,2-dioxaborolano)-2,3-dichlorobenzyl]-N-[2-(tert-butoxycarbonyl)ethylamino]methyl]anthracene (3f, 0.29 g, 0.27 mmol) was placed into a 100 mL round bottom flask and dissolved in 6 mL of a 60:40 $CH_2Cl_2$:TFA solution. The reaction mixture was allowed to stir at ambient temperature for 17 h or until HPLC analysis showed less than 0.1% of starting material remained. The solvents were removed under vacuum. The residual product was dissolved in 10 mL of $CH_2Cl_2$ followed by removal of the solvent under vacuum. The dichloromethane dissolution/evaporation treatments were repeated until the product became a yellow powder. The powder was dissolved in 10 mL of dichloromethane and added dropwise into 70 mL cold saturated aqueous $NaHCO_3$ at a rate such that the temperature stayed below 5° C. The solution was stirred for an additional 5 min at <5° C. followed by partitioning of the layers. The organic layer was dried over anhydrous $Na_2SO_4$, filtered and concentrated yielding 0.23 g yellow powder. The crude product was dissolved in 10 mL of anhydrous $CH_2Cl_2$ and transfered to a 100 mL round bottom flask. PS-DEAM beads (0.13 g, 1 eq) were added to the flask and the reaction mixture was shaken at ambient temperature for 16 h. The beads were filtered and washed with 5 mL dichloromethane. The combined organic solutions were concentrated under vacuum. Pure product (0.2 g, 71%) was obtained as a yellow powder.

Structure Determination:

RP-HPLC conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 14.1 min.

$^1$H NMR (400 MHz, $CDCl_3$): δ 1.35 (s, 12H), 1.38 (s, 12H), 1.58 (m, 5H), 2.28 (t, 2H), 2.42 (t, 2H), 2.70 (q, 2H), 2.89 (t, 2H), 4.28 (s, 2H), 4.42 (s, 2H), 4.48 (s, 2H), 4.60 (s, 2H), 4.92 (s, 1H), 4.05 (m, 1H), 5.30 (s, 1H), 7.38 (m, 3H), 7.49 (m, 4H), 7.58 (d, 1H), 7.72 (m, 1H), 7.88 (d, 1H), 7.91 (d, 1H), 8.17 (m, 1H).

ESI-MS (TFA/acetonitrile/water): 822.3 $(M-H_2O+H)^+$, 804.4 $(M-2H_2O+H)^+$ for the bis-boronic acid. Boronic esters are not observed under the acidic conditions of this analysis.

EXAMPLE 10

Synthesis of 4-Trifluoromethoxy Indicator

9-[N-[6-(4,4,5,5,-tetramethyl-1,3,2-dioxaborolano)-3-(trifluoromethoxy)benzyl]-N-[3-(methacrylamido)propylamino]methyl]-10-[N-[6-(4,4,5,5-tetra-methyl-1,3,2-dioxaborolano)-3-(trifluoromethoxy)benzyl]-N-[2-(carboxyethyl)amino]methyl]-anthracene sodium salt (4g)

Step 1

9-[N-[6-(4,4,5,5,-tetramethyl-1,3,2-dioxaborolano)-3-(trifluoromethoxy)benzyl]-N-[3-(methacrylamido)propylamino]methyl]-10-[N-[6-(4,4,5,5,-tetramethyl-1,3,2-dioxaborolano)-3-(trifluoromethoxy)benzyl]-N-[2-(tert-butoxycarbonyl)ethylamino]methyl]anthracene (3g)

9-[N-[3-(methacrylamido)propylamino]methyl]-10-[N-[2-(tert-butoxycarbonyl)ethylamino]methyl]-anthracene (1, 0.2 g, 0.41 mmol) was placed into 150 mL round-bottom flask. It was dissolved in 5 mL of degassed dimethylformamide. 2-(Bromomethyl)-4-(trifluoromethoxy)phenylboronic acid pinacol ester (2g, 0.37, 0.97 mmol, 2.4 equiv.) was dissolved in 4 mL of $N_2$ sparged DMF and added to reaction flask. The solution was stirred and flushed with $N_2$ for 5 minutes. DIEA (0.6 mL, 3.5 mmol, 8.0 equiv.) was added to the reaction mixture and the solution was allowed to stir under a gentle stream of nitrogen and in the dark at ambient temperature overnight. After 24 h the solvent was evaporated in vacuo. The residual product was dissolved in 10 mL of dichloromethane and extracted with 3×15 mL portions of phosphate buffer (0.1 M, pH 7.0). The dichloromethane solution was dried and evaporated in vacuo resulting in a golden oily residue. The crude product was stirred for 15 minutes with 5 mL of ether and then the solvent was removed. The yellow oily residue was kept under vacuum for 30 min resulting in foamy powder (3 g, 0.41 g, 91% yield).

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 15.0 min.

Step 2

9-[N-[6-(4,4,5,5,-tetramethyl-1,3,2-dioxaborolano)-3-(trifluoromethoxy)benzyl]-N-[3-(methacrylamido)propyl amino]methyl]-10-[N-[6-(4,4,5,5,-tetramethyl-1,3,2-dioxaborolano)-3-(trifluoromethoxy)benzyl]-N-[2-(carboxyethyl)amino]methyl] anthracene sodium salt (4g)

9-[N-[6-(4,4,5,5,-tetramethyl-1,3,2-dioxaborolano)-3-(trifluoromethoxy)benzyl]-N-[3-(methacryl-amido)propylamino]methyl]-10-[N-[6-(4,4,5,5,-tetramethyl-1,3,2-dioxaborolano)-3-(trifluoromethoxy)benzyl]-N-[2-(tert-butoxycarbonyl)ethylamino]methyl]anthracene (3 g, 0.4 g, 0.37 mmol) was placed into a 100 mL round bottom flask and dissolved in 5 mL of a 60:40 degassed $CH_2Cl_2$:TFA solution. The reaction mixture was allowed to stir at ambient temperature for 21 h or until HPLC analysis showed less than 0.1% of starting material remained. The residual product was washed with 10 mL of $CH_2Cl_2$ followed by removal of the solvent under vacuum. The dichloromethane washes were repeated several times. The powder was dissolved in 10 mL of dichloromethane and added dropwise into 80 mL cold saturated aqueous $NaHCO_3$ at a rate such that the temperature stayed below 5° C. The solution was stirred for an additional 5 min at <5° C. followed by partitioning of the layers. The organic extracts were dried over anhydrous $Na_2SO_4$, filtered and concentrated yielding 0.18 g yellow powder (4 g, 46% yield)

Structure Determination:

RP-HPLC conditions: HP 1100 HPLC chromatograph, Waters 4.6×100 mm Symmetry 3.5μ C18 column (with Sentry C18 guard column), 0.010 mL injection (sample dissolved in 70/30 water/MeCN with 1% v/v TFA), 0.100 mL injection loop, 0.75 mL/min, 254 nm detection, A=water (0.1% TFA) and B=MeCN (0.1% v/v TFA), gradient 10% B 2 min, 10-80% B over 18 min, 80-100% B over 2 min, 100% B 2 min, retention time 12.9 min.

$^1$H NMR (400 MHz, $CDCl_3$): δ 1.32 (s, 12H), 1.33 (s, 12H), 1.51 (s, 6H), 2.31 (bm, 2H), 2.40 (bt, 2H), 2.82 (bt, 2H), 2.89 (bm, 2H), 3.85 (s, 2H), 4.22 (s, 2H), 4.43 (s, 2H), 4.56 (s, 2H), 4.86 (d, 2H), 4.88 (bs, 1H,), 7.32 (d, 1H), 7.40 (m, 5H), 7.82 (d, 1H), 7.92 (d, 1H), 7.96 (m, 2H), 8.40 (d, 2H), 8.27 (m, 2H).

EXAMPLE 11

Synthesis of 4-Sulfonamide Indicator

9-[N-[6-(4,4,5,5,-tetramethyl-1,3,2-dioxaborolano)-3-(N,N-dimethylsulfamoyl)benzyl]-N-[3-(methacrylamido)propylamino]methyl]-10-[N-[6-(4,4,5,5,-tetramethyl-1,3,2-dioxaborolano)-3-(N,N-dimethylsulfamoyl)benzyl]-N-[2-(carboxyethyl)amino]methyl]anthracene sodium salt (4h)

Step 1

9-[N-[6-(4,4,5,5,-tetramethyl-1,3,2-dioxaborolano)-3-(N,N-dimethylsulfamoyl)benzyl]-N-[3-(methacrylamido)propylamino]methyl]-10-[N-[6-(4,4,5,5,-tetramethyl-1,3,2-dioxaborolano)-3-(N,N-dimethylsulfamoyl)benzyl]-N-[2-(tert-butoxycarbonyl)ethylamino]methyl]anthracene (3h)

9-[N-[3-(methacrylamido)propylamino]methyl]-10-[N-[2-(tert-butoxycarbonyl)ethylamino]methyl]-anthracene (1, 0.27 g, 0.55 mmol) was dissolved in anhydrous DMF (2 mL) in a 25 mL round-bottom flask. 2-(Bromomethyl)-4-(N,N-dimethylsulfamoyl)phenylboronic acid pinacol ester (2h, 0.595 g, 1.47 mmol, 2.7 equiv.) and DIEA (0.765 mL, 4.4 mmol, 8 eq) were added and stirred under $N_2$, in the dark, at room temperature for 19 hours. The DMF was removed under vacuum, dichloromethane (10 mL) added and washed with phosphate buffer (2×10 mL of 0.1 M, pH 7.0). The dichloromethane solution was dried over $Na_2SO_4$, filtered and removed under vacuum. Trituration of the crude product with hexanes (2×5 mL) yielded a yellow powder of ~90% purity by HPLC (0.59 g, 94% yield).

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 14.6 min.

Step 2

9-[N-[6-(4,4,5,5,-tetramethyl-1,3,2-dioxaborolano)-3-(N,N-dimethylsulfamoyl)benzyl]-N-[3-(methacrylamido)propylamino]methyl]-10-[N-[6-(4,4,5,5,-tetramethyl-1,3,2-dioxaborolano)-3-(N,N-dimethylsulfamoyl)benzyl]-N-[2-(carboxyethyl)amino]methyl]anthracene sodium salt (4h)

9-[N-[6-(4,4,5,5,-tetramethyl-1,3,2-dioxaborolano)-3-(N,N-dimethylsulfamoyl)benzyl]-N-[3-(methacrylamido)propylamino]methyl]-10-[N-[6-(4,4,5,5,-tetramethyl-1,3,2-dioxaborolano)-3-(N,N-dimethylsulfamoyl)benzyl]-N-[2-(tert-butoxycarbonyl)ethylamino]methyl]anthracene (3h, 0.44 g, 0.39 mmol) was placed into a 100 mL round bottom flask and dissolved in 10 mL of a 60:40 $CH_2Cl_2$:TFA solution prepared from $N_2$ sparged reagents. The reaction mixture was allowed to stir at ambient temperature for 28 h. The solvents were removed under vacuum. The residual product was dissolved in 20 mL of $CH_2Cl_2$ followed by removal of the solvent under vacuum. The dichloromethane dissolution/evaporation treatments were repeated four more times until the product became a yellow powder. The powder was dissolved in 20 mL of dichloromethane and added dropwise into 40 mL of ice-cold saturated aqueous $NaHCO_3$ at a rate such that the temperature stayed below 5° C. The solution was stirred for an additional 5 min at <5° C. followed by partitioning of the layers. The organic layer was dried over anhydrous $Na_2SO_4$, filtered and concentrated yielding 0.24 g (57%) product as a yellow powder.

Structure Determination:

RP-HPLC conditions: HP 1100 HPLC chromatograph, Waters 4.6×100 mm Symmetry 3.5μ C18 column (with Sentry C18 guard column), 0.010 mL injection (sample dissolved in 70/30 water/MeCN with 1% v/v TFA), 0.100 mL injection loop, 0.75 mL/min, 254 nm detection, A=water (0.1% TFA) and B=MeCN (0.1% v/v TFA), gradient 10% B 2 min, 10-80% B over 18 min, 80-100% B over 2 min, 100% B 2 min, retention time 12.7 min.

ESI-MS (TFA/acetonitrile/water): 920.3 (M−H$_2$O+Na)$^+$, 898.2 (M−H$_2$O+H)$^+$ for the bis-boronic acid. Boronic esters are not observed under the acidic conditions of this analysis.

EXAMPLE 12

Synthesis of 2-Methyl Indicator

9-[N-[2-(4,4,5,5,-tetramethyl-1,3,2-dioxaborolano)-3-methylbenzyl]-N-[3-(methacrylamido)propylamino]methyl]-10-[N-[2-(4,4,5,5,-tetramethyl-1,3,2-dioxaborolano)-3-methylbenzyl]-N-[2-(carboxyethyl)amino]methyl]anthracene (8).

Step 1

2-(bromomethyl)-6-methylphenylboronic acid (6)

2,6-dimethylphenylboronic acid (2.22 g, 14.8 mmol), NBS (1.31 g, 7.36 mmol, 0.5 eq) and AIBN (0.17 g, 1.0 mmol. 0.07 eq) were heated in refluxing CCl$_4$ for 2 hours. The solution was allowed to cool then filtered. The solution was then washed with water (50 mL), dried over Na$_2$SO$_4$ and the solvent evaporated in vacuo. The resulting white powder (1.66 g) was ~84% pure by HPLC and contained starting material and some di-brominated product. Column chromatography on silica gel 60 (elution conditions 0%-2% methanol in dichloromethane) failed to improve the purity and the crude material was used for the next step.

Step 2

9-[N-[2-(4,4,5,5,-tetramethyl-1,3,2-dioxaborolano)-3-methylbenzyl]-N-[3-(metha-crylamido)propylamino]methyl]-10-[N-[2-(4,4,5,5,-tetramethyl-1,3,2-dioxaborolano)-3-methylbenzyl]-N-[2-(tert-butoxycarbonyl)ethylamino]methyl]anthracene (7):

9-[N-[3-(methacrylamido)propylamino]methyl]-10-[N-[2-(tert-butoxycarbonyl)ethylamino]methyl]-anthracene (1, 0.85 g, 0.17 mmol) was placed into a 50 mL round-bottom flask and stirred in 2 mL dimethylformamide until dissolved. 2-(Bromomethyl)-6-methylphenylboronic acid (6, 389 mg, 1.7 mmol) and DIEA (0.24 mL, 1.4 mmol, 8 eq) were added and heated to 80° C. in an oil bath under an Argon filled balloon overnight. The DMF was removed under vacuum, dichloromethane (20 mL) added and washed with phosphate buffer (3×10 mL of 0.1 M, pH 7.0). The organic solvent was dried over Na$_2$SO$_4$ the solvent was removed under vacuum and the resulting yellow solid triturated with hexanes (2×10 mL). This crude product was purified by flash column chromatography on silica gel 60 eluted with 1-5% methanol in dichloromethane to yield 93% pure material (55 mg, 41%).

Structure Determination:

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 15.8 min.

Step 3

9-[N-[2-(4,4,5,5,-tetramethyl-1,3,2-dioxaborolano)-3-methylbenzyl]-N-[3-(methacrylamido)propylamino]methyl]-10-[N-[2-(4,4,5,5,-tetramethyl-1,3,2-dioxaborolano)-3-methylbenzyl]-N-[2-(carboxyethyl)amino]methyl]anthracene trifluoroacetic acid salt (8)

9-[N-[2-(4,4,5,5,-tetramethyl-1,3,2-dioxaborolano)-3-methylbenzyl]-N-[3-(methacrylamido)propylamino]methyl]-10-[N-[2-(4,4,5,5,-tetramethyl-1,3,2-dioxaborolano)-3-methylbenzyl]-N-[2-(tert-butoxycarbonyl)ethylamino]methyl]anthracene (7, 55 mg, 0.070 mmol) was dissolved in 2 mL of a 60:40 CH$_2$Cl$_2$:TFA solution and stirred overnight under a balloon filled with Argon. An additional 10 mL of dichloromethane was added and the solvents were removed under vacuum. Dichloromethane (10 mL) was added and the solvent again removed under vacuum. The dissolution/evaporation step was repeated three more times. The crude product was triturated with ether (10 mL) then heptane (3 mL) yielding ~90% pure product as trifluoroacetic acid salt (59 mg, 88%) as a yellow powder.

Structure Determination:

RP-HPLC conditions: RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 14.2 min.

ESI-MS (TFA/acetonitrile/water): 694.4 (M−2H$_2$O+H)$^+$, 712.4 (M−H$_2$O+H)$^+$, 730.4 (M+H)$^+$.

EXAMPLE 13

Synthesis of 4-Cyano Indicator

9-[N-[6-(4,4,5,5,-tetramethyl-1,3,2-dioxaborolano)-3-cyanobenzyl]-N-[3-(methacrylamido)propylamino]methyl]-10-[N-[6-(4,4,5,5,-tetramethyl-1,3,2-dioxaborolano)-3-cyanobenzyl]-N-[2-(carboxyethyl)amino]methyl]anthracene sodium salt (14a).

Step 1

3-Methyl-4-(4,4,5,5-tetramethyl-[1,2,3]dioxaborolan-2-yl)-benzonitrile (11a)

4-Bromo-3-methylbenzonitrile (9a, 5.0 g, 0.0255 mol, 1.0 equiv.) was placed into a 250 mL round-bottom flask containing 153 mL of anhydrous dimethylformamide. Potassium acetate (7.5 g, 0.076 mol, 3 equiv.), 4,4,4',4',5,5,5',5'-Octamethyl-2,2'-bi-1,3,2-dioxaborolane (10, 7.12 g, 0.028 mol, 1.1 equiv.) and [1,1'-bis(diphenylphosphino)-ferrocene]dichloropalladium(II) (0.56 g, 0.00076 mol, 0.03 equiv.) were added to the flask and the reaction mixture was heated to 80 C for 24 h. The solution was cooled to ambient temperature and the suspension was filtered hot. Collected solvent was removed under vacuum. The obtained oily dark brown product was dissolved in 200 mL ethyl acetate and transferred to a separatory funnel. 250 mL of water was added and the solution was extracted. The organic layer was collected and dried over anhydrous Na$_2$SO$_4$. The solvent was removed in vacuo. The crude product was purified by flash column chromatography on silica gel 60 (elution conditions 2%-20%

EtOAc/Hexane). Approximately 5 g of material was collected. The product was further purified by crystallization from hot hexane. Pure product (11a) was obtained (3.7 g, yield 60%).

Structure Determination:

RP-HPLC Conditions: HP 1100 HPLC chromatograph, 3.9×150 mm Symmetry Column HR C18 column, 0.010 mL injection, 0.75 mL/min, 1.500 mL injection loop, 254 nm detection, A water (0.1% TFA) and B=MeCN (0.1% TFA), gradient 10% B 2 min, 10-80% B over 18 min, 80-100% B over 2 min, 100% B 2 min, retention time 10.7 min.

$^1$H NMR (400 MHz, CDCl$_3$): δ 1.35 (s, 12H, C(CH$_3$)$_3$), 2.55 (s, 3H, CH$_3$), 7.41 (m, 2H, ArH), 7.81 (m, 1H, ArH).

Step 2

3-Bromomethyl-4-(4,4,5,5-tetramethyl-[1,2,3]dioxaborolan-2-yl)-benzonitrile (12a)

3-Methyl-4-(4,4,5,5-tetramethyl-[1,2,3]dioxaborolan-2-yl)-benzonitrile (11a, 3.3 g, 0.0136 mol, 1.0 eq) was placed into a 250 mL round-bottom flask containing 50 mL of carbon tetrachloride. NBS (2.5 g, 0.0142 mol, 1.05 equiv.) and catalytic amount of 2,2'-azobisisobutyro-nitrile (0.03 g, 0.00018 mol, 0.014 equiv.) were added and the reaction mixture was refluxed for 53 h. The resulting solution was filtered hot then the solvent was removed under vacuum. The crude product was purified by crystallization from hot hexane. Product (12a) containing some 11a was obtained (3.08 g, 70%).

Structure Determination:

RP-HPLC Conditions: HP 1100 HPLC chromatograph, 3.9×150 mm Symmetry Column HR C18 column, 0.010 mL injection, 0.75 mL/min, 1.500 mL injection loop, 254 nm detection, A=water (0.1% TFA) and B=MeCN (0.1% TFA), gradient 10% B 2 min, 10-80% B over 18 min, 80-100% B over 2 min, 100% B 2 min, retention time 13.4 min.

$^1$H NMR (400 MHz, CDCl$_3$): δ 1.38 (s, 12H, C(CH$_3$)$_3$), 4.85 (s, 2H, CH$_2$Br), 7.55 (d, 1H, ArH), 7.68 (s, 1H, ArH), 7.92 (d, 1H, ArH).

Step 3

9-[N-[6-(4,4,5,5,-tetramethyl-1,3,2-dioxaborolano)-3-cyanobenzyl]-N-[3-(metha-crylamido)propylamino]methyl]-10-[N-[6-(4,4,5,5,-tetramethyl-1,3,2-dioxaborolano)-3-cyanobenzyl]-N-[2-(tert-butoxycarbonyl)ethylamino]methyl]anthracene (13a)

9-[N-[3-(methacrylamido)propylamino]methyl]-10-[N-[2-(tert-butoxycarbonyl)ethylamino]methyl]-anthracene (1, 0.3 g, 0.00061 mol, 1.0 eq) was placed into 25 mL round-bottom flask and dissolved in 4.5 mL of degassed dimethylformamide. 3-Bromomethyl-4-(4,4,5,5-tetramethyl-[1,2,3]dioxaborolan-2-yl)-benzonitrile (12a, 0.53, 0.0016 mol, 2.7 eq) was dissolved in 2 mL of N$_2$ sparged DMF and added to reaction flask. The solution was stirred and flushed with N$_2$ for 5 minutes. DIEA (0.85 mL, 0.0049 mol, 8.0 equiv.) was added to the reaction mixture and the solution was allowed to stir under a gentle stream of nitrogen and in the dark at ambient temperature for 26 h. The reaction solvent was evaporated in vacuo. The residual product was dissolved in 20 mL of dichloromethane and extracted with 2×10 mL portions of phosphate buffer (0.1 M, pH 7.0). The combined dichloromethane extracts were dried and evaporated in vacuo resulting in a golden oily residue. The crude product was stirred for 15-30 minutes with 5 mL of hexane until yellow precipitate occurred. It was filtered and the weight of the product was determined (~0.9 g of yellow powder). The crude product was further purified by multiple crystallizations from hot 2-propanol (~3 mL of IPA). Pure product (13a) was collected (0.07 g, purity 98.8% by HPLC).

Structure Determination:

RP-HPLC Conditions: HP 1100 HPLC chromatograph, Waters 3.9×150 mm Symmetry Column HR C18 column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 15.2 min.

$^1$H NMR (400 MHz, CDCl$_3$): δ 1.31 (s, 12H, O—C(CH$_3$)$_2$C(CH$_3$)$_2$,C—O), 1.34 (s, 12H, O—C(CH$_3$)$_2$C(CH$_3$)$_2$,C—O), 1.35 (s, 9H, C(CH$_3$)$_3$), 1.63 (m, 3H, N—CH$_2$CH$_2$CH$_2$—N+NH overlap), 2.51 (m, 4H), 2.59 (t, 2H), 3.10 (q, 2H), 3.89 (s, 2H), 3.99 (s, 2H), 4.45 (s, 2H), 4.53 (s, 2H), 5.09 (m, 1H), 5.13 (s, 1H), 5.22 (t, 1H), 7.29 (d, 1H, ArH), 7.42 (d, 1H, ArH), 7.50 (m, 5H, ArH), 7.62 (d, 1H, ArH), 7.70 (s, 1H, ArH), 7.78 (d, 1H, ArH), 8.35 (m, 2H, ArH), 8.41 (d, 2H, ArH).

ESI-MS: m/z 790.4 (M$^+$, 100%). Boronic esters are not observed under the acidic conditions of this analysis.

Step 4

9-[N-[6-(4,4,5,5,-tetramethyl-1,3,2-dioxaborolano)-3-cyanobenzyl]-N-[3-(methacrylamido)-propyl amino]methyl]-10-[N-[6-(4,4,5,5,-tetramethyl-1,3,2-dioxaborolano)-3-cyanobenzyl]-N-[2-(carboxyethyl) amino]methyl]anthracene sodium salt (14a)

9-[N-[6-(4,4,5,5,-tetramethyl-1,3,2-dioxaborolano)-3-cyanobenzyl]-N-[3-(methacrylamido)-propylamino]methyl]-10-[N-[6-(4,4,5,5,-tetramethyl-1,3,2-dioxaborolano)-3-cyanobenzyl]-N-[2-(tert-butoxycarbonyl)ethylamino]methyl]anthracene (13a, 0.064 g, 0.066 mmol, 1.0 eq) was placed into a 25 mL round bottom flask and dissolved in 2.5 mL of a 60:40 degassed CH$_2$Cl$_2$:TFA solution. The reaction mixture was allowed to stir at ambient temperature for 24 h. The residual product was washed with 5 mL of CH$_2$Cl$_2$ followed by removal of the solvent under vacuum. The dichloromethane washes were repeated until the product became a yellow powder. The powder was dissolved in 10 mL of dichloromethane and added dropwise into 20 mL cold saturated aqueous NaHCO$_3$ at a rate such that the temperature stayed below 5° C. The solution was stirred for an additional 5 min at <5° C. followed by partitioning of the layers. The organic extracts were dried over anhydrous Na$_2$SO$_4$, filtered and concentrated yielding 0.042 g yellow powder. The crude product was dissolved in 3 mL of anhydrous CH$_2$Cl$_2$ and transfered to a 25 mL round bottom flask. PS-DEAM beads (0.039 g, 1 mmol, 1 eq) were added to the flask and the reaction mixture was flushed with nitrogen for 2 minutes. The solution was shaken at ambient temperature for 16 h. The beads were filtered and washed with 2×10 mL dichloromethane. The combined organic solutions were concentrated under vacuum. Pure product (14a) was obtained (34 mg of indicator).

Structure Determination:

RP-HPLC conditions: HP 1100 HPLC chromatograph, Waters 4.6×100 mm Symmetry 3.5µ C18 column, 0.010 mL injection (sample dissolved in 70/30 water/MeCN with 1% v/v TFA), 0.100 mL injection loop, 0.75 mL/min, 254 nm detection, A=water (0.1% TFA) and B=MeCN (0.1% v/v TFA), gradient 10% B 2 min, 10-80% B over 18 min, 80-100% B over 2 min, 100% B 2 min, retention time 12.9 min.

$^1$H NMR (400 MHz, CDCl$_3$): δ 1.33 (s, 12H), 1.36 (s, 12H) 1.65 (m, 2H), 1.71 (bs, 3H), 2-35 (t, 2H), 2.48 (t, 2H), 2.88 (t, 2H), 2.98 (q, 2H), 4.01 (s, 2H), 4.25 (s, 2H), 4.48 (s, 2H), 4.58 (s, 2H), 5.10 (s, 1H), 5.28 (s, 1H), 5.61 (bs, 1H), 7.45 (m, 5H), 7.65 (d, 1H), 7.72 (d, 2H), 7.81 (d, 1H), 7.92 (d, 2H), 8.05 (d, 1H), 8.30 (d, 2H).

EXAMPLE 14

Synthesis of 4-Nitro Indicator

9-[N-[6-(4,4,5,5,-tetramethyl-1,3,2-dioxaborolano)-3-nitrobenzyl]-N-[3-(methacrylamido)propylamino]methyl]-10-[N-[6-(4,4,5,5,-tetramethyl-1,3,2-dioxaborolano)-3-nitrobenzyl]-N-[2-(carboxyethyl)amino]methyl]anthracene sodium salt (14b).

Step 1

3-Nitro-6-(4,4,5,5-tetramethyl-[1,2,3]dioxaborolan-2-yl)-toluene (11b)

2-Bromo-5-nitrotoluene (9b, 10.2 g, 47.2 mmol) was placed into a 100 mL round-bottom flask with potassium acetate (7.14 g, 72.7 mmol), 4,4,4',4',5,5,5',5'-Octamethyl-2,2'-bi-1,3,2-dioxaborolane (10, 13.3 g, 52.3 mmol), [1,1'-bis(diphenylphosphino)-ferrocene]dichloropalladium(II) (413 mg, 0.506 mmol) and DMSO (50 mL) and the reaction mixture was heated to 80° C. for 4 days. The solution was cooled to ambient temperature, ice water (125 mL) was added and the black suspension was extracted with ethyl acetate (3×100 mL). The solvent was removed in vacuo and the crude product was purified by flash column chromatography on silica gel 60 eluted with hexanes then 5% EtOAc/Hexane). Approximately 95% pure product (2.09 g, 17%) was obtained from the purest fraction.

Structure Determination:

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 10.48.

$^1$H NMR (400 MHz, CDCl$_3$): δ 1.36 (s, 12H, C(CH$_3$)$_3$), 2.62 (s, 3H, CH$_3$), 7.89 (d, 2H, ArH), 7.92 (dd, 1H, ArH), 7.97 (d, 1H).

Step 2

3-Bromomethyl-4-(4,4,5,5-tetramethyl-[1,2,3]dioxaborolan-2-yl)-nitrobenzene (12b)

3-Nitro-6-(4,4,5,5-tetramethyl-[1,2,3]dioxaborolan-2-yl)-toluene (11b, 3.59 g, 13.6 mmol) was placed into a 500 mL round-bottom flask containing 50 mL of benzene. NBS (2.68 g, 15.0 mmol, 1.1 equiv.) and catalytic amount of 2,2'-azobisisobutyro-nitrile (AIBN, 84 mg, 0.5 mmol) were added and the reaction mixture was refluxed under an Argon stream for 3.5 h. Additional NBS (0.27 g, 1.5 mmol. 0.1 eq) was added and reflux continued for 2 more hours. The cooled suspension was filtered and the solvent was removed under vacuum. The crude product was purified by crystallization from hot hexane. Product (12b) was obtained (2.12 g, 46%).

Structure Determination:

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 12.5.

$^1$H NMR (400 MHz, CDCl$_3$): δ 1.40 (s, 12H, C(CH$_3$)$_3$), 4.92 (s, 2H, CH$_2$Br), 7.98 (d, 1H, ArH), 8.08 (dd, 1H, ArH), 8.22 (d, 1H, ArH).

Step 3

9-[N-[6-(4,4,5,5,-tetramethyl-1,3,2-dioxaborolano)-3-nitrobenzyl]-N-[3-(metha-crylamido)propylamino]methyl]-10-[N-[6-(4,4,5,5,-tetramethyl-1,3,2-dioxaborolano)-3-nitrobenzyl]-N-[2-(tert-butoxycarbonyl)ethylamino]methyl]anthracene (13b):

9-[N-[3-(methacrylamido)propylamino]methyl]-10-[N-[2-(tert-butoxycarbonyl)ethylamino]methyl]-anthracene (1, 0.509 g, 1.04 mmol) was placed into 100 mL round-bottom flask and stirred in 5 mL dimethylformamide until dissolved. 4-Nitro-2-(bromomethyl)phenylboronic acid pinacol ester (12b, 1.09, 3.19 mmol, 3 equiv.) and DIEA (1.45 mL, 8.38 mmol, 8 eq) were added and the solution heated to 80° C. in an oil bath and under a balloon filled with Argon for 2 hours. The DMF was removed under vacuum, dichloromethane (50 mL) added and washed with phosphate buffer (2×50 mL of 0.1 M, pH 7.0). The aqueous solution was backwashed with dichloromethane (25 mL) and the combined organic solutions dried over Na$_2$SO$_4$. The organics were removed under vacuum and the resulting red-yellow oil triturated twice with boiling hexanes (50 mL each) to yield a tan powder. Trituration with boiling 80/20 ethyl acetate/IPA yielded 145 mg of pure product as a tan powder. More pure product (400 mg) precipitated from the cooled ethyl acetate/IPA and the pure solids are combined.

Structure Determination:

RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 16.0 min.

$^1$H NMR (400 MHz, CDCl$_3$): δ 1.32 (s, 12H, O—C(CH$_3$)$_2$C(CH$_3$)$_2$, C—O), 1.36 (s, 21H, O—C(CH$_3$)$_2$C(CH$_3$)$_2$, C—O+t-butyl), 1.65 (s, 3H, O=C—C(CH$_2$)CH$_3$), 1.75 (m, 2H, N—CH$_2$CH$_2$CH$_2$—N), 2.55 (t, 2H), 2.59 (t, 2H), 3.0 (t, 2H), 3.15 (m, 2H), 3.96 (s, 2H), 4.05 (s, 2H), 4.48 (s, 2H), 4.55 (s, 2H), 5.04 (s, 1H), 5.08 (s, 1H), 5.25 (br, 1H), 7.44-7.52 (m, 4H, ArH), 7.64 (d, 1H), 7.76 (dd, 1H, ArH), 7.80 (d, 1H), 7.92 (dd, 1H), 7.96 (d, 1H, ArH), 8.25 (d, 1H, ArH), 8.36-8.44 (m, 4H, ArH).

Step 4

9-[N-[6-(4,4,5,5,-tetramethyl-1,3,2-dioxaborolano)-3-nitrobenzyl]-N-[3-(methacrylamido)propylamino]methyl]-10-[N-[6-(4,4,5,5,-tetramethyl-1,3,2-dioxaborolano)-3-nitrobenzyl]-N-[2-(carboxyethyl)amino]methyl]anthracene sodium salt (14b)

9-[N-[6-(4,4,5,5,-tetramethyl-1,3,2-dioxaborolano)-3-nitrobenzyl]-N-[3-(methacrylamido)propylamino]methyl]-10-[N-[6-(4,4,5,5,-tetramethyl-1,3,2-dioxaborolano)-3-nitrobenzyl]-N-[2-(tert-butoxycarbonyl)ethylamino]methyl]anthracene (13b, 0.499 g, 0.493 mmol) was dissolved in 10 mL of a 60:40 $CH_2Cl_2$:TFA solution and stirred overnight. The solvents were removed under vacuum, the residual product was dissolved in 20 mL of $CH_2Cl_2$ followed by removal of the solvent under vacuum. The dichloromethane dissolution/evaporation treatments were repeated four more times until the product became a yellow powder. The powder was dissolved in 20 mL of dichloromethane and added dropwise into 80 mL cold saturated aqueous $NaHCO_3$ at a rate such that the temperature stayed below 5° C. The solution was stirred for an additional 5 min at <5° C. Additional dichloromethane (50 mL) was added to aid partitioning of the layers. The organic extracts were dried over anhydrous $Na_2SO_4$, filtered and concentrated yielding 157 mg yellow powder. The crude product was dissolved in 10 mL of anhydrous $CH_2Cl_2$ and transferred to a 100 mL round bottom flask. PS-DEAM beads (0.10 g) were added, the flask sealed with a septum and flushed with Argon and the reaction mixture was shaken at ambient temperature for 16 h. The beads were filtered and washed with dichloromethane (2×10 mL). The combined organic solutions were concentrated under vacuum. Pure product (0.125 mg, 26%) was obtained as a yellow powder.

Structure Determination:
RP-HPLC conditions: RP-HPLC Conditions: HP 1100 HPLC chromatograph, Waters 3.9×150 mm NovaPak HR C18 column with guard column, 0.010 mL injection, 0.75 mL/min, 1.500 mL injection loop, 254 nm detection, A=water (0.1% v/v TFA) and B=MeCN (0.1% v/v TFA), gradient 10% B 2 min, 10-80% B over 18 min, 80-100% B over 2 min, 100% B 2 min, retention time 13.7 min.

EXAMPLE 15

Synthesis of 4-Trifluoromethylsulfone Indicator

9-[N-[6-(4,4,5,5,-tetramethyl-1,3,2-dioxaborolano)-3-(trifluoromethylsulfonyl)benzyl]-N-[3-(methacrylamido)propylamino]methyl]-10-[N-[6-(4,4,5,5,-tetramethyl-1,3,2-dioxaborolano)-3-(trifluoromethylsulfonyl)benzyl]-N-[2-(carboxyethyl)amino]methyl]anthracene sodium salt (21)

Step 1

4-Bromo-3-methylbenzenesulfonyl fluoride (16)

4-Bromo-3-methylbenzenesulfonyl chloride (15, 9.87 g, 36.6 mmol), anhydrous potassium fluoride (8.50 g, 146 mmol, 4 eq) and 18-crown-6 (0.299 g, 1.13 mmol, 0.03 eq) were stirred in anhydrous acetonitrile (20 mL) overnight by which time HPLC showed complete conversion of starting material to product. Water (100 mL) was added to the reaction mixture and the product separated out as an oil. The aqueous solution was decanted then extracted with hexane (50 mL). The oil was dissolved in the hexane extract, dried over $Na_2SO_4$ and the solvent removed under vacuum. A waxy, white solid (8.08 g, 87%) was isolated.
M.p. 47-48° C.

Structure Determination:
RP-HPLC conditions: HP 1100 HPLC chromatograph, Waters 4.6×100 mm Symmetry 3.5μ C18 column (with Sentry C18 guard column), 0.010 mL injection (sample dissolved in 60/40 water/MeCN with 1% v/v TFA), 0.100 mL injection loop, 1.50 mL/min, 254 nm detection, A=water (0.1% TFA) and B=MeCN (0.1% v/v TFA), gradient 10% B 1 min, 10-80% B over 9 min, 80-100% B over 1 min, 100% B 1 min, retention time 10.5 min.
$^1$H NMR (400 MHz, $CDCl_3$): Γ2.5 (s, 3H), 7.68 (dd, 1H), 7.80 (d, 1H), 7.86 (d, 1H).

Step 2

6-Bromo-3-(trifluoromethylsulfonyl)toluene (17)

(TASF, 0.61 g, 2.2 mmol) was suspended in anhydrous pentane (40 mL) in an oven dried 2-neck flask equipped with addition funnel and cooled to ~5° C. 4-Bromo-3-methylbenzenesulfonyl fluoride (16, 5.00 g, 19.8 mmol) dissolved in pentane (40 mL) was added and a thermometer inserted into the suspension. Trimethyltrifluoromethylsilane (TFM-TMS, 6.4 mL, 41 mmol, 2.1 eq) dissolved in pentane (20 mL) was added to the suspension dropwise via the addition funnel such that the reaction temperature was maintained between 4-5° C. Stirring was continued for 5 hours while the suspension was allowed to warm up. The clear solution was decanted from a brown solid, washed with water (100 mL), dried over $Na_2SO_4$, filtered and the solvent removed under vacuum. A yellow oil (5.35 g, 89%) was isolated which then crystallized (needles) upon standing.

Structure Determination:
RP-HPLC conditions: HP 1100 HPLC chromatograph, Waters 4.6×100 mm Symmetry 3.5μ C18 column (with Sentry C18 guard column), 0.010 mL injection (sample dissolved in 60/40 water/MeCN with 1% v/v TFA), 0.100 mL injection loop, 1.50 mL/min, 254 nm detection, A=water (0.1% TFA) and B=MeCN (0.1% v/v TFA), gradient 10% B 1 min, 10-80% B over 9 min, 80-100% B over 1 min, 100% B 1 min, retention time 11.0 min.
$^1$H NMR (400 MHz, $CDCl_3$): δ 2.55 (s, 3H), 7.70 (dd, 1H), 7.85 (d, 1H), 7.7 (d, 1H).

Step 3

2-Methyl-4-(trifluoromethylsulfonyl)phenylboronic acid pinacol ester (18)

A 250 mL round bottom flask was charged with potassium acetate (5.0 g, 50 mmol), [1,1'-bis(diphenylphosphino)ferrocene]dichloropalladium(II) (0.373 g, 0.51 mmol) and bis(pinacolato)diboron (5.2 g, 20 mmol) and flushed with $N_2$. 6-Bromo-3-(trifluoromethylsulfonyl)toluene (17, 5.0 g, 16 mmol) in anhydrous DMF (100 mL) was added and the suspension heated to 80° C. under $N_2$ for 24 hours. The solvent was removed under vacuum and the resulting slurry eluted down silica gel 60 (60 g) with 95/5 Hexane/Ethyl acetate (500 mL). Removal of the solvent yielded 6.1 g crude product as a white, waxy solid. Recrystallization from hexanes yielded 3.78 g (68%) white crystals; a further 0.44 g was isolated from a second crop.

Structure Determination:

RP-HPLC conditions: HP 1100 HPLC chromatograph, Waters 4.6×100 mm Symmetry 3.5μ C18 column (with Sentry C18 guard column), 0.010 mL injection (sample dissolved in 60/40 water/MeCN with 1% v/v TFA), 0.100 mL injection loop, 1.50 mL/min, 254 nm detection, A=water (0.1% TFA) and B=MeCN (0.1% v/v TFA), gradient 10% B 1 min, 10-80% B over 9 min, 80-100% B over 1 min, 100% B 1 min, retention time 8.0 min.

$^1$H NMR (400 MHz, CDCl$_3$): δ 1.37 (s, 12H), 2.62 (s, 3H) 7.80 (m, 2H), 8.00 (d, 1H).

FAB MS (mNBA): 351 (M+H)$^+$, 335 (M−15)$^+$.

Step 4

2-Bromomethyl-4-(trifluoromethylsulfonyl)phenylboronic acid pinacol ester (19)

2-Methyl-4-(trifluoromethylsulfonyl)phenylboronic acid pinacol ester (18, 3.60 g, 10.3 mmol), N-bromosuccinimide (1.92 g, 10.8 mmol, 1.04 eq) and AIBN (25 mg, 0.15 mmol, 0.015 eq) were heated in refluxing CCl$_4$ (70 mL) while irradiated with a 75 watt incandescent bulb for 5 hours. The solution was then allowed to reach room temperature, gravity filtered and the solvent removed under vacuum. The crude product was purified on silica gel eluted with 0, 5 and then 10% ethyl acetate in hexanes and 19 mixed with some dibromide and 18 was isolated as a yellow oil (2.65 g, 60%).

Structure Determination:

RP-HPLC conditions: HP 1100 HPLC chromatograph, Waters 4.6×100 mm Symmetry 3.5μ C18 column (with Sentry C18 guard column), 0.010 mL injection (sample dissolved in 60/40 water/MeCN with 1% v/v TFA), 0.100 mL injection loop, 1.50 mL/min, 254 nm detection, A=water (0.1% TFA) and B=MeCN (0.1% v/v TFA), gradient 10% B 1 min, 10-80% B over 9 min, 80-100% B over 1 min, 100% B 1 min, retention time 8.7 min.

$^1$H NMR (400 MHz, CDCl$_3$): δ 1.37 (s, 12H), 4.92 (s, 2H) 7.96 (dd, 1H), 8.02 (d, 1H), 8.08 (d, 1H).

Step 5

9-[N-[6-(4,4,5,5,-tetramethyl-1,3,2-dioxaborolano)-3-(trifluoromethylsulfonyl)benzyl]-N-[3-(methacrylamido)propylamino]methyl]-10-[N-[6-(4,4,5,5,-tetramethyl-1,3,2-dioxaborolano)-3-(trifluoromethylsulfonyl)benzyl]-N-[2-(tert-butoxycarbonyl)ethylamino]methyl]anthracene (20)

9-[N-[3-(methacrylamido)propylamino]methyl]-10-[N-[2-(tert-butoxycarbonyl)ethylamino]methyl]-anthracene (1, 0.706 g, 1.44 mmol), 2-Bromomethyl-4-(trifluoromethylsulfonyl)phenylboronic acid pinacol ester (19, 2.11 g) and DIEA (4.5 mL, 26 mmol) were dissolved in anhydrous DMF (12 mL) and stirred at room temperature under a N$_2$ stream. After 26 hours, the solvent was evaporated in vacuo. The residual product was dissolved in 30 mL of dichloromethane and washed with 2×30 mL portions of phosphate buffer (0.1 M, pH 7.0). The dichloromethane solution was dried over Na$_2$SO$_4$, filtered and evaporated in vacuo resulting in an orange oil. The crude product was triturated with hexanes (10 mL) then dissolved in minimal IPA and hexanes added until the solution became cloudy. The solvents were removed under vacuum leaving a yellow powder (1.93 g, 95%).

Structure Determination:

RP-HPLC conditions: HP 1100 HPLC chromatograph, Waters 4.6×100 mm Symmetry 3.5μ C18 column (with Sentry C18 guard column), 0.010 mL injection (sample dissolved in 70/30 water/MeCN with 1% v/v TFA), 0.100 mL injection loop, 0.75 mL/min, 254 nm detection, A=water (0.1% TFA) and B=MeCN (0.1% v/v TFA), gradient 10% B 2 min, 10-80% B over 18 min, 80-100% B over 2 min, 100% B 2 min, retention time 17.4 min.

$^1$H NMR (400 MHz, CDCl$_3$): δ 1.30 (s, 12H), 1.32 (s, 12H) 1.34 (s, 9H), 1.63 (s, 3H), 1.78-1.81 (m, 2H), 2.55-2.61 (m, 4H), 2.96 (t, 2H), 3.15 (m, 2H), 3.98 (s, 2H), 4.05 (s, 2H), 4.54 (s, 2H), 4.56 (s, 2H), 5.10 (bs, 1H), 5.12 (s, 1H), 5.30 (bt, 1H), 7.49-7.52 (m, 4H), 7.68 (dd, 1H), 7.80 (m, 2H), 7.84 (d, 1H), 7.94 (s, 1H), 8.18 (s, 1H), 8.40-8.42 (m, 4H).

ESI-MS (TFA/acetonitrile/water): 1004.2 (M−H$_2$O+H)$^+$, 1006.2 (M−H$_2$O+Na) for the bis-boronic acid. Boronic esters are not observed under the acidic conditions of this analysis.

Step 6

9-[N-[6-(4,4,5,5,-tetramethyl-1,3,2-dioxaborolano)-3-(trifluoromethylsulfonyl)benzyl]-N-[3-(methacrylamido)propylamino]methyl]-10-[N-[6-(4,4,5,5,-tetramethyl-1,3,2-dioxaborolano)-3-(trifluoromethylsulfonyl)benzyl]-N-[2-(carboxyethyl)amino]methyl]anthracene sodium salt (21)

9-[N-[6-(4,4,5,5,-tetramethyl-1,3,2-dioxaborolano)-3-(trifluoromethylsulfonyl)benzyl]-N-[3-(methacrylamido)propylamino]methyl]-10-[N-[6-(4,4,5,5,-tetramethyl-1,3,2-dioxaborolano)-3-(trifluoromethylsulfonyl)benzyl]-N-[2-(tert-butoxycarbonyl)ethylamino]methyl]anthracene (20, 1.00 g, 843 mmol) was dissolved in 30 mL of a 60:40 CH$_2$Cl$_2$: TFA solution prepared from N$_2$ sparged reagents. The reaction mixture was allowed to stir at ambient temperature for 22 h then the solvents were removed under vacuum. The residual product was dissolved in 30 mL of CH$_2$Cl$_2$ followed by removal of the solvent under vacuum. The dichloromethane dissolution/evaporation treatments were repeated four more times until the product became a yellow powder. The powder was dissolved in 30 mL of dichloromethane and added dropwise into 60 mL of ice-cold saturated aqueous NaHCO$_3$ at a rate such that the temperature stayed below 5° C. The solution was stirred for an additional 5 min at <5° C. followed by partitioning of the layers. The organic layer was dried over anhydrous Na$_2$SO$_4$, filtered and concentrated yielding 0.58 g (60%) product as a yellow powder.

Structure Determination:

RP-HPLC conditions: HP 1100 HPLC chromatograph, Waters 4.6×100 mm Symmetry 3.5μ C18 column (with Sentry C18 guard column), 0.010 mL injection (sample dissolved in 70/30 water/MeCN with 1% v/v TFA), 0.100 mL injection loop, 0.75 mL/min, 254 nm detection, A=water (0.1% TFA) and B=MeCN (0.1% v/v TFA), gradient 10% B 2 min, 10-80% B over 18 min, 80-100% B over 2 min, 100% B 2 min, retention time 15.5 min.

$^1$H NMR (400 MHz, CDCl$_3$): δ 1.32 (s, 12H), 1.35 (s, 12H) 1.69-1.72 (m, 5H), 2.41 (t, 2H), 2.53 (t, 2H), 2.89 (t, 2H), 3.03 (dd, 2H), 4.07 (s, 2H), 4.23 (s, 2H), 4.54 (s, 2H), 4.60 (s, 2H), 5.09 (s, 1H), 5.26 (s, 1H), 5.56 (m, 1H), 7.45-7.49 (m, 4H), 7.82 (m, 2H), 7.91 (m, 1H), 7.98 (d, 1H), 8.10-8.16 (m, 4H), 8.39 (m, 2H).

ESI-MS (TFA/acetonitrile/water): 948.0 (M−H$_2$O+H)$^+$, 970.0 (M−H$_2$O+Na)$^+$ for the bis-boronic acid. Boronic esters are not observed under the acidic conditions of this analysis.

EXAMPLE 16

Synthesis of 3,5-Dichloro-Indicator

9-[N-[6-(4,4,5,5,-tetramethyl-1,3,2-dioxaborolano)-2,4-(dichloro)benzyl]-N-[3-(methacrylamido)propylamino]methyl]-10-[N-[6-(4,4,5,5,-tetramethyl-1,3,2-dioxaborolano)-2,4-(dichloro)benzyl]-N-[2-(carboxyethyl)amino]-methyl]anthracene sodium salt (41)

Step 1

9-[N-[6-(4,4,5,5,-tetramethyl-1,3,2-dioxaborolano)-2,4-(dichloro)benzyl]-N-[3-(metha-crylamido)propylamino]methyl]-10-[N-[6-(4,4,5,5,-tetramethyl-1,3,2-dioxaborolano)-2,4-(dichloro)benzyl]-N-[2-(tert-butoxycarbonyl)ethylamino]methyl]anthracene (31):

9-[N-[3-(methacrylamido)propylamino]methyl]-10-[N-[2-(tert-butoxycarbonyl)ethylamino]methyl]-anthracene (1, 0.4 g, 0.82 mmol) was placed into 100 mL round-bottom flask and stirred in 10 mL dimethylformamide until dissolved. 6-(Bromomethyl)-3,5-dichlorophenylboronic acid pinacol ester (2i, 0.83 g, 2.3 mmol, 2.4 equiv.) and DIEA (1.14 mL, 6.6 mmol, 8.0 eq) were added and stirred under $N_2$, in the dark, at room temperature for 24 h. The DMF was removed under vacuum, dichloromethane (30 mL) added and washed with phosphate buffer (50 mL of 0.1 M, pH 7.0). The collected dichloromethane solution was dried over $Na_2SO_4$. The dichloromethane was removed under vacuum and the resulting yellow foamy residue triturated with hexanes (10 mL) for 15 minutes under slow flow of $N_2$. The crude product (1.02 g) was crystallized from hot IPA yielding a yellow powder (31, 0.38 g, 44% yield).

Structure Determination:
RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 8.7 min.

$^1$H NMR (400 MHz, $CDCl_3$): δ 1.23 (s, 9H), 1.32 (s, 12H), 1.37 (s, 12H), 1.41 (bs, 3H), 1.52 (m, 2H), 2.36 (t, 2H), 2.48 (t, 2H), 2.76 (t, 2H), 2.89 (q, 2H), 4.12 (s, 2H), 4.16 (s, 2H), 4.37 (s, 2H), 4.43 (s, 2H), 4.56 (t, 1H), 4.67 (s, 1H), 4.82 (t, 1H), 7.36 (m, 4H), 7.48 (d, 1H), 7.56 (d, 1H), 7.76 (t, 2H), 8.17 (m, 2H), 8.24 (m, 2H).

Step 2

9-[N-[6-(4,4,5,5,-tetramethyl-1,3,2-dioxaborolano)-2,4-(dichloro)benzyl]-N-[3-(methacrylamido)propylamino]methyl]-10-[N-[6-(4,4,5,5,-tetramethyl-1,3,2-dioxaborolano)-2,4-(dichloro)benzyl]-N-[2-(carboxyethyl)amino]methyl]anthracene sodium salt (4i)

9-[N-[6-(4,4,5,5,-tetramethyl-1,3,2-dioxaborolano)-2,4-(dichloro)benzyl]-N-[3-(methacrylamido)-propylamino]methyl]-10-[N-[6-(4,4,5,5,-tetramethyl-1,3,2-dioxaborolano)-2,4-(dichloro)benzyl]-N-[2-(tert-butoxycarbonyl)ethylamino]methyl]anthracene (3i, 0.38 g, 0.36 mmol) was placed into a 50 mL round bottom flask and dissolved in 10 mL of a 60:40 $CH_2Cl_2$:TFA solution. The reaction mixture was allowed to stir at ambient temperature overnight. After 20 h the solvents were removed under vacuum. The residual product was dissolved in 10 mL of $CH_2Cl_2$ followed by removal of the solvent under vacuum. The dichloromethane dissolution/evaporation treatments were repeated until the product became a yellow powder. The powder was dissolved in 30 mL of dichloromethane and added dropwise into 50 mL cold saturated aqueous $NaHCO_3$ at a rate such that the temperature stayed below 5° C. The solution was stirred for an additional 5 min at <5° C. followed by partitioning of the layers. The organic layer was dried over anhydrous $Na_2SO_4$, filtered and concentrated yielding a yellow powder. The crude product was dissolved in 15 mL of anhydrous $CH_2Cl_2$ and transfered to a 100 mL round bottom flask. PS-DEAM beads (0.2 g, 1 eq) were added to the flask and the reaction mixture was shaken at ambient temperature for 16 h. The beads were filtered and washed with 10 mL dichloromethane. The combined organic solutions were concentrated under vacuum. Pure product (0.19 g, 52% yield) was obtained as a yellow powder.

Structure Determination:
RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 7.9 min.

ESI-MS (TFA/acetonitrile/water): 822.11 $(M-H_2O+H)^+$ for the bis-boronic acid. Boronic esters are not observed under the acidic conditions of this analysis.

EXAMPLE 17

Synthesis of 3,5-Bis(Trifluoromethyl) Indicator

9-[N-[6-(4,4,5,5,-tetramethyl-1,3,2-dioxaborolano)-2,4-bis(trifluoromethyl)benzyl]-N-[3-(methacrylamido)propylamino]methyl]-10-[N-[6-(4,4,5,5,-tetramethyl-1,3,2-dioxaborolano)-2,4-bis(trifluoromethyl)benzyl]-N-[2-(carboxyethyl)amino]-methyl]anthracene sodium salt (27a)

Step 1

2-Bromo-4,6-bis(trifluoromethyl)toluene (23a)

2,4-Bis(trifluoromethyl)toluene (22a, 12.7 g, 56 mmol) was placed in a round-bottom flask. Then 28 ml TFA and 7.8 ml $H_2SO_4$ (28% of the amount of TFA) were added. NBS (10.0 g, 56 mmol, 1 eq) was added to the reaction mixture in small portions. The reaction was allowed to run at ambient temperature over two days. After 48 h the reaction was worked up. The reaction mixture was poured out to ice cold water (200 ml) and the organic layer (oily residue) was separated from water layer by extraction with $Et_2O$. Ether layer was washed with saturated $NaHCO_3$ aqueous solution and then the layers were separated. The organic layer was collected, dried over $Na_2SO_4$ and the solvent was removed. The pure product (13.1 g, 77% yield) as a slightly yellow oil was collected.

Structure Determination:
RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 12.3 min.

$^1$H NMR (400 MHz, CDCl$_3$): δ 2.54 (s, 3H), 7.64 (s, 1H), 8.00 (s, 1H).

Step 2

2-Methyl-3,5-Bis(trifluoromethyl)phenylboronic acid pinacol ester (24a)

2-Bromo-4,6-bis(trifluoromethyl)toluene (23a, 10.0 g, 30 mmol) was placed in a round-bottom flask and dissolved in 200 ml DMF. Then KOAc (8.8 g, 90 mmol, 3 eq) was added to the reaction mixture in one portion followed by addition of PdCl$_2$(dppf) (0.66 g, 0.9 mmol, 0.03 eq) and Bis(pinacolato)diboron (10.2 g, 45 mmol, 1.5 eq). The solution was stirred at 80° C. for 24 h. Then the solvent was removed and the black residue was subjected to plug column chromatography (DCM) resulting in dark green oily residue. The compound was further purified by second column chromatography (2% MeOH/DCM). Pure product (8.7 g, 76%) as a slightly green oil was collected.

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 9.1 min (for boronic acid) and 12.8 min (for pinacol ester).

$^1$H NMR (400 MHz, CDCl$_3$): δ 1.36 (s, 12H), 2.75 (s, 3H), 7.90 (s, 1H), 8.16 (s, 1H).

Step 3

2-(Bromomethyl)-3,5-Bis(trifluoromethyl)phenylboronic acid pinacol ester (25a)

2-Methyl-3,5-bis(trifluoromethyl)phenylboronic acid pinacol ester (24a, 2.0 g, 5.6 mmol) and 50 ml CCl$_4$ were placed in a 250 ml round-bottom flask. NBS (1.05, 5.88 mmol, 1.05 eq) and AIBN (0.013 g, 0.078 mmol, 0.014 eq) were added and the reaction mixture was refluxed for 3 h in the presence of 75 W incandescent bulb. After 3 h the solution was cooled down to room temperature allowing the succinimide to precipitate out. The solid was filtered off. The solvent was removed and oily product was collected. The crude product was purified by triturating with hexane which resulted in 90% pure product (25a, 2.2 g, 90% yield).

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 9.7 min (for boronic acid) and 12.9 min (for pinacol ester).

$^1$H NMR (400 MHz, CDCl$_3$): δ 1.41 (s, 12H), 5.08 (s, 2H), 7.94 (s, 1H), 8.24 (s, 1H).

Step 4

9-[N-[6-(4,4,5,5,-tetramethyl-1,3,2-dioxaborolano)-2,4-bis(trifluoromethyl)benzyl]-N-[3-(methacrylamido)propylamino]methyl]-10-[N-[6-(4,4,5,5,-tetramethyl-1,3,2-dioxa-borolano)-2,4-bis(trifluoromethyl)benzyl]-N-[2-(tert-butoxycarbonyl)ethylamino]methyl]-anthracene (26a)

9-[N-[3-(methacrylamido)propylamino]methyl]-10-[N-[2-(tert-butoxycarbonyl)ethylamino]methyl]-anthracene (1, 0.8 g, 1.6 mmol) was placed into 250 mL round-bottom flask. It was dissolved in 15 mL of degassed dimethylformamide. 2-(bromomethyl)-3,5-Bis(trifluoromethyl)phenylboronic acid pinacol ester (25a, 1.66, 3.8 mmol, 2.4 eq) was dissolved in 5 mL of N$_2$ sparged DMF and added to reaction flask. The solution was stirred and flushed with N$_2$ for 5 minutes. DIEA (2.2 mL, 12.8 mmol, 8.0 equiv.) was added to the reaction mixture and the solution was allowed to stir under a gentle stream of nitrogen and in the dark at ambient temperature over 4 nights. After 96 h the reaction was continued for 4.5 h at 60° C. Then the reaction was cooled down, the solvent was evaporated in vacuo. The residual product was dissolved in 50 mL of dichloromethane and extracted with 2×70 mL portions of phosphate buffer (0.1 M, pH 7.0). The dichloromethane solution was dried and evaporated in vacuo resulting in a brownish oily residue. The crude product was triturate with hexane (15 ml) for 30 minutes. Collected yellow powder was crystallized from hot IPA resulting in pure product (26a, 1.2 g, 59% yield).

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 10.8 min.

$^1$H NMR (400 MHz, CDCl$_3$): δ 1.23 (s, 9H), 1.32 (s, 12H), 1.36 (s, 12H), 1.74 (s, 5H), 2.31 (t, 2H), 2.8 (m, 5H), 2.88 (t, 2H), 4.08 (s, 2H), 4.16 (s, 2H), 4.47 (s, 2H), 4.76 (s, 2H), 5.12 (s, 1H), 5.32 (s, 1H), 7.44 (m, 4H), 7.88 (s, 1H), 7.96 (s, 1H), 8.08 (m, 2H), 8.14 (m, 2H), 8.20 (s, 1H), 8.29 (s, 1H).

Step 5

9-[N-[6-(4,4,5,5,-tetramethyl-1,3,2-dioxaborolano)-2,4-bis(trifluoromethyl)benzyl]-N-[3-(methacrylamido)propyl amino]methyl]-10-[N-[6-(4,4,5,5,-tetramethyl-1,3,2-dioxa-borolano)-2,4-bis(trifluoromethyl)benzyl]-N-[2(carboxyethyl)amino]methyl]anthracene sodium salt (27a)

9-[N-[6-(4,4,5,5,-tetramethyl-1,3,2-dioxaborolano)-2,4-bis(trifluoromethyl)benzyl]-N-[3-(methacrylamido)propylamino]methyl]-10-[N-[6-(4,4,5,5,-tetramethyl-1,3,2-dioxaborolano)-2,4-bis(trifluoromethyl)benzyl]-N-[2-(tert-butoxycarbonyl)ethylamino]methyl]-anthracene (26a, 0.013 g, 0.011 mmol) was placed into a 50 mL round bottom flask and dissolved in 5 mL of a 60:40 degassed CH$_2$Cl$_2$:TFA solution. The reaction mixture was allowed to stir at ambient temperature for 19 h. The residual product was washed with 10 mL of CH$_2$Cl$_2$ followed by removal of the solvent under vacuum. The dichloromethane washes were repeated several times. The resulting oily product was dissolved in 5 mL of dichloromethane and added dropwise into 25 mL cold saturated aqueous NaHCO$_3$ at a rate such that the temperature stayed below 5° C. The solution was stirred for an additional 5 min at <5° C. followed by partitioning of the layers. The organic extracts were dried over anhydrous Na$_2$SO$_4$, filtered and concentrated yielding 0.012 g yellow powder (27a).

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 9.6 min.

ESI-MS (TFA/acetonitrile/water): 956.0 (M−H$_2$O+H)$^+$ for the bis-boronic acid. Boronic esters are not observed under the acidic conditions of this analysis.

EXAMPLE 18

Synthesis of 5-Trifluoromethyl Indicator

9-[N-[2-(4,4,5,5,-tetramethyl-1,3,2-dioxaborolano)-4-(trifluoromethyl)benzyl]-N-[3-(methacrylamido)propylamino]methyl]-10-[N-[2-(4,4,5,5-tetra-methyl-1,3,2-dioxaborolano)-4-(trifluoromethyl)benzyl]-N-[2-(carboxyethyl)amino]methyl]-anthracene sodium salt (27b)

Step 1

2-Bromo-4-trifluoromethyltoluene (23b)

4-(Trifluoromethyl)toluene (22b, 9.0 g, 56 mmol) was placed in round-bottom flask. Then 20 ml TFA and 5.6 ml H$_2$SO$_4$ (28% of the amount of TFA) were added. NBS (10.0 g, 56 mmol, 1 eq) was added to the reaction mixture in small portions. The reaction was allowed to run at ambient temperature overnight. After 20 h the reaction was worked up. The reaction mixture was poured out to ice cold water (100 ml) and the organic layer (oily residue) was separated from the water layer by extraction with Et$_2$O. The ether layer was collected, dried over Na$_2$SO$_4$ and the solvent was removed. The pure product (7.86 g, 59% yield) as a slightly yellow oil was collected.

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 11.7 min.

$^1$H NMR (400 MHz, CDCl$_3$): δ 2.45 (s, 3H), 7.34 (d, 1H), 7.50 (d, 1H), 7.80 (s, 1H).

Step 2

6-Methyl-3-(trifluoromethyl)phenylboronic acid pinacol ester (24b)

2-Bromo-4-(trifluoromethyl)toluene (23b, 5 g, 21 mmol) was placed in round-bottom flask and dissolved in 150 ml DMF. Then KOAc (6.2 g, 63 mmol, 3 eq) was added to the reaction mixture in one portion followed by addition of PdCl$_2$ (dppf) (0.46 g, 0.63 mmol, 0.03 eq) and Bis(pinacolato)diboron 5.9 g, 23.1 mmol, 1.1 eq). The solution was stirred at 80° C. for 48 h. Then the solvent was removed and the black residue was subjected to plug column chromatography (EtOAc) resulting in dark green oily residue. The compound was further purified by second column chromatography (2% MeOH/DCM). Pure product (3.5 g, 58%) as a slightly green oil was collected.

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 7.9 min (for boronic acid) and 12.6 min (for pinacol ester).

$^1$H NMR (400 MHz, CDCl$_3$): δ 1.35 (s, 12H), 2.58 (s, 3H), 7.26 (d, 1H), 7.55 (d, 1H), 8.00 (s, 1H).

Step 3

6-(Bromomethyl)-3-(trifluoromethyl)phenylboronic acid pinacol ester (25b)

6-Methyl-3-(trifluoromethyl)phenylboronic acid pinacol ester (24b, 3.0 g, 10 mmol) and 60 ml CCl$_4$ were placed in 500 ml round-bottom flask. NBS (1.9, 10.5 mmol, 1.05 eq) and AIBN (0.02 g, 0.14 mmol, 0.014 eq) were added and the reaction mixture was refluxed for 4.5 h in the presence of 75 W incandescent bulb. After 4.5 h the solution was cooled down to room temperature allowing the succinimide to precipitate out. The solid was filtered off. The solvent was removed and oily product was collected. The crude product was purified by triturating with hexane which resulted in 80% pure product (25b, 3.6 g, 95% yield).

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B MeCN (0.1% v/v TFA), gradient 10% B 1 min, 10-80% B over 9 min, 80-100% B over 1 min, 100% B 1 min, retention time 8.7 min (for boronic acid) and 12.4 min (for pinacol ester).

$^1$H NMR (400 MHz, CDCl$_3$): δ 1.38 (s, 12H), 4.91 (s, 2H), 7.50 (d, 1H), 7.64 (d, 1H), 8.06 (s, 1H).

Step 4

9-[N-[2-(4,4,5,5,-tetramethyl-1,3,2-dioxaborolano)-4-(trifluoromethyl)benzyl]-N-[3-(methacrylamido)propylamino]methyl]-10-[N-[2-(4,4,5,5,-tetramethyl-1,3,2-dioxaborolano)-4-(trifluoromethyl)benzyl]-N-[2-(tert-butoxycarbonyl)ethylamino]methyl] anthracene (26b)

9-[N-[3-(methacrylamido)propylamino]methyl]-10-[N-[2-(tert-butoxycarbonyl)ethylamino]methyl]-anthracene (1, 1.0 g, 2.0 mmol) was placed into 150 mL round-bottom flask. It was dissolved in 15 mL of degassed dimethylformamide. 6-(bromomethyl)-3-(trifluoromethyl)phenylboronic acid pinacol ester (25b, 1.75 g, 4.8 mmol, 2.4 equiv.) was dissolved in 5 mL of N$_2$ sparged DMF and added to reaction flask. The solution was stirred and flushed with N$_2$ for 5 minutes. DIEA (2.8 mL, 16 mmol, 8.0 equiv.) was added to the reaction mixture and the solution was allowed to stir under a gentle stream of nitrogen and in the dark at ambient temperature overnight. After 24 h the solvent was evaporated in vacuo. The residual product was dissolved in 10 mL of dichloromethane and extracted with 3×15 mL portions of phosphate buffer (0.1 M, pH 7.0). The dichloromethane solution was dried and evaporated in vacuo resulting in a golden oily residue. The crude product was stirred for 15 minutes with 10 mL of hexanes and then the solvent was removed. Collected yellow powder was crystallized from hot IPA resulting in pure product (26b, 1.2 g, 55% yield).

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 8.1 min.

$^1$H NMR (400 MHz, CDCl$_3$): δ 1.29 (s, 9H), 1.31 (s, 12H), 1.35 (s, 12H), 1.55 (bs, 3H), 1.73 (m, 2H), 2.52 (m, 4H), 2.91 (t, 2H), 3.10 (q, 2H), 3.95 (s, 2H), 4.05 (s, 2H), 4.45 (s, 2H), 4.51 (s, 2H), 4.97 (s, 2H), 5.05 (t, 1H), 7.42-7.47 (m, 6H), 7.54 (d, 1H), 7.60 (d, 1H), 7.91 (s, 1H), 8.01 (s, 1H), 8.34 (m, 2H), 8.39 (m, 2H).

Step 5

9-[N-[2-(4,4,5,5,-tetramethyl-1,3,2-dioxaborolano)-4-(trifluoromethyl)benzyl]-N-[3-(methacrylamido) propyl amino]methyl]-10-[N-[2-(4,4,5,5,-tetramethyl-1,3,2-dioxaborolano)-4-(trifluoromethyl) benzyl]-N-[2-(carboxyethyl)amino]methyl] anthracene sodium salt (27b)

9-[N-[2-(4,4,5,5,-tetramethyl-1,3,2-dioxaborolano)-4-(trifluoromethyl)benzyl]-N-[3-(methacryl-amido)propylamino]methyl]-10-[N-[2-(4,4,5,5,-tetramethyl-1,3,2-dioxaborolano)-4-(trifluoro-methyl)benzyl]-N-[2-(tert-butoxycarbonyl)ethylamino]methyl]anthracene (26b, 0.39 g, 0.37 mmol) was placed into a 100 mL round bottom flask and dissolved in 20 mL of a 60:40 degassed CH$_2$Cl$_2$:TFA solution. The reaction mixture was allowed to stir at ambient temperature for 23 h. The residual product was washed with 10 mL of CH$_2$Cl$_2$ followed by removal of the solvent under vacuum. The dichloromethane washes were repeated several times. The powder was dissolved in 10 mL of dichloromethane and added dropwise into 80 mL cold saturated aqueous NaHCO$_3$ at a rate such that the temperature stayed below 5° C. The solution was stirred for an additional 5 min at <5° C. followed by partitioning of the layers. The organic extracts were dried over anhydrous Na$_2$SO$_4$, filtered and concentrated yielding 0.33 g yellow powder. The crude product was dissolved in 10 mL of anhydrous CH$_2$Cl$_2$ and transferred to a 100 mL round bottom flask. PS-DEAM beads (0.19 g, 1 eq) were added to the flask and the reaction mixture was shaken at ambient temperature for 16 h. The beads were filtered and washed with 5 mL dichloromethane. The combined organic solutions were concentrated under vacuum. Pure product (27b, 0.27 g, 72%) was obtained as a yellow powder.

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 7.2 min.

$^1$H NMR (400 MHz, CDCl$_3$): δ 1.33 (s, 12H), 1.39 (s, 12H) 1.60-1.63 (m, 5H), 2.33 (t, 2H), 2.47 (t, 2H), 2.85-2.96 (m, 4H), 4.05 (s, 2H), 4.33 (s, 2H), 4.46 (s, 2H), 4.60 (s, 2H), 5.03 (s, 1H), 5.18 (s, 1H), 5.52 (bt, 1H,), 7.35-7.43 (m, 4H), 7.55-7.66 (m, 2H), 7.68 (d, 1H), 7.77-7.88 (m, 3H), 8.03 (s, 1H), 8.24 (s, 1H), 8.30 (m, 2H).

ESI-MS (TFA/acetonitrile/water): 820.12 (M−H$_2$O+H)$^+$ for the bis-boronic acid. Boronic esters are not observed under the acidic conditions of this analysis.

EXAMPLE 19

Synthesis of 5-Fluoro Indicator

9-[N-[2-(4,4,5,5,-tetramethyl-1,3,2-dioxaborolano)-4-fluorobenzyl]-N-[3-(methacrylamido)propylamino]methyl]-10-[N-[2-(4,4,5,5,-tetramethyl-1,3,2-dioxaborolano)-4-fluorobenzyl]-N-[2-(carboxyethyl) amino]methyl]anthracene sodium salt (32a)

Step 1

3-Fluoro-6-methylphenylboronic acid pinacol ester (29a)

3-Fluoro-6-methylphenylboronic acid (10 g, 65 mmol) and 220 ml of diethyl ether were placed in round-bottom flask. Then pinacol was added (7.68 g, 65 mmol, 1 eq) and the resulting reaction mixture was stirred for couple of minutes until the solution became clear. Finally, MgSO$_4$ (15.6 g, 130 mmol, 2 eq) was added and the solution was allowed to stir at ambient temperature, under N$_2$ balloon overnight. After 24 h the reaction was worked up. MgSO$_4$ was filtered off and washed with Et$_2$O. Organic layer was collected and the solvent was then removed. Pure product (15.2 g, 99% yield) was obtained as a dark yellow oily residue.

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 6.1 min.

$^1$H NMR (400 MHz, CDCl$_3$): δ 1.34 (s, 12H), 2.48 (s, 3H), 6.97 (ddd, 1H), 7.09 (dd, 1H), 7.43 (dd, 1H).

Step 2

6-(Bromomethyl)-3-fluorophenylboronic acid pinacol ester (30a)

3-Fluoro-6-methylphenylboronic acid pinacol ester (29a, 5.01 g, 21.2 mmol) and 140 ml CCl$_4$ were placed in 500 ml round-bottom flask. NBS (3.97 g, 22.3 mmol, 1.05 eq) and AIBN (0.054 g, 0.33 mmol, 0.016 eq) were added and the reaction mixture was refluxed for 3.5 h in the presence of 75 W incandescent bulb. After 3.5 h the solution was cooled down to room temperature allowing the succinimide to precipitate out. The solid was filtered off. The solvent was removed and oily product was collected. Purification with column chromatography (95/5 Hexanes/Ethyl acetate) resulted in pure product (30a, 5.59 g, 84% yield).

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 7.2 min (for free boronic acid) and 12.1 min (for pinacol ester).

$^1$H NMR (400 MHz, CDCl$_3$): δ 1.36 (s, 12H), 4.88 (s, 2H), 7.04-7.09 (ddd, 1H), 7.33-7.37 (dd, 1H), 7.47-7.50 (dd, 1H).

Step 3

9-[N-[2-(4,4,5,5,-tetramethyl-1,3,2-dioxaborolano)-4-fluorobenzyl]-N-[3-(metha-crylamido)propy-lamino]methyl]-10-[N-[2-(4,4,5,5,-tetramethyl-1,3,2-dioxaborolano)-4-fluorobenzyl]-N-[2-(tert-butoxycarbonyl)ethylamino]methyl]anthracene (31a):

9-[N-[3-(methacrylamido)propylamino]methyl]-10-[N-[2-(tert-butoxycarbonyl)ethylamino]methyl]-anthracene (1, 1.0 g, 2.04 mmol) was placed into 100 mL round-bottom flask and stirred in 16 mL dimethylformamide until dissolved. 6-(Bromomethyl)-3-fluorophenylboronic acid pinacol ester (30a, 1.96, 6.22 mmol, 3.0 equiv.) and DIEA (2.8 mL, 16 mmol, 8.0 eq) were added and stirred under N$_2$, in the dark, at room temperature for 24 h. The DMF was removed under vacuum; dichloromethane (20 mL) added and washed with phosphate buffer (40 mL of 0.1 M, pH 7.0). Collected dichloromethane solution was dried over Na$_2$SO$_4$. The dichloromethane was removed under vacuum and the resulting yellow residue triturated with hexanes (10 mL) for 15 minutes under slow flow of N$_2$. The crude product (1.6 g) was crystallized from hot IPA twice yielding a yellow powder of 98.6% purity by HPLC (31a, 0.89 g, 45% yield).

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 7.3 min.

$^1$H NMR (400 MHz, CDCl$_3$): δ1.29 (s, 9H), 1.31 (s, 12H), 1.35 (s, 12H), 1.55 (bs, 3H), 1.72 (m, 2H), 2.54 (m, 4H), 2.92 (t, 2H), 3.09 (q, 2H), 3.95 (s, 2H), 4.03 (s, 2H), 4.47 (s, 2H), 4.51 (s, 2H), 4.96 (s, 2H), 5.05 (t, 1H), 7.42-7.46 (m, 6H), 7.54 (d, 1H), 7.60 (d, 1H), 7.90 (s, 1H), 8.01 (s, 1H), 8.32 (m, 2H), 8.38 (m, 2H).

Step 4

9-[N-[2-(4,4,5,5,-tetramethyl-1,3,2-dioxaborolano)-4-fluorobenzyl]-N-[3-(methacrylamido)propy-lamino]methyl]-10-[N-[2-(4,4,5,5,-tetramethyl-1,3,2-dioxaborolano)-4-fluorobenzyl]-N-[2-(carboxyethyl) amino]methyl]anthracene sodium salt (32a)

9-[N-[2-(4,4,5,5,-tetramethyl-1,3,2-dioxaborolano)-4-fluorobenzyl]-N-[3-(methacrylamido)-propylamino]methyl]-10-[N-[2-(4,4,5,5,-tetramethyl-1,3,2-dioxaborolano)-4-fluoro-benzyl]-N-[2-(tert-butoxycarbonyl)ethylamino] methyl]anthracene (31a, 0.79 g, 0.82 mmol) was placed into a 100 mL round bottom flask and dissolved in 30 mL of a 60:40 CH$_2$Cl$_2$:TFA solution. The reaction mixture was allowed to stir at ambient temperature overnight. After 24 h the solvents were removed under vacuum. The residual product was dissolved in 10 mL of CH$_2$Cl$_2$ followed by removal of the solvent under vacuum. The dichloromethane dissolution/evaporation treatments were repeated until the product became a yellow powder. The powder was dissolved in 30 mL of dichloromethane and added dropwise into 50 mL cold saturated aqueous NaHCO$_3$ at a rate such that the temperature stayed below 5° C. The solution was stirred for an additional 5 min at <5° C. followed by partitioning of the layers. The organic layer was dried over anhydrous Na$_2$SO$_4$, filtered and concentrated yielding 0.7 g yellow powder. The crude product was dissolved in 20 mL of anhydrous CH$_2$Cl$_2$ and transfered to a 100 mL round bottom flask. PS-DEAM beads (0.44 g, 1 eq) were added to the flask and the reaction mixture was shaken at ambient temperature for 16 h. The beads were filtered and washed with 5 mL dichloromethane. The combined organic solutions were concentrated under vacuum. Pure product (0.55 g, 71%) was obtained as a yellow powder.

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 6.4 min.

$^1$H NMR (400 MHz, CDCl$_3$): δ 1.33 (s, 12H), 1.37 (s, 12H), 1.56 (t, 2H), 1.62 (s, 3H), 2.24 (t, 2H), 2.43 (t, 2H), 2.86 (m, 2H), 4.00 (s, 2H), 4.27 (s, 2H), 4.43 (s, 2H), 4.61 (s, 2H), 4.89 (t, 1H), 5.12 (s, 1H), 5.48 (m, 1H), 7.12 (ddd, 1H), 7.29 (ddd, 1H), 7.38 (m, 4H), 7.44-7.52 (m, 2H), 7.57 (dd, 1H), 7.69 (dd, 1H), 7.83 (m, 2H), 8.24 (m, 2H).

EXAMPLE 20

Synthesis of 4-Chloro Indicator

9-[N-[6-(4,4,5,5,-tetramethyl-1,3,2-dioxaborolano)-3-chlorobenzyl]-N-[3-(methacrylamido)propy-lamino]methyl]-10-[N-[6-(4,4,5,5,-tetramethyl-1,3,2-dioxaborolano)-3-chlorobenzyl]-N-[2-(carboxyethyl) amino]methyl]anthracene sodium salt (32b)

Step 1

4-Chloro-2-methylphenylboronic acid pinacol ester (29b)

4-Chloro-2-methylphenylboronic acid (5.0 g, 29 mmol) and 100 ml of Diethyl ether were placed in round-bottom flask. Then pinacol was added (3.43, 29 mmol, 1 eq) and the resulting reaction mixture was stirred for couple of minutes until the solution became clear. Finally, MgSO$_4$ (6.98, 58 mmol, 2 eq) was added and the solution was allowed to stir at ambient temperature, under N$_2$ balloon overnight. After 24 h the reaction was worked up. MgSO$_4$ was filtered off and washed with Et$_2$O. Organic layer was collected and the solvent was then removed. Pure product (7.2 g, 97% yield) was obtained as a white powder.

Structure Determination:

RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 12.6 min.

¹H NMR (400 MHz, CDCl₃): δ 1.33 (s, 12H), 2.50 (s, 3H), 7.14 (m, 2H), 7.68 (d, 1H).

Step 2

2-(Bromomethyl)-4-chlorophenylboronic acid pinacol ester (30b)

4-Chloro-2-methylphenylboronic acid pinacol ester (29b, 7.2 g, 28.5 mmol) and 100 ml CCl₄ were placed in 500 ml round-bottom flask. NBS (5.3 g, 29.9 mmol, 1.05 eq) and AIBN (0.066 g, 0.399 mmol, 0.014 eq) were added and the reaction mixture was refluxed for 6 h in the presence of 75 W incandescent bulb. After 6 h the solution was cooled down to room temperature allowing the succinimide to precipitate out. The solid was filtered off. The solvent was removed and the product was collected (30b, 9.3 g, 99% yield).

Structure Determination:
RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 8.05 min (for free boronic acid) and 12.4 min (for pinacol ester).

¹H NMR (400 MHz, CDCl₃): δ 1.36 (s, 12H), 4.85 (s, 2H) 7.24-7.28 (m, 1H), 7.58 (d, 1H), 7.74 (d, 1H).

Step 3

9-[N-[6-(4,4,5,5,-tetramethyl-1,3,2-dioxaborolano)-3-chlorobenzyl]-N-[3-(metha-crylamido)propylamino]methyl]-10-[N-[6-(4,4,5,5,-tetramethyl-1,3,2-dioxaborolano)-3-chlorobenzyl]-N-[2-(tert-butoxycarbonyl)ethylamino]methyl]anthracene (31b):

9-[N-[3-(methacrylamido)propylamino]methyl]-10-[N-[2-(tert-butoxycarbonyl)ethylamino]methyl]-anthracene (1, 1.0 g, 2.04 mmol) was placed into 100 mL round-bottom flask and stirred in 15 mL dimethylformamide until dissolved. 2-(Bromomethyl)-4-chlorophenylboronic acid pinacol ester (30b, 1.8, 4.89 mmol, 2.4 equiv.) and DIEA (2.78 mL, 16.3 mmol, 8.0 eq) were added and stirred under N₂, in the dark, at room temperature for 24 h. The DMF was removed under vacuum; dichloromethane (100 mL) added and washed with phosphate buffer (2×100 mL of 0.1 M, pH 7.0). Collected dichloromethane solution was dried over Na₂SO₄. The dichloromethane was removed under vacuum and the resulting yellow residue triturated with hexanes (10 mL) for 30 minutes under slow flow of N₂. The crude product (1.9 g) was crystallized from hot IPA yielding a light pink powder (31b, 1.6 g, 79% yield).

Structure Determination:
RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 7.7 min.

¹H NMR (400 MHz, CDCl₃): δ 1.27 (s, 9H), 1.31 (s, 12H), 1.35 (s, 12H), 1.50 (bs, 3H), 1.66 (m, 2H), 2.44 (t, 2H), 2.53 (t, 2H), 2.88 (t, 2H), 3.06 (q, 2H), 3.93 (s, 2H), 4.02 (s, 2H), 4.43 (s, 2H), 4.47 (s, 2H), 4.87 (s, 1H), 4.92 (bs, 1H), 5.00 (t, 1H), 7.09-7.15 (dd, 1H), 7.22-7.26 (dd, 1H), 7.37 (d, 1H), 7.42-7.48 (m, 4H), 7.53 (d, 1H), 7.63 (d, 1H), 7.72 (d, 1H), 8.30-8.39 (m, 4H).

Step 4

9-[N-[6-(4,4,5,5,-tetramethyl-1,3,2-dioxaborolano)-3-chlorobenzyl]-N-[3-(methacrylamido)propylamino]methyl]-10-[N-[6-(4,4,5,5,-tetramethyl-1,3,2-dioxaborolano)-3-chlorobenzyl]-N-[2-(carboxyethyl)amino]methyl]anthracene sodium salt (32b)

9-[N-[6-(4,4,5,5,-tetramethyl-1,3,2-dioxaborolano)-3-chlorobenzyl]-N-[3-(methacrylamido)-propylamino]methyl]-10-[N-[6-(4,4,5,5,-tetramethyl-1,3,2-dioxaborolano)-3-chlorobenzyl]-N-[2-(tert-butoxycarbonyl)ethylamino]methyl]anthracene (31b, 11.0 g, 10.09 mmol) was placed into a 100 mL round bottom flask and dissolved in 20 mL of a 60:40 CH₂Cl₂:TFA solution. The reaction mixture was allowed to stir at ambient temperature, under N₂ balloon overnight. After 20 h the solvents were removed under vacuum. The residual product was dissolved in 10 mL of CH₂Cl₂ followed by removal of the solvent under vacuum. The dichloromethane dissolution/evaporation treatments were repeated until the product became a yellow powder. The powder was dissolved in 30 mL of dichloromethane and added dropwise into 80 mL cold saturated aqueous NaHCO₃ at a rate such that the temperature stayed below 5° C. The solution was stirred for an additional 5 min at <5° C. followed by partitioning of the layers. The organic layer was dried over anhydrous Na₂SO₄, filtered and concentrated yielding 0.7 g yellow powder. The crude product was dissolved in 20 mL of anhydrous CH₂Cl₂ and transferred to a 100 mL round bottom flask. PS-DEAM beads (0.42 g, 1 eq) were added to the flask and the reaction mixture was shaken at ambient temperature for 16 h. The beads were filtered and washed with 5 mL dichloromethane. The combined organic solutions were concentrated under vacuum. Pure product (32b, 0.55 g, 57%) was obtained as a yellow powder.

Structure Determination:
RP-HPLC Conditions: HP 1100 HPLC chromatograph, Waters 3.9×150 mm NovaPak HR C18 column with guard column, 0.010 mL injection, 1.5 mL/min, 1.500 mL injection loop, 254 nm detection, A=water (0.1% v/v TFA) and B=MeCN (0.1% v/v TFA), gradient 10% B 1 min, 10-80% B over 9 min, 80-100% B over 1 min, 100% B 1 min, retention time 6.9 min.

¹H NMR (400 MHz, CDCl₃): δ 1.34 (s, 12H), 1.37 (s, 12H), 1.56 (t, 2H), 1.62 (bs, 3H), 2.32 (t, 2H), 2.46 (t, 2H), 2.86 (t, 2H), 2.91 (q, 2H), 4.03 (s, 2H), 4.29 (s, 2H), 4.44 (s, 2H), 4.58 (s, 2H), 5.00 (t, 1H), 5.10 (s, 1H), 5.44 (bt, 1H), 7.24 (m, 1H), 7.40-7.46 (m, 5H), 7.53 (d, 1H), 7.60 (d, 1H), 7.74 (d, 1H), 7.84 (m, 2H), 7.96 (d, 1H), 8.24-8.34 (m, 2H).

ESI-MS (TFA/acetonitrile/water): 752.23 (M−H₂O)⁺ for the bis-boronic acid. Boronic esters are not observed under the acidic conditions of this analysis.

What is claimed is:
1. A method for using a molecule in oxidative conditions, which comprises:
  a) obtaining a molecule having an aryl boronic acid residue having one or more electron withdrawing groups on the aromatic moiety which contains the boronic acid residue, such that the molecule has enhanced oxidation resistance as compared to a corresponding molecule without the one or more electron withdrawing groups; and b) subjecting the molecule having the one or more electron withdrawing groups to oxidative conditions.

2. The method of claim 1, wherein the electron withdrawing group comprises one or more of the following: halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, or combinations thereof.

3. The method of claim 1, wherein the molecule having one or more electron withdrawing groups on the aromatic moiety further comprises a detectable group.

4. The method of claim 3, wherein the detectable group comprises an anthracene residue.

5. The method of claim 1, wherein the molecule having one or more electron withdrawing groups on the aromatic moiety is associated with a device that is implanted in a mammal.

6. The method of claim 5, wherein the device determines the presence or concentration of glucose in vivo.

7. The method of claim 1, wherein the molecule having one or more electron withdrawing groups on the aromatic moiety comprises:

9-[N-[6-(4,4,5,5,-tetramethyl-1,3,2-dioxaborolano)-3-(trifluoromethyl)benzyl]-N-[3-(methacrylamido)propyl-amino]methyl]-10-[N-[6-(4,4,5,5,-tetramethyl-1,3,2-dioxaborolano)-3-(trifluoromethyl)benzyl]-N-[2-carboxy-ethyl)amino]methyl]anthracene (4c);

9-[N-[6-(4,4,5,5,-tetramethyl-1,3,2-dioxaborolano)-3-(trifluoromethylsulfonyl)benzyl]-N-[3-(methacrylamido)propylamino]methyl]-10-[N-[6-(4,4,5,5,-tetramethyl-1,3,2-dioxaborolano)-3-(trifluoromethylsulfonyl)benzyl]-N-[2-(carboxyethyl)amino]methyl]anthracene (21);

9-[N-[6-(4,4,5,5,-tetramethyl-1,3,2-dioxaborolano)-2,4-bis(trifluoromethyl)benzyl]-N-[3-(methacrylamido)propylamino]methyl]-10-[N-[6-(4,4,5,5,-tetramethyl-1,3,2-dioxaborolano)-2,4-bis(trifluoromethyl)benzyl]-N-[2-(carboxyethyl)amino]-methyl]anthracene (27a);

or a residue or salt thereof.

8. A method for detecting the presence or concentration of an analyte in a sample in an oxidative environment, said method comprising:

a) exposing the sample to an indicator molecule having a detectable quality that changes when the indicator molecule is exposed to the analyte, said molecule comprising an aryl boronic acid residue having one or more electron withdrawing groups on the aromatic moiety which contains the boronic acid residue, such that the indicator molecule has enhanced oxidation resistance as compared to the corresponding molecule without the one or more electron withdrawing groups; and b) measuring any change in said detectable quality to thereby determine the presence or concentration of said analyte in said sample.

9. The method of claim 8, wherein the electron withdrawing group comprises one or more of the following: halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, or combinations thereof.

10. The method of claim 8, wherein the change in the detectable quality is an optical change.

11. The method of claim 8, wherein the analyte is glucose.

12. The method of claim 8, wherein the molecule having one or more electron withdrawing groups on the aromatic moiety comprises:

9-[N-[6-(4,4,5,5,-tetramethyl-1,3,2-dioxaborolano)-3-(trifluoromethyl)benzyl]-N-[3-(methacrylamido)propyl-amino]methyl]-10-[N-[6-(4,4,5,5,-tetramethyl-1,3,2-dioxaborolano)-3-(trifluoromethyl)benzyl]-N-[2-carboxy-ethyl)amino]methyl]anthracene (4c);

9-[N-[6-(4,4,5,5,-tetramethyl-1,3,2-dioxaborolano)-3-(trifluoromethylsulfonyl)benzyl]-N-[3-(methacrylamido)propylamino]methyl]-10-[N-[6-(4,4,5,5,-tetramethyl-1,3,2-dioxaborolano)-3-(trifluoromethylsulfonyl)benzyl]-N-[2-(carboxyethyl)amino]methyl]anthracene (21);

9-[N-[6-(4,4,5,5,-tetramethyl-1,3,2-dioxaborolano)-2,4-bis(trifluoromethyl)benzyl]-N-[3-(methacrylamido)propylamino]methyl]-10-[N-[6-(4,4,5,5,-tetramethyl-1,3,2-dioxaborolano)-2,4-bis(trifluoromethyl)benzyl]-N-[2-(carboxyethyl)amino]-methyl]anthracene (27a);

or a residue or salt thereof.

13. A compound having the following structure:

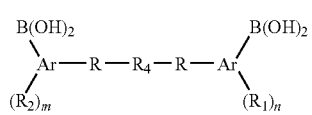

wherein:
each Ar is an aryl group;
each $R_1$ and $R_2$ are the same or different and are an electron withdrawing group;
m and n are each independently integers from 1 to 10;
$R_4$ is a detectable moiety; and
each R is independently a linking group having from zero to ten contiguous or branched carbon and/or heteroatoms, with at least one R further containing a polymerizable monomeric unit;

and wherein the compound has enhanced oxidation resistance as compared to the corresponding compound without the one or more electron withdrawing groups.

14. The compound of claim 13, wherein $R_1$ and $R_2$ each comprises one or more of the following: halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, or combinations thereof.

15. The compound of claim 13, wherein $R_4$ comprises an anthracene residue.

16. The compound of claim 13, wherein the compound comprises:

9-[N-[6-(4,4,5,5,-tetramethyl-1,3,2-dioxaborolano)-3-(trifluoromethyl)benzyl]-N-[3-(methacrylamido)propyl-amino]methyl]-10-[N-[6-(4,4,5,5,-tetramethyl-1,3,2-dioxaborolano)-3-(trifluoromethyl)benzyl]-N-[2-carboxy-ethyl)amino]methyl]anthracene (4c);

9-[N-[6-(4,4,5,5,-tetramethyl-1,3,2-dioxaborolano)-3-(trifluoromethylsulfonyl)benzyl]-N-[3-(methacrylamido)propylamino]methyl]-10-[N-[6-(4,4,5,5,-tetramethyl-1,3,2-dioxaborolano)-3-(trifluoromethylsulfonyl)benzyl]-N-[2-(carboxyethyl)amino]methyl]anthracene (21);

9-[N-[6-(4,4,5,5,-tetramethyl-1,3,2-dioxaborolano)-2,4-bis(trifluoromethyl)benzyl]-N-[3-(methacrylamido)propylamino]methyl]-10-[N-[6-(4,4,5,5,-tetramethyl-1,3,2-dioxaborolano)-2,4-bis(trifluoromethyl)benzyl]-N-[2-(carboxyethyl)amino]-methyl]anthracene (27a);

or a residue or salt thereof.

17. A compound having the following structure:

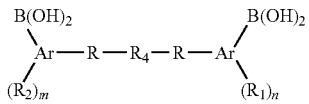

wherein:
  each Ar is an aryl group other than phenyl;
  each $R_1$ and $R_2$ are the same or different and are an electron withdrawing group;
  m and n are each independently integers from 1 to 10;
  $R_4$ is a detectable moiety; and
  each R is independently a linking group having from zero to ten contiguous or branched carbon and/or heteroatoms, with at least one R containing a linking group capable of attachment to a solid support or a polymeric matrix;
and wherein the compound has enhanced oxidation resistance as compared to the corresponding compound without the one or more electron withdrawing groups.

18. The compound of claim 17, wherein $R_1$ and $R_2$ each comprises one or more of the following: halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, or combinations thereof.

19. The compound of claim 17, wherein $R_4$ comprises an anthracene residue.

20. A method for the production of an indicator macromolecule for detecting the presence or concentration of an analyte in an oxidative environment, said method comprising copolymerizing:
  a) one or more indicator component monomers which individually are not sufficiently water soluble to permit their use in an aqueous environment for detecting the presence or concentration of said analyte, wherein the indicator component monomer comprises compound having the following structure:

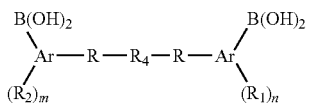

wherein:
  each Ar is an aryl group;
  each $R_1$ and $R_2$ are the same or different and are an electron withdrawing group;
  m and n are each independently integers from 1 to 10;
  $R_4$ is a detectable moiety; and
  each R is independently a linking group having from zero to ten contiguous or branched carbon and/or heteroatoms, with at least one R further containing a polymerizable monomeric unit; and
  b) one or more hydrophilic monomers;
such that the resulting macromolecule is capable of detecting the presence or concentration of said analyte in an aqueous environment and wherein the compound has enhanced oxidation resistance as compared to the corresponding compound without the one or more electron withdrawing groups.

21. The method of claim 20, wherein $R_1$ and $R_2$ each comprises one or more of the following: halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, or combinations thereof.

22. The method of claim 20, wherein $R_4$ comprises an anthracene residue.

23. The method of claim 20, wherein the compound comprises:
  9-[N-[6-(4,4,5,5,-tetramethyl-1,3,2-dioxaborolano)-3-(trifluoromethyl)benzyl]-N-[3-(methacrylamido)propyl-amino]methyl]-10-[N-[6-(4,4,5,5,-tetramethyl-1,3,2-dioxaborolano)-3-(trifluoromethyl)benzyl]-N-[2-carboxy-ethyl)amino]methyl]anthracene (4c);
  9-[N-[6-(4,4,5,5,-tetramethyl-1,3,2-dioxaborolano)-3-(trifluoromethylsulfonyl)benzyl]-N-[3-(methacrylamido)propylamino]methyl]-10-[N-[6-(4,4,5,5,-tetramethyl-1,3,2-dioxaborolano)-3-(trifluoromethylsulfonyl)benzyl]-N-[2-(carboxyethyl)amino]methyl]anthracene (21);
  9-[N-[6-(4,4,5,5,-tetramethyl-1,3,2-dioxaborolano)-2,4-bis(trifluoromethyl)benzyl]-N-[3-(methacrylamido)propylamino]methyl]-10-[N-[6-(4,4,5,5,-tetramethyl-1,3,2-dioxaborolano)-2,4-bis(trifluoromethyl)benzyl]-N-[2-(carboxyethyl)amino]-methyl]anthracene (27a);
or a residue or salt thereof.

24. A compound having the following structure:

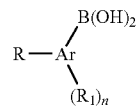

wherein:
  Ar is an aryl group;
  each $R_1$ is the same or different and is an electron withdrawing group;
  n is an integer from 1 to 10; and
  R is a linking group having from zero to ten contiguous or branched carbon and/or heteroatoms, which linking group further contains a polymerizable monomeric unit and a detectable moiety;
and wherein the compound has enhanced oxidation resistance as compared to the corresponding compound without electron withdrawing group(s).

25. The compound of claim 24, wherein $R_1$ comprises one or more of the following: halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, or combinations thereof.

26. The compound of claim 24, wherein the detectable moiety comprises an anthracene residue.

27. A compound having the following structure:

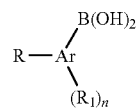

wherein:
Ar is an aryl group;
each $R_1$ is the same or different and is an electron withdrawing group;
n is an integer from 1 to 10; and
R is a linking group to a chromatographic support, said linking group having from zero to ten contiguous or branched carbon and/or heteroatoms;

and wherein the compound has enhanced oxidation resistance as compared to the corresponding compound without electron withdrawing group(s).

28. The compound of claim 27, wherein $R_1$ comprises one or more of the following: halogen, cyano, nitro, halo substituted alkyl, carboxylic acid, ester, sulfonic acid, ketone, aldehyde, sulfonamide, sulfone, sulfonyl, sulfoxide, halo-substituted sulfone, halo-substituted alkoxy, halo-substituted ketone, amide, or combinations thereof.

* * * * *